(12) United States Patent
Morris et al.

(10) Patent No.: US 11,608,323 B2
(45) Date of Patent: Mar. 21, 2023

(54) HERBICIDAL COMPOUNDS

(71) Applicants: SYNGENTA LIMITED, Guildford (GB); SYNGENTA PARTICIPATIONS AG, Basel (CH)

(72) Inventors: James Alan Morris, Bracknell (GB); Jutta Elisabeth Boehmer, Bracknell (GB); Ravindra Sonawane, Ilhas (IN); Timothy Robert Desson, Bracknell (GB); Sally Elizabeth Russell, Bracknell (GB); Kenneth Ling, Bracknell (GB); Alan Joseph Hennessy, Bracknell (GB); Matthew Brian Hotson, Bracknell (GB); Adrian Longstaff, Sr., Bracknell (GB); Mangala Phadte, Ilhas (IN); Claire Janet Russell, Bracknell (GB); Jake Goodwin-Tindall, Bracknell (GB)

(73) Assignees: SYNGENTA PARTICIPATIONS AG, Basel (CH); SYNGENTA LIMITED, Guildford (GB)

( * ) Notice: Subject to any disclaimer, the term of this patent is extended or adjusted under 35 U.S.C. 154(b) by 341 days.

(21) Appl. No.: 16/222,900

(22) Filed: Dec. 17, 2018

(65) Prior Publication Data
US 2019/0112288 A1 Apr. 18, 2019

Related U.S. Application Data

(63) Continuation of application No. 15/027,768, filed as application No. PCT/EP2014/071167 on Oct. 2, 2014, now abandoned.

(30) Foreign Application Priority Data

Oct. 7, 2013 (IN) .......................... 2977/DEL/2013

(51) Int. Cl.
| | | |
|---|---|---|
| *A01N 43/36* | (2006.01) | |
| *C07D 207/22* | (2006.01) | |
| *C07D 207/277* | (2006.01) | |
| *A01N 43/50* | (2006.01) | |
| *A01N 43/90* | (2006.01) | |
| *A01N 53/00* | (2006.01) | |
| *C07D 401/04* | (2006.01) | |
| *A01N 43/54* | (2006.01) | |
| *C07D 401/14* | (2006.01) | |

(Continued)

(52) U.S. Cl.
CPC .......... *C07D 401/04* (2013.01); *A01N 43/50* (2013.01); *A01N 43/54* (2013.01); *A01N 43/90* (2013.01); *A01N 53/00* (2013.01); *C07D 401/14* (2013.01); *C07D 405/14* (2013.01); *C07D 487/04* (2013.01); *C07D 498/04* (2013.01)

(58) Field of Classification Search
CPC .. C07D 401/04; C07D 401/14; C07D 405/14; C07D 487/04; C07D 498/04; A01N 43/50; A01N 43/54; A01N 43/90; A01N 53/00; G02B 27/0093; C07B 2200/13
See application file for complete search history.

(56) References Cited

U.S. PATENT DOCUMENTS 3,905,996 A * 9/1975 Perronnet ............. C07C 265/12
548/322.5
4,426,527 A 1/1984 Lavanish et al.
(Continued)

FOREIGN PATENT DOCUMENTS

CN 87100616 A 8/1987
EP 0133310 A1 7/1984
(Continued)

OTHER PUBLICATIONS

Chhokar et al. Journal of Wheat Research 4.2 (2012), 1-21 (Year: 2012).*

(Continued)

*Primary Examiner* — Mina Haghighatian
*Assistant Examiner* — Janice Y Silverman
(74) *Attorney, Agent, or Firm* — BakerHostetler; Toni-Junell Herbert

(57) ABSTRACT

The invention relates to pyrrolone compounds of the formula (I)

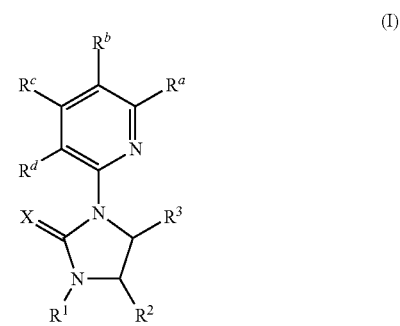

wherein X, $R^1$, $R^2$, $R^3$, $R^a$, $R^b$, $R^c$ and $R^d$ are as defined in the specification. Furthermore, the present invention relates to processes and intermediates for making compounds of formula (I), to herbicidal compositions comprising these compounds and to methods of using these compounds to control plant growth.

9 Claims, No Drawings

(51) Int. Cl.
*C07D 405/14* (2006.01)
*C07D 487/04* (2006.01)
*C07D 498/04* (2006.01)

(56) References Cited

U.S. PATENT DOCUMENTS 4,600,430 A 7/1986 Abdulla et al.
4,604,127 A 8/1986 Abdulla et al.

FOREIGN PATENT DOCUMENTS

EP 0234323 A1 1/1987
FI 62838 * 11/1982 ......... A61K 31/4245

OTHER PUBLICATIONS

Cerecetto et al. J. Agric. Food Chem. 2000, 48, 2995-3002 (Year: 2000).*
Hoffman et al. Intermediate Text, Second Edition, 2004 (Year: 2004).*
Patani et al. Chemical Reviews, 1996, V. 96, 8, 3147-3176 (Year: 1996).*
Han et. al., "Synthesis and Herbicidal Activity of 5-(4-Hydroxybenzyl)-2-Thioxoimidazolidin-4-one Esters", Molecules 2011, vol. 16, pp. 2833-2845.
Yonova P et al; Synthesis and plant growth-regulating activity Pyridyl-Imidazolidinone Compounds, Jan. 1, 2005, pp. 595-600, Issue 1310-1331.
International Search Report for International Application No. PCT/EP2014/071167, dated Jan. 9, 2015.

\* cited by examiner

HERBICIDAL COMPOUNDS

This application is a continuation of co-pending U.S. application Ser. No. 15/027,768 filed Apr. 7, 2016, which is 371 national stage entry of International Application No. PCT/EP2014/071167 filed Oct. 2, 2014 which claims priority to Indian Application 2977/DEL/2013 filed Oct. 7, 2013 the contents of which are incorporated herein by reference.

The present invention relates to certain substituted dihydro-hydantoin derivatives, to processes for their preparation, herbicidal compositions comprising them, and their use in controlling plants or inhibiting plant growth.

Herbicidal dihydro-hydantoins of the formula

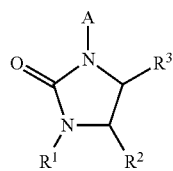

wherein A is a pyridine ring are taught in U.S. Pat. No. 4,600,430. Similar compounds wherein A is a pyridazine ring are taught in U.S. Pat. No. 4,604,127.

SUMMARY OF THE INVENTION

In a first aspect, the invention provides compounds of the formula (I)

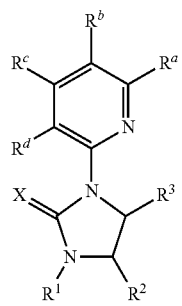

(I)

wherein
X is selected from S and O;
$R^a$ is selected from hydrogen and halogen;
$R^b$ is selected from hydrogen, halogen, $C_1$-$C_4$ alkyl, $C_2$-$C_4$ alkenyl $C_1$-$C_4$ haloalkyl, $C_1$-$C_6$ alkoxy, $C_2$-$C_4$ alkenyloxy, $C_2$-$C_4$ alkynyloxy, $C_1$-$C_4$ alkoxy-$C_1$-$C_4$ alkyl, $C_1$-$C_4$ haloalkoxy, $C_1$-$C_3$ alkoxy-$C_1$-$C_3$ alkoxy, $C_1$-$C_4$ alkylthio, $C_1$-$C_4$ alkylsulfinyl, $C_1$-$C_4$ alkylsulfonyl, a group $R^5R^6N$—, a group $R^5C(O)N(R^6)$—, a group $R^5S(O_2)N(R^6)$—, a group $R^5R^6NSO_2$—, a group $R^5R^6NC(O)$—, aryl optionally substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, aryloxy optionally substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy and heteroaryl optionally substituted substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;
$R^c$ is selected from hydrogen, halogen, $C_1$-$C_8$ alkyl, $C_1$-$C_6$ haloalkyl, $C_2$-$C_8$ alkenyl, $C_1$-$C_6$ cyanoalkyl, $C_1$-$C_6$ alkoxy, $C_1$-$C_4$ alkoxy-$C_1$-$C_4$ alkyl, $C_1$-$C_6$ hydroxyalkyl, $C_2$-$C_6$ alkenyloxy $C_1$-$C_6$ alkyl and $C_3$-$C_6$ cycloalkyl optionally substituted by from 1 to 3 groups independently selected from cyano, $C_1$-$C_3$ alkyl and $C_1$-$C_3$ alkoxy;
$R^d$ is selected from hydrogen, halogen, cyano, $C_1$-$C_6$ alkyl and $C_1$-$C_6$ haloalkyl;
$R^1$ is selected from hydrogen, hydroxyl, $C_1$-$C_4$ alkyl, $C_2$-$C_4$ alkenyl, $C_2$-$C_4$ alkynyl, $C_1$-$C_4$ cyanoalkyl, $C_3$-$C_6$ cycloalkyl, $C_1$-$C_4$ alkoxy, $C_1$-$C_4$ alkoxy-$C_1$-$C_4$ alkyl and $C_1$-$C_4$ haloalkyl and $R^2$ is selected from hydrogen, hydroxyl, $C_1$-$C_4$ alkyl, $C_2$-$C_4$ alkenyl, $C_1$-$C_4$ alkoxy, $C_2$-$C_4$ alkenyloxy, $C_2$-$C_4$ alkynyloxy, $C_1$-$C_4$ alkoxy-$C_1$-$C_4$ alkyl, $C_1$-$C_4$ alkoxy-$C_1$-$C_4$ alkoxy, $C_1$-$C_4$ hydroxyalkyl, $C_1$-$C_4$ haloalkyl, $C_1$-$C_3$ haloalkoxy and $C_1$-$C_4$ cyanoalkyl, with the proviso that when $R^1$ is methyl, $R^2$ is not H;
or $R^1$ and $R^2$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from hydroxyl, =O, $C_1$-$C_6$ alkyl or $C_1$-$C_6$ haloalkyl.
$R^3$ is selected from halogen, hydroxyl, —$NR^{14}R^{15}$, or any one of the following groups

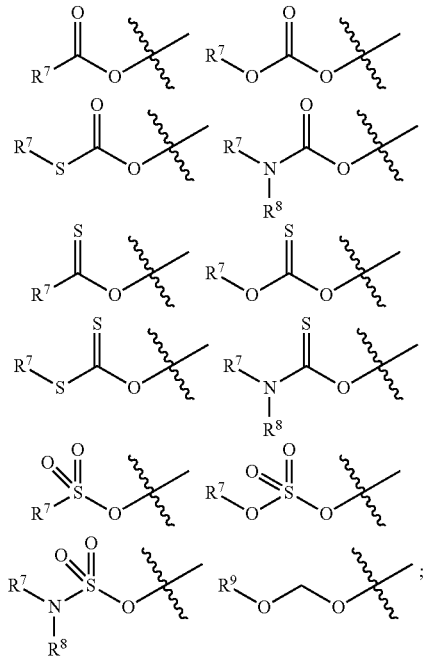

$R^5$ and $R^6$ are independently selected from hydrogen, $C_1$-$C_6$ alkyl, $C_1$-$C_6$ haloalkyl, $C_1$-$C_6$ cyanoalkyl, $C_2$-$C_6$ alkenyl, $C_2$-$C_6$ alkynyl, $C_1$-$C_6$ alkoxy and $C_1$-$C_6$ alkoxy-$C_1$-$C_6$ alkyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;
$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_3$-$C_6$ cycloalkyl group optionally substituted with 1 to 3 groups independently selected from $C_1$-$C_3$ alkyl, $C_2$-$C_4$ alkenyl, $C_1$-$C_3$ haloalkyl and $C_2$-$C_4$ haloalkenyl, a $C_5$-$C_{10}$ heterocyclyl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, a $C_6$-$C_{10}$ arylalkyl group optionally substituted with 1 to 3 groups independently selected from $C_1$-$C_4$ alkyl, $C_1$-$C_3$ alkoxy, $C_1$-$C_3$ haloalkyl and the group OC(O)—$C_1$-$C_4$ alkyl, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

$R^9$ is selected from $C_1$-$C_6$ alkyl and benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;

$R^{14}$ and $R^{15}$ are, independently, selected from hydrogen, $C_1$-$C_{20}$ alkyl, $C_1$-$C_{20}$ haloalkyl, $C_1$-$C_{20}$ alkoxy, $C_1$-$C_{20}$ alkoxy-$C_1$-$C_{20}$ alkyl, $C_2$-$C_{20}$ alkenyl, $C_2$-$C_{20}$ alkynyl and benzyl, or $R^{14}$ and $R^{15}$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

or an N-oxide or salt form thereof.

In a second aspect, the invention provides herbicidal compositions comprising a compound of the invention together with at least one agriculturally acceptable adjuvant or diluent.

In a third aspect, the invention provides the use of a compound or a composition of the invention for use as a herbicide.

In a fourth aspect, the invention provides a method of controlling weeds in crops of useful plants, comprising applying to said weeds or to the locus of said weeds, or to said useful crop plants, a compound or a composition of the invention.

In a fifth aspect, the invention relates to processes useful in the preparation of compounds of the invention.

In a sixth aspect, the invention relates to intermediates useful in the preparation of compounds of the invention.

DETAILED DESCRIPTION

In particularly preferred embodiments of the invention, the preferred groups for X, $R^a$, $R^b$ $R^c$, $R^d$, $R^1$, $R^2$ and $R^3$, in any combination thereof, are as set out below.

Preferably, X is O.

Preferably, $R^a$ is hydrogen.

Preferably, $R^d$ is hydrogen.

Preferably, $R^1$ is selected from $C_1$-$C_4$ alkyl, $C_1$-$C_4$ alkoxy and $C_1$-$C_4$ haloalkyl. More preferably, $R^1$ is selected from $C_1$-$C_4$ alkyl and $C_1$-$C_4$ alkoxy. Most preferably, $R^1$ is selected from methyl and methoxy.

Preferably, $R^2$ is selected from $C_1$-$C_3$ alkyl, $C_1$-$C_3$ alkoxy and $C_1$-$C_3$ alkoxy-$C_1$-$C_3$ alkyl. More preferably, $R^2$ is selected from methyl, ethyl, methoxy, ethoxy and methoxymethyl. Even more preferably, $R^2$ is selected from methyl and ethoxy. Most preferably, $R^2$ is methyl.

Preferably, $R^3$ is selected from hydroxyl, halogen, $C_1$-$C_6$ alkylcarbonyloxy, $C_1$-$C_6$ alkoxycarbonyloxy and aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy. Even more preferably, $R^3$ is selected from hydroxyl and halogen. Most preferably, $R^3$ is hydroxyl.

In one embodiment, X, $R^a$, $R^d$, $R^1$, $R^2$ and $R^3$ are as described above in any combination and $R^b$ and $R^c$ are as described below in any combination.

Preferably $R^b$ is selected from hydrogen, halogen, $C_1$-$C_3$ alkyl, $C_1$-$C_3$ alkoxy, $C_1$-$C_3$ alkoxy-$C_1$-$C_3$ alkyl, heteroaryl substituted by halogen or methoxy and aryl substituted by halogen or methoxy. More preferably, $R^b$ is selected from hydrogen, halogen, methoxy, heteroaryl substituted by halogen or methoxy and aryl substituted by halogen or methoxy groups. Even more preferably, $R^b$ is hydrogen.

Preferably, $R^c$ is selected from $C_1$-$C_8$ alkyl, $C_1$-$C_6$ haloalkyl, $C_2$-$C_8$ alkenyl, $C_1$-$C_6$ cyanoalkyl and $C_3$-$C_6$ cycloalkyl optionally substituted by from 1 to 3 groups independently selected from cyano and $C_1$-$C_3$ alkyl.

Even more preferably, $R^c$ is selected from $C_1$-$C_6$ alkyl, $C_1$-$C_3$ haloalkyl, $C_1$-$C_6$ cyanoalkyl and $C_3$-$C_6$ cycloalkyl optionally substituted by from 1 to 3 groups independently selected from cyano and $C_1$-$C_3$ alkyl.

Even more preferably $R^c$ is selected from methyl, ethyl, iso-propyl, (2-methyl)-prop-1-yl, (1-methyl)-prop-1-yl, tert-butyl, (1,1-dimethyl)-prop-1-yl, (1,1-dimethyl)-but-1-yl, (1-methyl-1-ethyl)-prop-1-yl, cyclobutyl, cyclopropyl, (1-methyl)cycloprop-1-yl, (1-methyl-1-cyano)-eth-1-yl, (1-methyl-1-ethyl-2-cyano)-prop-1-yl, (1,1-dimethyl-2-cyano)-prop-1-yl, 1-fluoroethyl, 1,1-difluoroethyl, difluoromethyl, 1-fluoro-1-methylethyl and trifluoromethyl.

Even more preferably, $R^c$ is selected from tert-butyl, (1-methyl-1-cyano)-eth-1-yl, 1,1-difluoroethyl, 1-fluoro-1-methylethyl and trifluoromethyl.

Most preferably, $R^c$ is trifluoromethyl.

In particular, the substituted pyridine may be 4-tert-butyl-pyrid-2-yl, 4-((1-methyl-1-cyano)-eth-1-yl)-pyrid-2-yl, 4-(1,1-difluoroethyl)-pyrid-2-yl, 4-(1-fluoro-1-methylethyl)-pyrid-2-yl or 4-(trifluoromethyl)-pyrid-2-yl.

In a further embodiment, X, $R^a$, $R^d$, $R^1$, $R^2$ and $R^3$ are as described above in any combination and $R^b$ is selected from $R^5R^6NC(O)$— and $R^5C(O)N(R^6)$—, wherein $R^5$ and $R^6$ are as described above, and $R^c$ is selected from hydrogen, halo, $C_1$-$C_4$ alkyl and $C_1$-$C_4$ haloalkyl. More preferably, $R^b$ is $R^5R^6NC(O)$—.

In a further embodiment, X, $R^a$, $R^d$, $R^1$, $R^2$ and $R^3$ are as described above in any combination and $R^b$ is selected from halogen and $C_1$-$C_4$ alkyl and $R^c$ is $C_1$-$C_3$ haloalkyl, preferably trifluoromethyl.

In a further embodiment, the invention provides compounds of the formula (I)

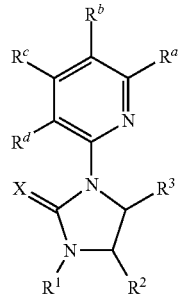

(I)

wherein

X is selected from S and O;

$R^a$ is selected from hydrogen and halogen;

$R^b$ is selected from hydrogen, halogen, $C_1$-$C_4$ alkyl, $C_1$-$C_4$ haloalkyl, $C_1$-$C_6$ alkoxy, $C_1$-$C_3$ alkoxy-$C_1$-$C_3$ alkoxy, a group $R^5R^6N$—, a group $R^5C(O)N(R^6)$—, a group $R^5S(O_2)N(R^6)$—, a group $R^5R^6NSO_2$—, a group $R^5R^6NC(O)$—, aryl optionally substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, and heteroaryl optionally substituted substituted by one or more groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;

$R^c$ is selected from hydrogen, halogen, $C_1$-$C_8$ alkyl, $C_1$-$C_6$ haloalkyl, $C_2$-$C_8$ alkenyl, $C_1$-$C_6$ cyanoalkyl, $C_1$-$C_6$ alkoxy, $C_1$-$C_6$ hydroxyalkyl, $C_2$-$C_6$ alkenyloxy $C_1$-$C_6$ alkyl and $C_3$-$C_6$ cycloalkyl optionally substituted by from 1 to 3 groups independently selected from cyano, $C_1$-$C_3$ alkyl and $C_1$-$C_3$ alkoxy;

$R^d$ is selected from hydrogen, halogen, cyano, $C_1$-$C_6$ alkyl and $C_1$-$C_6$ haloalkyl;

$R^1$ is selected from hydrogen, $C_1$-$C_4$ alkyl, $C_1$-$C_4$ alkoxy and $C_1$-$C_4$ haloalkyl and $R^2$ is selected from hydrogen, hydroxyl, $C_1$-$C_4$ alkyl, $C_1$-$C_4$ alkoxy, $C_1$-$C_4$ alkoxy-$C_1$-$C_4$ alkyl, $C_1$-$C_4$ haloalkyl, $C_1$-$C_3$ haloalkoxy and $C_1$-$C_4$ cyanoalkyl, with the proviso that when $R^1$ is methyl, $R^2$ is not H;

or $R^1$ and $R^2$ together with the nitrogen and carbon atoms to which they are attached form a 3-7 membered saturated or partially unsaturated ring optionally comprising from 1 to 3 heteroatoms independently selected from S, O and N and optionally substituted with from 1 to 3 groups independently selected from hydroxyl, =O, $C_1$-$C_6$ alkyl or $C_1$-$C_6$ haloalkyl.

$R^3$ is selected from halogen, hydroxyl, and any one of the following groups

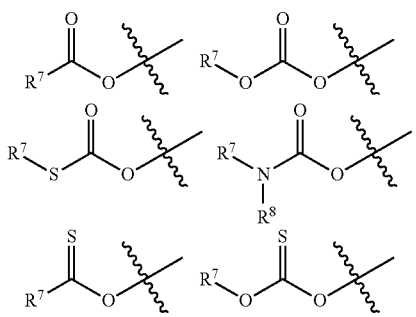

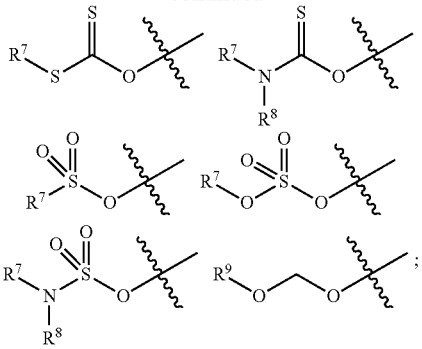

$R^5$ and $R^6$ are independently selected from hydrogen, $C_1$-$C_6$ alkyl, $C_1$-$C_6$ haloalkyl, $C_2$-$C_6$ alkenyl, $C_2$-$C_6$ alkynyl, or $R^5$ and $R^6$ together with the carbon atoms to which they are attached form a 3-6 membered saturated or partially unsaturated ring optionally comprising from 1 to 3 heteroatoms independently selected from S, O and N and optionally substituted with from 1 to 3 groups independently selected from halogen and $C_1$-$C_6$ alkyl;

$R^7$ and $R^8$ are independently selected from hydrogen, $C_1$-$C_6$ alkyl, $C_1$-$C_6$ haloalkyl, $C_2$-$C_6$ alkenyl, $C_2$-$C_6$ alkynyl, a $C_5$-$C_{10}$ heteroaryl group which can be mono- or bicyclic comprising from 1 to 4 heteroatoms independently selected from N, O and S and optionally substituted with 1 to 3 groups independently selected from halogen, $C_1$-$C_3$ alkyl, $C_1$-$C_3$ haloalkyl and $C_1$-$C_3$ alkoxy, a $C_6$-$C_{10}$ aryl group optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy, or $R^7$ and $R^8$ together with the atoms to which they are attached form a 3-6 membered saturated or partially unsaturated ring optionally comprising from 1 to 3 heteroatoms independently selected from S, O and N and optionally substituted with from 1 to 3 groups independently selected from halogen or $C_1$-$C_6$ alkyl;

$R^9$ is selected from $C_1$-$C_6$ alkyl and benzyl optionally substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy;

or an N-oxide or salt form thereof.

In this particular embodiment, the preferred groups for X, $R^a$, $R^b$, $R^c$, $R^d$, $R^1$, $R^2$ and $R^3$, in any combination thereof, are as set out below.

Preferably X is O.

Preferably $R^a$ is hydrogen.

Preferably, $R^d$ is hydrogen.

Preferably $R^1$ is $C_1$-$C_4$ alkyl, $C_1$-$C_4$ alkoxy or $C_1$-$C_4$ haloalkyl. More preferably, $R^1$ is $C_1$-$C_4$ alkyl or $C_1$-$C_4$ alkoxy. Most preferably, $R^1$ is methyl or methoxy.

Preferably $R^2$ is $C_1$-$C_3$ alkyl, $C_1$-$C_3$ alkoxy or $C_1$-$C_3$ alkoxy-$C_1$-$C_3$ alkyl. More preferably $R^2$ is methyl, methoxy, ethoxy or methoxymethyl.

Preferably, $R^3$ is hydroxyl, halogen, $C_1$-$C_6$ alkylcarbonyloxy, $C_1$-$C_6$ alkoxycarbonyloxy or aryloxycarbonyloxy wherein the aryl group may be substituted with 1 to 3 groups independently selected from halogen, nitro, cyano, $C_1$-$C_3$ alkyl, $C_1$-$C_3$ alkoxy, $C_1$-$C_3$ haloalkyl and $C_1$-$C_3$ haloalkoxy. Even more preferably, $R^3$ is hydroxyl or halogen. Most preferably, $R^3$ is hydroxyl.

In one embodiment of this embodiment, X, $R^a$, $R^d$, $R^1$, $R^2$ and $R^3$ are as described above in any combination and $R^b$ and $R^c$ are as described below in any combination.

Preferably $R^b$ is hydrogen, halogen, methoxy, heteroaryl substituted by halogen or methoxy or aryl substituted by halogen or methoxy groups.

Even more preferably, $R^b$ is hydrogen.

Preferably, $R^c$ is $C_1$-$C_8$ alkyl, $C_1$-$C_6$ haloalkyl, $C_2$-$C_8$ alkenyl, $C_1$-$C_6$ cyanoalkyl or $C_3$-$C_6$ cycloalkyl optionally substituted by from 1 to 3 groups independently selected from cyano and $C_1$-$C_3$ alkyl.

Even more preferably, $R^c$ is $C_1$-$C_6$ alkyl, $C_1$-$C_3$ haloalkyl, $C_1$-$C_6$ cyanoalkyl or $C_3$-$C_6$ cycloalkyl optionally substituted by from 1 to 3 groups independently selected from cyano and $C_1$-$C_3$ alkyl.

Even more preferably $R^c$ is methyl, ethyl, iso-propyl, (2-methyl)-prop-1-yl, (1-methyl)-prop-1-yl, tert-butyl, (1,1-dimethyl)-prop-1-yl, (1,1-dimethyl)-but-1-yl, (1-methyl-1-ethyl)-prop-1-yl, cyclobutyl, cyclopropyl, (1-methyl)cycloprop-1-yl, (1-methyl-1-cyano)-eth-1-yl, (1-methyl-1-ethyl-2-cyano)-prop-1-yl, (1,1-dimethyl-2-cyano)-prop-1-yl, 1-fluoroethyl, 1,1-difluoroethyl, difluoromethyl, 1-fluoro-1-methylethyl or trifluoromethyl.

Even more preferably, $R^c$ is tert-butyl, (1-methyl-1-cyano)-eth-1-yl, 1,1-difluoroethyl, 1-fluoro-1-methylethyl or trifluoromethyl.

Most preferably, $R^c$ is trifluoromethyl.

In particular, the substituted pyridine may be 4-tert-butyl-pyrid-2-yl, 4-((1-methyl-1-cyano)-eth-1-yl)-pyrid-2-yl, 4-(1,1-difluoroethyl)-pyrid-2-yl, 4-(1-fluoro-1-methyl-ethyl)-pyrid-2-yl or 4-(trifluoromethyl)-pyrid-2-yl.

In a further embodiment of this embodiment, X, $R^a$, $R^d$, $R^1$, $R^2$ and $R^3$ are as described above in any combination and $R^b$ is $R^5R^6NC(O)$— or $R^5C(O)N(R^6)$—, wherein $R^5$ and $R^6$ are as described above, and $R^c$ is hydrogen, halo, $C_1$-$C_4$ alkyl or $C_1$-$C_4$ haloalkyl. More preferably, $R^b$ is $R^5R^6NC(O)$—.

In a further embodiment of this embodiment, X, $R^a$, $R^d$, $R^1$, $R^2$ and $R^3$ are as described above in any combination and $R^b$ is halogen or $C_1$-$C_4$ alkyl and $R^c$ is $C_1$-$C_3$ haloalkyl, preferably trifluoromethyl.

The compounds of formula (I) may exist as different geometric isomers, or in different tautomeric forms. This invention covers all such isomers and tautomers, and mixtures thereof in all proportions, as well as isotopic forms such as deuterated compounds.

The compounds of this invention may contain one or more asymmetric centers and may thus give rise to optical isomers and diastereomers. While shown without respect to stereochemistry, the present invention includes all such optical isomers and diastereomers as well as the racemic and resolved, enantiomerically pure R and S stereoisomers and other mixtures of the R and S stereoisomers and agrochemically acceptable salts thereof. It is recognized certain optical isomers or diastereomers may have favorable properties over the other. Thus when disclosing and claiming the invention, when a racemic mixture is disclosed, it is clearly contemplated that both optical isomers, including diastereomers, substantially free of the other, are disclosed and claimed as well.

Alkyl, as used herein, refers to an aliphatic hydrocarbon chain and includes straight and branched chains e. g. of 1 to 8 carbon atoms such as methyl, ethyl, n-propyl, isopropyl, n-butyl, isobutyl, sec-butyl, t-butyl, n-pentyl, isopentyl, neopentyl, n-hexyl, and isohexyl.

Alkenyl, as used herein, refers to an aliphatic hydrocarbon chain having at least one double bond, and preferably one double bond, and includes straight and branched chains e. g. of 2 to 8 carbon atoms such as ethenyl (vinyl), prop-1-enyl, prop-2-enyl (allyl), isopropenyl, but-1-enyl, but-2-enyl, but-3-enyl, 2-methypropenyl.

Alkynyl, as used herein, refers to an aliphatic hydrocarbon chain having at least one triple bond, and preferably one triple bond, and includes straight and branched chains e. g. of 2 to 8 carbon atoms such as ethynyl, prop-1-ynyl, prop-2-ynyl (propargyl) but-1-ynyl, but-2-ynyl and but-3-ynyl.

Cycloalkyl, as used herein, refers to a cyclic, saturated hydrocarbon group having from 3 to 6 ring carbon atoms. Examples of cycloalkyl groups are cyclopropyl, cyclobutyl, cyclopentyl and cyclohexyl.

Hydroxyalkyl, as used herein, refers to the group —ROH, wherein R is alkyl as defined above.

Alkoxy, as used herein, refers to the group —OR, wherein R is alkyl as defined above. Examples of alkoxy groups include methoxy, ethoxy, n-propoxy, isopropoxy, n-butoxy, isobutoxy, sec-butoxy, t-butoxy, n-pentoxy, isopentoxy, neopentoxy, n-hexyloxy, and isohexyloxy.

Alkenyloxy, as used herein, refers to the group —OR, wherein R is alkenyl as defined above. Examples of alkenyloxy groups are ethenyloxy, propenyloxy, isopropenyloxy, but-1-enyloxy, but-2-enyloxy, but-3-enyloxy, 2-methypropenyloxy etc.

Alkynyloxy, as used herein, refers to the group —OR, wherein R is alkynyl is as defined above. Examples of alkynyloxy groups are ethynyloxy, propynyloxy, but-1-ynyloxy, but-2-ynyloxy and but-3-ynyloxy.

Alkoxyalkyl, as used herein, refers to a group R, substituted at any position with one or more groups —OR, wherein each R is, independently, alkyl as defined herein.

Alkoxyalkoxy, as used herein, refers to the group —OROR, wherein each R is, independently, an alkyl group as defined above.

Alkenyloxyalkyl, as used herein, refers to the group —ROR', wherein R is alkyl as used herein and R' is alkenyl as used herein.

Cyanoalkyl, as used herein, refers to an alkyl group substituted with one or more cyano groups.

Halogen, halide and halo, as used herein, refer to iodine, bromine, chlorine and fluorine.

Haloalkyl, as used herein, refers to an alkyl group as defined above wherein at least one hydrogen atom has been replaced with a halogen atom as defined above. Examples of haloalkyl groups include chloromethyl, dichloromethyl, trichloromethyl, fluoromethyl, difluoromethyl and trifluoromethyl. Preferred haloalkyl groups are fluoroalkyl groups {i.e. haloalkyl groups, containing fluorine as the only halogen). More highly preferred haloalkyl groups are perfluoroalkyl groups, i.e. alkyl groups wherein all the hydrogen atoms are replaced with fluorine atoms.

Haloalkenyl, as used herein, refers to an alkenyl group as defined above wherein at least one hydrogen atom has been replaced with a halogen atom as defined above.

Haloalkoxy, as used herein, refers to the group —OR, wherein R is haloalkyl as defined above.

Alkylthio, as used herein, refers to the group —SR, wherein R is an alkyl group as defined above. Alkylthio groups include, but are not limited to, methylthio, ethylthio, propylthio, tert-butylthio, and the like.

Alkylsulfinyl, as used herein, refers to the group —S(O)R, wherein R is an alkyl group as defined above.

Alkylsulfonyl, as used herein, refers to the group —S(O)$_2$R, wherein R is an alkyl group as defined above.

Alkylcarbonyloxy, as used herein, refers to the group —OC(O)R, wherein R is alkyl as defined herein.

Alkoxycarbonyloxy, as used herein, refers to the group —OC(O)OR, wherein R is an alkyl group as defined above. Examples of alkoxycarbonyloxy groups are methoxycarbonyloxy, ethoxycarbonyloxy, propoxycarbonyloxy, but-1-oxycarbonyloxy, but-2-oxycarbonyloxy and but-3-oxycarbonyloxy.

Hydroxy or hydroxyl, as used herein, refers to the group —OH.

Nitro, as used herein, refers to the group —$NO_2$.

Cyano, as used herein, refers to the group —CN.

Aryl, as used herein, refers to an unsaturated aromatic carbocyclic group of from 6 to 10 carbon atoms having a single ring (e. g., phenyl) or multiple condensed (fused) rings, at least one of which is aromatic (e.g., indanyl, naphthyl). Preferred aryl groups include phenyl, naphthyl and the like. Most preferably, an aryl group is a phenyl group.

Aryloxy, as used herein, refers to the group —O-aryl, wherein aryl is as defined above. Preferred aryloxy groups include phenoxy, naphthyloxy and the like.

Aryloxycarbonyloxy, as used herein, refers to the group —OC(O)O-aryl wherein aryl is a as defined above.

Arylalkyl, as used herein, refers to a group R—Ar, wherein R is alkyl as defined herein and Ar is aryl as defined herein. Arylalkyl groups may be substituted on the alkyl linker or on the ring. An example of an arylalkyl group is the benzyl group (—$CH_2C_6H_5$).

Heterocyclyl, as used herein, refers to a non-aromatic ring system containing 3 to 10 ring atoms, at least one ring heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyrrolidinyl, imidazolinyl, pyrazolidinyl, piperidyl, piperazinyl, quinuclidinyl, morpholinyl, together with unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

Heteroaryl, as used herein, refers to a ring system containing 5 to 10 ring atoms, 1 to 4 ring heteroatoms and consisting either of a single aromatic ring or of two or more fused rings, at least one of which is aromatic. Preferably, single rings will contain up to three and bicyclic systems up to four heteroatoms which will preferably be independently chosen from nitrogen, oxygen and sulfur. Examples of such groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. Examples of bicyclic groups are benzothiophenyl, benzimidazolyl, benzothiadiazolyl, quinolinyl, cinnolinyl, quinoxalinyl and pyrazolo[1,5-a]pyrimidinyl.

'Saturated ring', as used herein, refers to a ring system in which the atoms in the ring are linked by single bonds.

'Partially unsaturated ring', as used herein, refers to a ring system in which at least two atoms in the ring are linked by a double bond. Partially unsaturated ring systems do not include aromatic rings.

"Optionally substituted", as used herein, means the group referred to can be substituted at one or more positions by any one or any combination of the radicals listed thereafter. For most groups, one or more hydrogen atoms are replaced by the radicals listed thereafter. For halogenated groups, for example, haloalkyl groups, one or more halogen atoms are replaced by the radicals listed thereafter.

Suitable salts include those derived from alkali or alkaline earth metals and those derived from ammonia and amines. Preferred cations include sodium, potassium, magnesium, and ammonium cations of the formula $N^+(R^{19}R^{20}R^{21}R^{22})$ wherein $R^{19}$, $R^{20}$, $R^{21}$ and $R^{22}$ are independently selected from hydrogen, $C_1$-$C_6$ alkyl and $C_1$-$C_6$ hydroxyalkyl. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecylamine, or benzylamine. Amine salts are often preferred forms of the compounds of Formula I because they are water-soluble and lend themselves to the preparation of desirable aqueous based herbicidal compositions.

Acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety.

In another aspect the present invention provides intermediates useful in the preparation of compounds of the invention.

In one embodiment, there are provided intermediates of the formula (III) wherein X, $R^1$, $R^2$, $R^a$, $R^b$, $R^c$ and $R^d$ are as defined above.

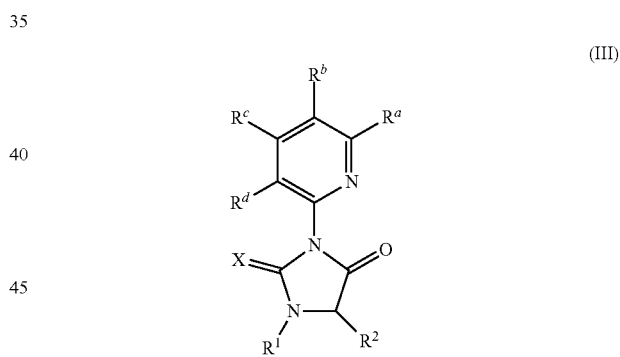

(III)

In another embodiment, there are provided intermediates shown below wherein X, $R^1$, $R^2$, $R^{14}$, $R^{15}$, $R^a$, $R^b$, $R^c$ and $R^d$ are as defined above.

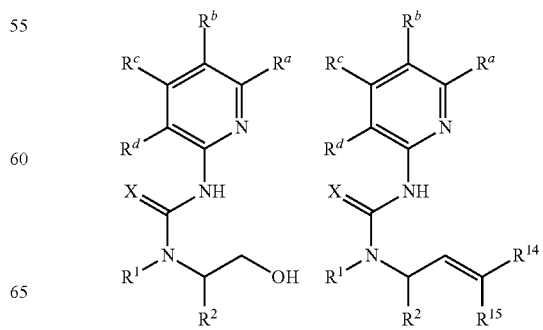

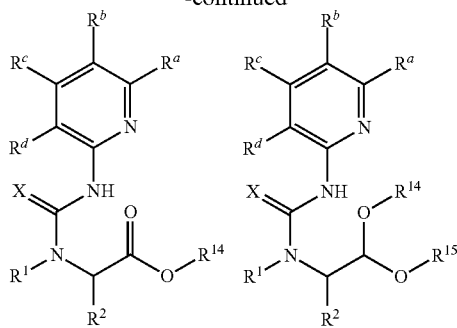

Compounds of the invention may be prepared by techniques known to the person skilled in the art of organic chemistry. General methods for the production of compounds of formula (I) are described below. Unless otherwise stated in the text, the substituents X, $R^1$, $R^2$, $R^3$, $R^a$, $R^b$, $R^c$ and $R^d$ are as defined hereinbefore. The starting materials used for the preparation of the compounds of the invention may be purchased from usual commercial suppliers or may be prepared by known methods. The starting materials as well as the intermediates may be purified before use in the next step by state of the art methodologies such as chromatography, crystallization, distillation and filtration.

For example, compounds of formula (IX) wherein $R^1$ is an alkyl or alkoxy group and $R^2$ is a hydrogen or alkyl group may be prepared by reaction of amino-pyridine (IV) with phenylchloroformate to give carbamate product (V). The subsequent reaction with an appropriately substituted amino-ester (VI) gives compounds of type (VII) and subsequent cyclisation gives compounds of type (VIII) and reduction with e.g. with sodium borohydride gives compounds of type (IX). The methyl amino-ester (VI) may also be replaced by other amino esters or amino-acids. Phenyl chloroformate may be replaced by other activating groups such as phosgene or para-nitrophenyl chloroformate. The cyclisation to (VIII) may occur in situ or require heating for carboxylic acids or esters or treatment with a reagent such as thionyl chloride for carboxylic acids. Compounds of type (VII) can be converted to compounds of type (IX) directly by treatment with a reducing reagent such as DIBAL-H or NaBH$_4$. Esters of type (VII) may also be reduced to their corresponding primary alcohols and then such alcohols can be re-oxidised to compounds of type (IX) with oxidants such as Dess-Martin periodinane.

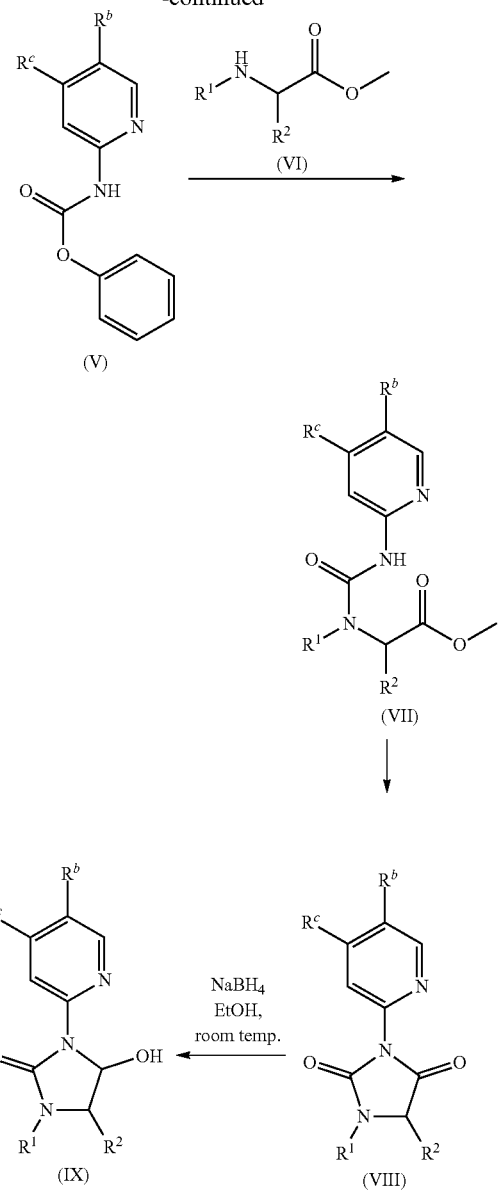

Alternatively, compounds of formula (IX) wherein $R^1$ is an alkyl group or alkoxy group and $R^2$ is a hydrogen or alkyl group may be prepared by Palladium catalysed reaction of chloro-pyridine (X) with urea (XI) to give (XII) (for a reference to a related reaction see WO2006048249, example 3.1) and then subsequent cyclisation gives compounds of type (IX).

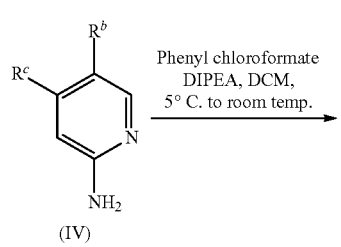

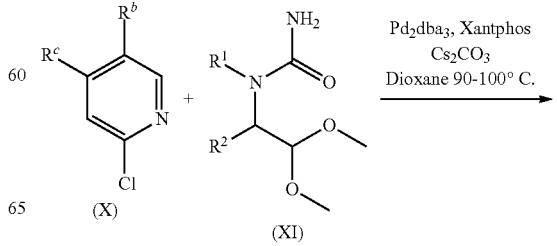

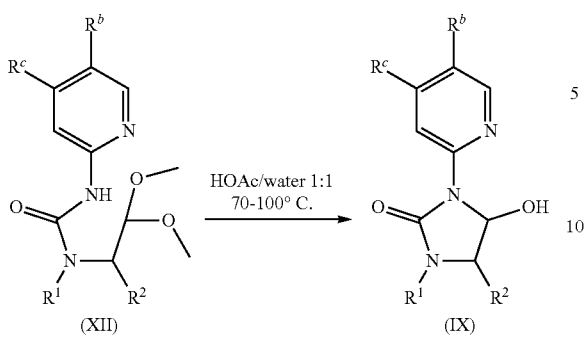

Urea (XI) may be formed by reaction of ester (XIII) with Grignard reagents, reductive amination of the product ketone (XIV) with amines and finally reaction of the subsequent product amine (XV) with TMS-isocyanate to give compounds of type (XI). Alternatively (XV) can be formed by a Grignard addition of type $R_2MgCl$ to appropriate imines. Alternatively, a nitrile can replace the ester group of (XIII) in the reaction with Grignard reagents.

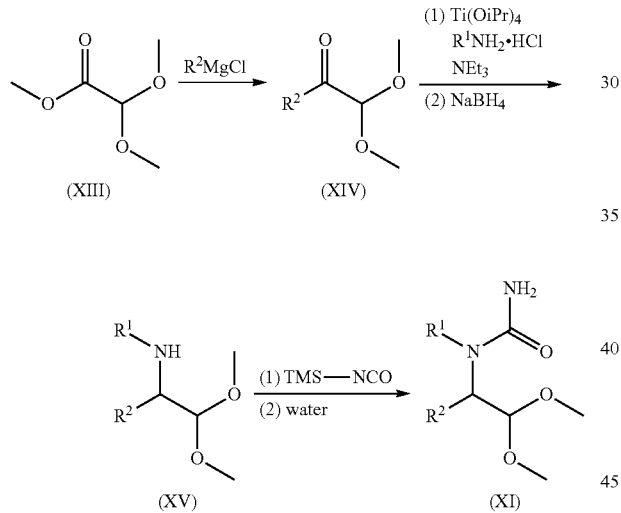

Alternatively, reaction of compounds of type (XIV) with methoxylamine following by reduction of the oxime ether formed gives compounds of type (XV) which can form compounds of type (XI) where $R^1$ is alkoxy. Alternatively, reaction of compounds of type (XIV) where $R^2$ is hydrogen with methoxylamine followe by addition of Grignard reagents to the formed oxime also can give compounds of type (XV).

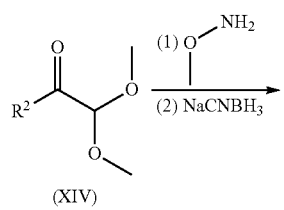

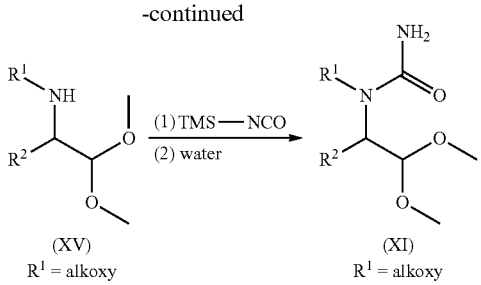

Compounds of formula (XVIII) wherein $R^2$ is an hydroxy group may be prepared by the Palladium catalysed reaction of chloro-pyridine (X) with urea (XVI) to give urea (XVII) (for a reference to a related reaction see WO2006048249, example 3.1), which can react with aqueous glyoxal solution to give product (XVIII). Compounds of formula (IX) where $R^2$ is an alkoxy group may be prepared by reacting compounds of formula (XVIII) with alcohols of type $R^4$—OH under acidic conditions.

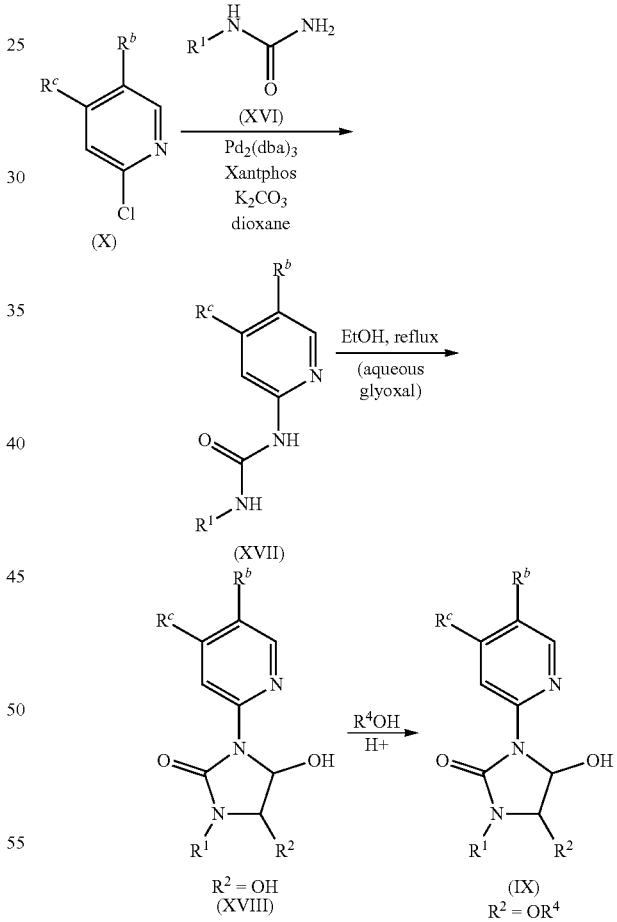

Alternatively, compounds of formula (V) may be reacted with compounds of formula (XIX) wherein $R^2$ is a hydrogen or alkyl group to give products of type (XX). Cyclisation with a suitable reagent such as thionyl chloride gives compounds of formula (XXI), which can be alkylated with a suitable base such as LiHMDS and a suitable alkylating agent such as methyl iodide (for $R^1$=Me) to give compound (VIII). Reduction as before gives compounds of type (IX).

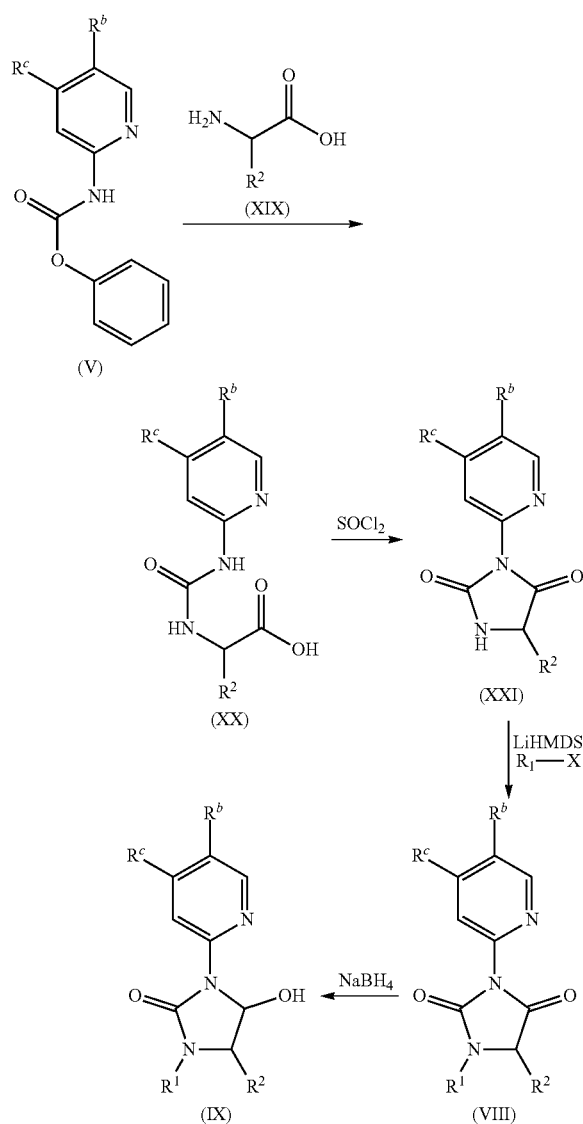

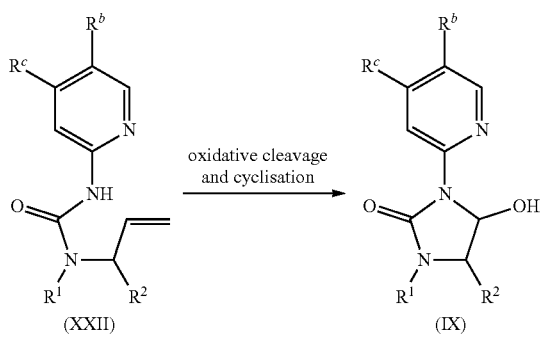

Alternatively oxidative cleavage (using ozonolysis or OsO$_4$/NaIO$_4$ or similar conditions) of an appropriate vinyl compound such as (XXII) or derivatives thereof and cyclisation could give the desired product.

Alternatively, compounds of type (XXIII) may be coupled with compounds of type (X) under Palladium catalysed conditions to give compounds of type (VIII) and then standard reduction with NaBH$_4$ for example gives products of type (IX).

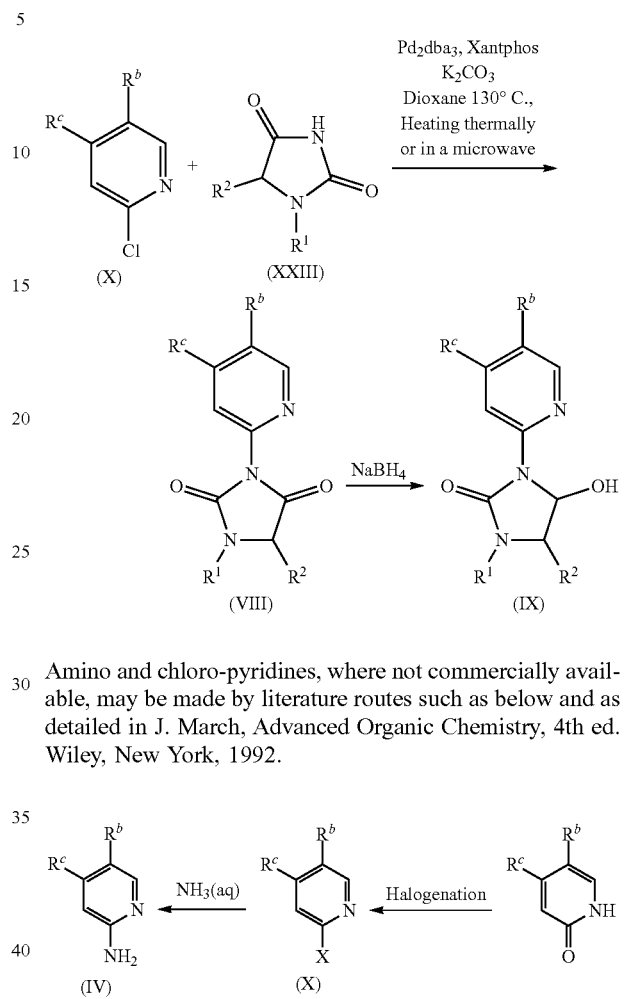

Amino and chloro-pyridines, where not commercially available, may be made by literature routes such as below and as detailed in J. March, Advanced Organic Chemistry, 4th ed. Wiley, New York, 1992.

Suitable conditions for effecting these transformations are set out in J. March, Advanced Organic Chemistry, 4th ed. Wiley, New York, 1992.

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. Therefore, the invention also relates to a herbicidal composition which comprises a herbicidally effective amount of a compound of formula (I) in addition to formulation adjuvants. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use.

The dilutions can be made, for example, with water, liquid fertilizers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydro-furfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallization inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say, without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%
The following Examples further illustrate, but do not limit, the invention.
Formulation Examples for Herbicides of Formula (I) (%=% by Weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. CaCO$_3$ or SiO$_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. CaCO$_3$ or SiO$_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention also provides a method of controlling plants which comprises applying to the plants or to the locus thereof a herbicidally effective amount of a compound of formula (I).

The invention also provides a method of inhibiting plant growth which comprises applying to the plants or to the locus thereof a herbicidally effective amount of a compound of formula (I).

The invention also provides a method of controlling weeds in crops of useful plants, comprising applying to said weeds or to the locus of said weeds, or to said useful plants or to the locus of said useful plants, a compound or a composition of the invention.

The invention also provides a method of selectively controlling grasses and/or weeds in crops of useful plants which comprises applying to the useful plants or locus thereof or to the area of cultivation a herbicidally effective amount of a compound of formula (I).

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation and includes not only areas where weeds may already be growing, but also areas where weeds have yet to emerge, and also to areas under cultivation with respect to crops of useful plants. "Areas under cultivation" include land on which the crop plants are already growing and land intended for cultivation with such crop plants. The term "weeds" as used herein means any undesired plant, and thus includes not only agronomically important weeds as described below, but also volunteer crop plants.

The compounds of the invention can be applied before or after planting of the crops, before weeds emerge (pre-emergence application) or after weeds emerge (post-emergence application), and are particularly effective when applied post-emergence to the weeds.

Crops of useful plants in which the composition according to the invention can be used include, but are not limited to, perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals, switchgrass, turf and vegetables, especially cereals, maize and soy beans.

The grasses and weeds to be controlled may be both monocotyledonous species, for example *Agrostis, Alopecurus, Avena, Brachiaria, Bromus, Cenchrus, Cyperus, Digitaria, Echinochloa, Eriochloa, Lolium, Monochoria, Panicum, Poa, Rottboellia, Sagittaria, Scirpus, Setaria, Sida* and *Sorghum*, and dicotyledonous species, for example *Abutilon, Amaranthus, Chenopodium, Chrysanthemum, Euphorbia, Galium, Ipomoea, Kochia, Nasturtium, Polygonum, Sida, Sinapis, Solanum, Stellaria, Veronica, Viola* and *Xanthium*.

In all aspects of the invention, in a particular embodiment, the weeds, e.g. to be controlled and/or growth-inhibited may be monocotyledonous or dicotyledonous weeds, which are tolerant or resistant to one or more other herbicides for example, HPPD inhibitor herbicides such as mesotrione, PSII inhibitor herbicides such as atrazine or EPSPS inhibitors such as glyphosate. Such weeds include, but are not limited to resistant *Amaranthus* biotypes.

Crops are to be understood as also including those crops which have been rendered tolerant to herbicides or classes of herbicides (e.g. auxins or ALS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®, respectively.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Any method of application to weeds/crop of useful plant, or locus thereof, which is routinely used in agriculture may be used, for example application by spray or broadcast method typically after suitable dilution of a compound of formula (I) (whether said compound is formulated and/or in combination with one or more further active ingredients and/or safeners, as described herein).

The compounds of formula (I) according to the invention can also be used in combination with other active ingredients, e.g. other herbicides, and/or insecticides, and/or acaricides, and/or nematocides, and/or molluscicides, and/or fungicides, and/or plant growth regulators. Such mixtures, and the use of such mixtures to control weeds and/or undesired plant growth, form yet further aspects of the invention. For the avoidance of doubt, mixtures of invention also include mixtures of two or more different compounds of formula (I). In particular, the present invention also relates to a composition of the invention which comprises at least one further herbicide in addition to the compound of formula (I).

When a compound of formula (I) is combined with at least one additional herbicide, the following mixtures of the compound of formula (I) are preferred. Compound of formula (I)+acetochlor, compound of formula (I)+acifluorfen, compound of formula (I)+acifluorfen-sodium, compound of formula (I)+aclonifen, compound of formula (I)+acrolein, compound of formula (I)+alachlor, compound of formula (I)+alloxydim, compound of formula (I)+allyl alcohol, compound of formula (I)+ametryn, compound of formula (I)+amicarbazone, compound of formula (I)+amidosulfuron, compound of formula (I)+aminocyclopyrachlor, compound of formula (I)+aminopyralid, compound of formula (I)+amitrole, compound of formula (I)+ammonium sulfamate, compound of formula (I)+anilofos, compound of formula (I)+asulam, compound of formula (I)+atrazine, formula (I)+aviglycine, formula (I)+azafenidin, compound of formula (I)+azimsulfuron, compound of formula (I)+BCPC, compound of formula (I)+beflubutamid, compound of formula (I)+benazolin, formula (I)+bencarbazone, compound of formula (I)+benfluralin, compound of formula (I)+benfuresate, compound of formula (I)+bensulfuron, compound of formula (I)+bensulfuron-methyl, compound of formula (I)+bensulide, compound of formula (I)+bentazone, compound of formula (I)+benzfendizone, compound of formula (I)+benzobicyclon, compound of formula (I)+benzofenap, compound of formula (I)+bicyclopyrone, compound of formula (I)+bifenox, compound of formula (I)+bilanafos, compound of formula (I)+bispyribac, compound of formula (I)+bispyribac-sodium, compound of formula (I)+borax, compound of formula (I)+bromacil, compound of formula (I)+bromobutide, formula (I)+bromophenoxim, compound of formula (I)+bromoxynil, compound of formula (I)+butachlor, compound of formula (I)+butafenacil, compound of formula (I)+butamifos, compound of formula (I)+butralin, compound of formula (I)+butroxydim, compound of formula (I)+butylate, compound of formula (I)+cacodylic acid, compound of formula (I)+calcium chlorate, compound of formula (I)+cafenstrole, compound of formula (I)+carbetamide, compound of formula (I)+carfentrazone, compound of formula (I)+carfentrazone-ethyl, compound of formula (I)+CDEA, compound of formula (I)+CEPC, compound of formula (I)+chlorflurenol, compound of formula (I)+chlorflurenol-methyl, compound of formula (I)+chloridazon, compound of formula (I)+chlorimuron, compound of formula (I)+chlorimuron-ethyl, compound of formula (I)+chloroacetic acid, compound of formula (I)+chlorotoluron, compound of formula (I)+chlorpropham, compound of formula (I)+chlorsulfuron, compound of formula (I)+chlorthal, compound of formula (I)+chlorthal-dimethyl, compound of formula (I)+cinidon-ethyl, compound of formula (I)+cinmethylin, compound of formula (I)+cinosulfuron, compound of formula (I)+cisanilide, compound of formula (I)+clethodim, compound of formula (I)+clodinafop, compound of formula (I)+clodinafop-propargyl, compound of formula (I)+clomazone, compound of formula (I)+clomeprop, compound of formula (I)+clopyralid, compound of formula (I)+cloransulam, compound of formula (I)+cloransulam-methyl, compound of formula (I)+CMA, compound of formula (I)+4-CPB, compound of formula (I)+CPMF, compound of formula (I)+4-CPP, compound of formula (I)+CPPC, compound of formula (I)+cresol, compound of formula (I)+cumyluron, compound of formula (I)+cyanamide, compound of formula (I)+cyanazine, compound of formula (I)+cycloate, compound of formula (I)+cyclosulfamuron, compound of formula (I)+cycloxydim, compound of formula (I)+cyhalofop, compound of formula (I)+cyhalofop-butyl, compound of formula (I)+2,4-D, compound of formula (I)+3,4-DA, compound of formula (I)+daimuron, compound of formula (I)+dalapon, compound of formula (I)+dazomet, compound of formula (I)+2,4-DB, compound of formula (I)+3,4-DB, compound of formula (I)+2,4-DEB, compound of formula (I)+desmedipham, formula (I)+desmetryn, compound of formula (I)+dicamba, compound of formula (I)+dichlobenil, compound of formula (I)+ortho-dichlorobenzene, compound of formula (I)+para-dichlorobenzene, compound of formula (I)+dichlorprop, compound of formula (I)+dichlorprop-P, compound of formula (I)+diclofop, compound of formula (I)+diclofop-methyl, compound of formula (I)+diclosulam, compound of formula (I)+difenzoquat, compound of formula (I)+difenzoquat metilsulfate, compound of formula (I)+diflufenican, compound of formula (I)+diflufenzopyr, compound of formula (I)+dimefuron, compound of formula (I)+dimepiperate, compound of formula (I)+dimethachlor, compound of formula (I)+dimethametryn, compound of formula (I)+dimethenamid, compound of formula (I)+dimethenamid-P, compound of formula (I)+dimethipin, compound of formula (I)+dimethylarsinic acid, compound of formula (I)+dinitramine, compound of formula (I)+dinoterb, compound of formula (I)+diphenamid, formula (I)+dipropetryn, compound of formula (I)+diquat, compound of formula (I)+diquat dibromide, compound of formula (I)+dithiopyr, compound of formula (I)+diuron, compound of formula (I)+DNOC, compound of formula (I)+3,4-DP, compound of formula (I)+DSMA, compound of formula (I)+EBEP, compound of formula (I)+endothal, compound of formula (I)+EPTC, compound of formula (I)+esprocarb, compound of formula (I)+ethalfluralin, compound of formula (I)+ethametsulfuron, compound of formula (I)+ethametsulfuron-methyl, formula (I)+ethephon, compound of formula (I)+ethofumesate, compound of formula (I)+ethoxyfen, compound of formula (I)+ethoxysulfuron, compound of formula (I)+etobenzanid, compound of formula (I)+fenoxaprop, compound of formula (I)+fenoxaprop-P, compound of formula (I)+fenoxaprop-ethyl, compound of formula (I)+fenoxaprop-P-ethyl, compound of formula (I)+fentrazamide, compound of formula (I)+ferrous sulfate, compound of formula (I)+flamprop-M, compound of formula (I)+flazasulfuron, compound of formula (I)+florasulam, compound of formula (I)+fluazifop, compound of formula (I)+fluazifop-butyl, compound of formula (I)+fluazifop-P, compound of formula (I)+fluazifop-P-butyl, formula (I)+fluazolate, compound of formula (I)+flucarbazone, compound of formula (I)+flucarbazone-sodium, compound of formula (I)+flucetosulfuron, compound of formula (I)+fluchloralin, compound of formula (I)+flufenacet, compound of formula (I)+flufenpyr, compound of formula (I)+flufenpyr-ethyl, formula (I)+flumetralin, compound of formula (I)+flumetsulam, compound of formula (I)+flumiclorac, compound of formula (I)+flumiclorac-pentyl, compound of formula (I)+flumioxazin, formula (I)+flumipropin, compound of formula (I)+fluometuron, compound of formula (I)+fluoroglycofen, compound of formula (I)+fluoroglycofen-ethyl, formula (I)+fluoxaprop, formula (I)+flupoxam, formula (I)+flupropacil, compound of formula (I)+flupropanate, compound of formula (I)+flupyrsulfuron, compound of formula (I)+flupyrsulfuron-methyl-sodium, compound of formula (I)+flurenol, compound of formula (I)+fluridone, compound of formula (I)+flurochloridone, compound of formula (I)+fluroxypyr, compound of formula (I)+flurtamone, compound of formula (I)+fluthiacet, compound of formula (I)+fluthiacet-methyl, compound of formula (I)+fomesafen, compound of formula (I)+foramsulfuron, compound of formula (I)+fosamine, compound of formula (I)+glufosinate, compound of formula (I)+glufosinate-ammonium, compound of formula (I)+glyphosate, compound of formula (I)+halauxifen, compound of formula (I)+halauxifen-methyl, compound of formula (I)+halosulfuron, compound of formula (I)+halosulfuron-methyl, compound of formula (I)+haloxyfop, compound of formula (I)+haloxyfop-P, compound of formula (I)+HC-252, compound of formula (I)+hexazinone, compound of formula (I)+imazamethabenz, compound of formula (I)+imazamethabenz-methyl, compound of formula (I)+imazamox, compound of formula (I)+imazapic, compound of formula (I)+imazapyr, compound of formula (I)+imazaquin, compound of formula (I)+imazethapyr, compound of formula (I)+imazosulfuron, compound of formula (I)+indanofan, compound of formula (I) and indaziflam, compound of formula (I)+iodomethane, compound of formula (I)+iodosulfuron, compound of formula (I)+iodosulfuron-methyl-sodium, compound of formula (I)+ioxynil, compound of formula (I) and ipfencarbazone, compound of formula (I)+isoproturon, compound of formula (I)+isouron, compound of formula (I)+isoxaben, compound of formula (I)+isoxachlortole, compound of formula (I)+isoxaflutole, formula (I)+isoxapyrifop, compound of formula (I)+karbutilate, compound of formula (I)+lactofen, compound of formula (I)+lenacil, compound of formula (I)+linuron, compound of formula (I)+MAA, compound of formula (I)+MAMA, compound of formula (I)+MCPA, compound of formula (I)+MCPA-thioethyl, compound of formula (I)+MCPB, compound of formula (I)+mecoprop, compound of formula (I)+mecoprop-P, compound of formula (I)+mefenacet, compound of formula (I)+mefluidide, compound of formula (I)+mesosulfuron, compound of formula (I)+mesosulfuron-methyl, compound of formula (I)+mesotrione, compound of formula (I)+metam, compound of formula (I)+metamifop, compound of formula (I)+metamitron, compound of formula (I)+metazachlor, compound of formula (I) and metazosulfuron, compound of formula (I)+methabenzthiazuron, formula (I)+methazole, a compound of formula (I) and methiozolin, compound of formula (I)+methylarsonic acid, compound of formula (I)+methyldymron, compound of formula (I)+methyl isothiocyanate, compound of formula (I)+metobenzuron, formula (I)+metobromuron, compound of formula (I)+metolachlor, compound of formula (I)+S-metolachlor, compound of formula (I)+metosulam, compound of formula (I)+metoxuron, compound of formula (I)+metribuzin, compound of formula (I)+metsulfuron, compound of formula (I)+metsulfuron-methyl, compound of formula (I)+MK-616, compound of formula (I)+molinate, compound of formula (I)+monolinuron, a compound of formula (I) and monosulfuron, a compound of formula (I) and monosulfuron-ester compound of formula (I)+MSMA, compound of formula (I)+naproanilide, compound of formula (I)+napropamide, compound of formula (I)+naptalam, formula (I)+NDA-402989, compound of formula (I)+neburon, compound of formula (I)+nicosulfuron, formula (I)+nipyraclofen, formula (I)+n-methyl glyphosate, compound of formula (I)+nonanoic acid, compound of formula (I)+norflurazon, compound of formula (I)+oleic acid (fatty acids), compound of formula (I)+orbencarb, compound of formula (I)+orthosulfamuron, compound of formula (I)+oryzalin, compound of formula (I)+oxadiargyl, compound of formula (I)+oxadiazon, compound of formula (I)+oxasulfuron, compound of formula (I)+oxaziclomefone, compound of formula (I)+oxyfluorfen, compound of formula (I)+paraquat, compound of formula (I)+paraquat dichloride, compound of formula (I)+pebulate, compound of formula (I)+pendimethalin, compound of formula (I)+penoxsulam, compound of formula (I)+pentachlorophenol, compound of formula (I)+pentanochlor, compound of formula (I)+pentoxazone, compound of formula (I)+pethoxamid, compound of formula (I)+petrolium oils, compound of formula (I)+phenmedipham, compound of formula (I)+phenmedipham-ethyl, compound of formula (I)+picloram, compound of formula (I)+picolinafen, compound of formula (I)+pinoxaden, compound of formula (I)+piperophos, compound of formula (I)+potassium arsenite, compound of formula (I)+potassium azide, compound of formula (I)+pretilachlor, compound of formula (I)+primisulfuron, compound of formula (I)+primisulfuron-methyl, compound of formula (I)+prodiamine, compound of formula (I)+profluazol, compound of formula (I)+profoxydim, formula (I)+prohexadione-calcium, compound of formula (I)+prometon, compound of formula (I)+prometryn, compound of formula (I)+propachlor, compound of formula (I)+propanil, compound of formula (I)+propaquizafop, compound of formula (I)+propazine, compound of formula (I)+propham, compound of formula (I)+propisochlor, compound of formula (I)+propoxycarbazone, compound of formula (I)+propoxycarbazone-sodium, compound of formula (I)+propyzamide, compound of formula (I)+prosulfocarb, compound of formula (I)+prosulfuron, compound of formula (I)+pyraclonil, compound of formula (I)+pyraflufen, compound of formula (I)+pyraflufen-ethyl, formula (I)+pyrasulfotole, compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyributicarb, compound of formula (I)+pyridafol, compound of formula (I)+pyridate, compound of formula (I)+pyriftalid, compound of formula (I)+pyriminobac, compound of formula (I)+pyriminobac-methyl, compound of formula (I)+pyrimisulfan, compound of formula (I)+pyrithiobac, compound of formula (I)+pyrithiobac-sodium, formula (I)+pyroxasulfone, formula (I)+pyroxulam, compound of formula (I)+quinclorac, compound of formula (I)+quinmerac, compound of formula (I)+quinoclamine, compound of formula (I)+quizalofop, compound of formula (I)+quizalofop-P, compound of formula (I)+quizalofop-ethyl, compound of formula (I)+quizalofop-P-ethyl, compound of formula (I)+rimsulfuron, compound of formula (I)+saflufenacil, compound of formula (I)+sethoxydim, compound of formula (I)+siduron, compound of formula (I)+simazine, compound of formula (I)+simetryn, compound of formula (I)+SMA, compound of formula (I)+sodium arsenite, compound of formula (I)+sodium azide, compound of formula (I)+sodium chlorate, compound of formula (I)+sulcotrione, compound of formula (I)+sulfentrazone, compound of formula (I)+sulfometuron, compound of formula (I)+sulfometuron-methyl, compound of formula (I)+sulfosate, compound of formula (I)+sulfosulfuron, compound of formula (I)+sulfuric acid, compound of formula (I)+tar oils, compound of formula (I)+2,3,6-TBA, compound of formula (I)+TCA, compound of formula (I)+TCA-sodium, formula (I)+tebutam, compound of formula (I)+tebuthiuron, formula (I)+tefuryltrione, compound of formula 1+tembotrione, compound of formula (I)+tepraloxydim, compound of formula (I)+terbacil, compound of formula (I)+terbumeton, compound of formula (I)+terbuthylazine, compound of formula (I)+terbutryn, compound of formula (I)+thenylchlor, compound of formula (I)+thiazafluron, compound of formula (I)+thiazopyr, compound of formula (I)+thifensulfuron, compound of formula (I)+thiencarbazone, compound of formula (I)+thifensulfuron-methyl, compound of formula (I)+thiobencarb, compound of formula (I)+tiocarbazil, compound of formula (I)+topramezone, compound of formula (I)+tralkoxydim, a compound of formula (I) and triafamone compound of formula (I)+triallate, compound of formula (I)+triasulfuron, compound of formula (I)+triaziflam, compound of formula (I)+tribenuron, compound of formula (I)+tribenuron-methyl, compound of formula (I)+tricamba, compound of formula (I)+triclopyr, compound of formula (I)+trietazine, compound of formula (I)+trifloxysulfuron, compound of formula (I)+trifloxysulfuron-sodium, compound of formula (I)+trifluralin, compound of formula (I)+triflusulfuron, compound of formula (I)+triflusulfuron-methyl, compound of formula (I)+trifop, compound of formula (I)+trifop-methyl, compound of formula (I)+trihydroxytriazine, compound of formula (I)+trinexapac-ethyl, compound of formula (I)+tritosulfuron, compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula (I)+2-[[8-chloro-3,4-dihydro-4-(4-methoxyphenyl)-3-oxo-2-quinoxalinyl]carbonyl-1,3-cyclohexanedione and the compound of formula (I)+VX-573.

In particular, the following mixtures are important:

mixtures of a compound of formula (I) with an acetanilide (e.g. compound of formula (I)+acetochlor, compound of formula (I)+dimethenamid, compound of formula (I)+metolachlor, compound of formula (I)+S-metolachlor, or compound of formula (I)+pretilachlor) or with other inhibitors of VLCFAE (e.g. compound of formula (I)+pyroxasulfone).

mixtures of a compound of formula (I) with an HPPD inhibitor (e.g. compound of formula (I)+isoxaflutole, compound of formula (I)+mesotrione, compound of formula (I)+pyrasulfotole, compound of formula (I)+sulcotrione, compound of formula (I)+tembotrione, compound of formula (I)+topramezone, compound of formula (I)+bicyclopyrone;

mixtures of a compound of formula (I) with a triazine (e.g. compound of formula (I)+atrazine, or compound of formula (I)+terbuthylazine); mixtures of a compound of formula (I) with glyphosate;

mixtures of a compound of formula (I) with glufosinate-ammonium;

mixtures of a compound of formula (I) with a PPO inhibitor (e.g. compound of formula (I)+acifluorfen-sodium, compound of formula (I)+butafenacil, compound of formula (I)+carfentrazone-ethyl, compound of formula (I)+cinidon-ethyl, compound of formula (I)+flumioxazin, compound of formula (I)+fomesafen, compound of formula (I)+lactofen, or compound of formula (I)+SYN 523 ([3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Whilst two-way mixtures of a compound of formula (I) and another herbicide are explicitly disclosed above, the skilled man will appreciate that the invention extends to three-way, and further multiple combinations comprising the above two-way mixtures. In particular, the invention extends to:

mixtures of a compound of formula (I) with a triazine and an HPPD inhibitor (e.g. compound of formula (I)+triazine+isoxaflutole, compound of formula (I)+triazine+mesotrione, compound of formula (I)+triazine+pyrasulfotole, compound of formula (I)+triazine+sulcotrione, compound of formula (I)+triazine+tembotrione, compound of formula (I)+triazine+topramezone, compound of formula (I)+triazine+bicyclopyrone;

mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+bicyclopyrone;

mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+bicyclopyrone; mixtures of a compound of formula (I) with a VLCFAE inhibitor and an HPPD inhibitor (e.g. compound of formula (I)+S-metolachlor+isoxaflutole, compound of formula (I)+S-metolachlor+mesotrione, compound of formula (I)+S-metolachlor+pyrasulfotole, compound of formula (I)+S-metolachlor+sulcotrione, compound of formula (I)+S-metolachlor+tembotrione, compound of formula (I)+S-metolachlor+topramezone, compound of formula (I)+S-metolachlor+bicyclopyrone, compound of formula (I)+acetochlor+isoxaflutole, compound of formula (I)+acetochlor+mesotrione, compound of formula (I)+acetochlor+pyrasulfotole, compound of formula (I)+acetochlor+sulcotrione, compound of formula (I)+acetochlor+tembotrione, compound of formula (I)+acetochlor+topramezone, compound of formula (I)+acetochlor+bicyclopyrone, compound of formula (I)+pyroxasulfone+isoxaflutole, compound of formula (I)+pyroxasulfone+mesotrione, compound of formula (I)+pyroxasulfone+pyrasulfotole, compound of formula (I)+pyroxasulfone+sulcotrione, compound of formula (I)+pyroxasulfone+tembotrione, compound of formula (I)+pyroxasulfone+topramezone, compound of formula (I)+pyroxasulfone+bicyclopyrone, compound of formula (I)+S-metolachlor+mesotrione+bicyclopyrone.

mixtures of a compound of formula (I) with glyphosate and a VLCFAE inhibitor (e.g. compound of formula (I)+glyphosate+S-metolachlor, compound of formula (I)+glyphosate+acetochlor, compound of formula (I)+glyphosate+pyroxasulfone).

Particularly preferred are mixtures of the compound of formula (I) with mesotrione, bicyclopyrone, isoxaflutole, tembotrione, topramezone, sulcotrione, pyrasulfotole, metolachlor, S-metolachlor, acetochlor, pyroxasulfone, P-dimethenamid, dimethenamid, flufenacet, pethoxamid, atrazine, terbuthylazine, bromoxynil, metribuzin, amicarbazone, bentazone, ametryn, hexazinone, diuron, tebuthiuron, glyphosate, paraquat, diquat, glufosinate, acifluorfen-sodium, butafenacil, carfentrazone-ethyl, cinidon-ethyl, flumioxazin, fomesafen, lactofen, [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester.

The mixing partners of the compound of formula (I) may also be in the form of esters or salts, as mentioned e.g. in The Pesticide Manual, 14th Edition (BCPC), 2006. The reference to acifluorfen-sodium also applies to acifluorfen, the reference to dimethenamid also applies to dimethenamid-P, the reference to glufosinate-ammonium also applies to glufosinate, the reference to bensulfuron-methyl also applies to bensulfuron, the reference to cloransulam-methyl also applies to cloransulam, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further active ingredients, in particular with one or more further herbicides, can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. Where a compound of formula (I) is combined with a safener, the following combinations of the compound of formula (I) and the safener are particularly preferred. Compound of formula (I)+AD 67 (MON 4660), compound of formula (I)+benoxacor, compound of formula (I)+cloquintocet-mexyl, compound of formula (I)+cyometrinil and a compound of formula (I)+the corresponding (Z) isomer of cyometrinil, compound of formula (I)+cyprosulfamide (CAS RN 221667-31-8), compound of formula (I)+dichlormid, compound of formula (I) and dicyclonon, compound of formula (I) and dietholate, compound of formula (I)+fenchlorazole-ethyl, compound of formula (I)+fenclorim, compound of formula (I)+flurazole, compound of formula (I)+fluxofenim, compound of formula (I)+furilazole and a compound of formula (I)+the corresponding R isomer or furilazome, compound of formula (I)+isoxadifen-ethyl, compound of formula (I)+mefenpyr-diethyl, compound of formula (I) and mephenate, compound of formula (I)+oxabetrinil, compound of formula (I)+naphthalic anhydride (CAS RN 81-84-5), compound of formula (I) and TI-35, compound of formula (I)+N-isopropyl-4-(2-methoxy-benzoylsulfamoyl)-benzamide (CAS RN 221668-34-4) and a compound of formula (I)+N-(2-methoxybenzoyl)-4-[(methylaminocarbonyl)amino]benzenesulfonamide. Particularly preferred are mixtures of a compound of formula (I) with benoxacor, a compound of formula (I) with cloquintocet-mexyl, a compound of formula (I)+cyprosulfamide and a compound of formula (I) with N-(2-methoxybenzoyl)-4-[(methylaminocarbonyl)amino]benzenesulfonamide.

The safeners of the compound of formula (I) may also be in the form of esters or salts, as mentioned e.g. in The Pesticide Manual, 14th Edition (BCPC), 2006. The reference to cloquintocet-mexyl also applies to cloquintocet and to a lithium, sodium, potassium, calcium, magnesium, aluminium, iron, ammonium, quaternary ammonium, sulfonium or phosphonium salt thereof as disclosed in WO02/34048 and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) and any further active ingredient, in particular a further herbicide, with the safener).

It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with tembotrione and a safener.

Mixtures of a compound of formula (I) with topramezone and a safener.

Mixtures of a compound of formula (I) with bicyclopyrone and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with a triazine and tembotrione and a safener.

Mixtures of a compound of formula (I) with a triazine and topramezone and a safener.

Mixtures of a compound of formula (I) with a triazine and bicyclopyrone and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glyphosate and tembotrione and a safener.

Mixtures of a compound of formula (I) with glyphosate and topramezone and a safener.

Mixtures of a compound of formula (I) with glyphosate and bicyclopyrone and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with glufosinate-ammonium and tembotrione and a safener.

Mixtures of a compound of formula (I) with glufosinate-ammonium and topramezone and a safener.

Mixtures of a compound of formula (I) with glufosinate-ammonium and bicyclopyrone and a safener.

Mixtures of a compound of formula (I) with S-metolachlor and a safener.

Mixtures of a compound of formula (I) with S-metolachlor and isoxaflutole and a safener.

Mixtures of a compound of formula (I) with S-metolachlor and mesotrione and a safener.

Mixtures of a compound of formula (I) with S-metolachlor and sulcotrione and a safener.

Mixtures of a compound of formula (I) with S-metolachlor and tembotrione and a safener.

Mixtures of a compound of formula (I) with S-metolachlor and topramezone and a safener.

Mixtures of a compound of formula (I) with S-metolachlor and bicyclopyrone and a safener Mixtures of a compound of formula (I) with pyroxasulfone and a safener.

Mixtures of a compound of formula (I) with pyroxasulfone and isoxaflutole and a safener.

Mixtures of a compound of formula (I) with pyroxasulfone and mesotrione and a safener.

Mixtures of a compound of formula (I) with pyroxasulfone and sulcotrione and a safener.

Mixtures of a compound of formula (I) with pyroxasulfone and tembotrione and a safener.

Mixtures of a compound of formula (I) with pyroxasulfone and topramezone and a safener.

Mixtures of a compound of formula (I) with pyroxasulfone and bicyclopyrone and a safener Mixtures of a compound of formula (I) with acetochlor and a safener.

Mixtures of a compound of formula (I) with acetochlor and isoxaflutole and a safener.

Mixtures of a compound of formula (I) with acetochlor and mesotrione and a safener.

Mixtures of a compound of formula (I) with acetochlor and sulcotrione and a safener.

Mixtures of a compound of formula (I) with acetochlor and tembotrione and a safener.

Mixtures of a compound of formula (I) with acetochlor and topramezone and a safener.

Mixtures of a compound of formula (I) with acetochlor and bicyclopyrone and a safener.

Mixtures of a compound of formula (I) with S-metolachlor and mesotrione and bicyclopyrone and a safener.

Mixtures of a compound of formula (I) with S-metolachlor and a triazine and mesotrione and bicyclopyrone and a safener.

Various aspects and embodiments of the present invention will now be illustrated in more detail by way of example. It will be appreciated that modification of detail may be made without departing from the scope of the invention.

For the avoidance of doubt, where a literary reference, patent application, or patent, is cited within the text of this application, the entire text of said citation is herein incorporated by reference.

EXAMPLES

Preparation Examples

The following abbreviations were used in this section: s=singlet; bs=broad singlet; d=doublet; dd=double doublet; dt=double triplet; t=triplet, tt=triple triplet, q=quartet, sept=septet; m=multiplet; RT=retention time, MH⁻=molecular mass of the molecular cation.

1H NMR spectra were recorded at 400 MHz either on a Varian Unity Inova instrument 400 MHz or on a Bruker AVANCE-II instrument.

The compounds may exist in a mixture of diastereoisomers, which may be observed by LC-MS and NMR. The stereochemistry of the chiral centre at the carbon containing the $R_3$ group was generally found to interconvert at room temperature when $R^3$ is hydroxyl. Depending on the nature of $R^2$ substitution and the conditions for product synthesis, purification and analysis the ratio of diastereomers may change.

Example 1—Preparation of 5-hydroxy-1-[5-iodo-4-(trifluoromethyl)-2-pyridyl]-3,4-dimethyl-imidazolidin-2-one (A25)

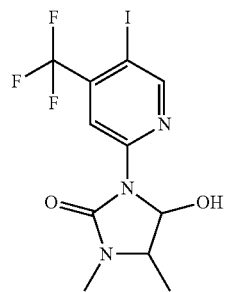 [SMILES: CC1C(O)N(c2cc(C(F)(F)F)c(I)cn2)C(=O)N1C]

Procedure for Synthesis of 1-(2,2-dimethoxy-1-methyl-ethyl)-3-[5-iodo-4-(trifluoromethyl)-2-pyridyl]-1-methyl-urea (Step-1)

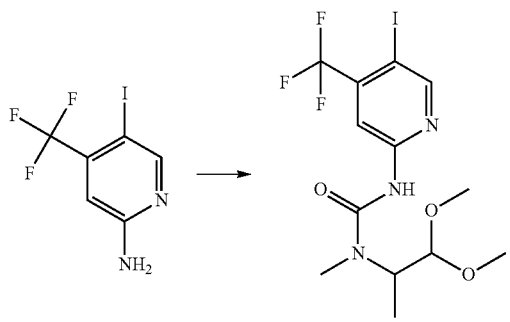 [SMILES: Nc1cc(C(F)(F)F)c(I)cn1 ; COC(OC)C(C)N(C)C(=O)Nc1cc(C(F)(F)F)c(I)cn1]

5-iodo-4-(trifluoromethyl)pyridin-2-amine (for a synthesis see Bioorganic & Medicinal Chemistry Letters, 1994, 4(6), 835-8) (0.500 g, 1.74 mmol) was dissolved in DCM (5 mL) and then carbonyl-diimidazole (1.06 g, 80% purity) was added. The reaction mixture was heated at 105° C. in a microwave vial for 15 minutes and then cooled to 10° C. 1,1-dimethoxy-N-methyl-propan-2-amine (preparation as in example 13) (695 mg, 3 equiv.) was added and the reaction was stirred at room temperature for 15 mins. The reaction was diluted with DCM (10 mL) and water (5 mL) was added. This mixture was filtered and the aqueous layer extracted with further DCM (2×10 mL). The combined organics were dried ($Na_2SO_4$), filtered and evaporated and then chromatographed on silica eluting with 20-30% EtOAc in isohexane. Fractions containing product were evaporated to give desired product as an amber gum (326 mg, 42%).

LC-MS: (positive ES MH+ 448).

Procedure for Synthesis of 5-hydroxy-1-[5-iodo-4-(trifluoromethyl)-2-pyridyl]-3,4-dimethyl-imidazolidin-2-one (Step-2)

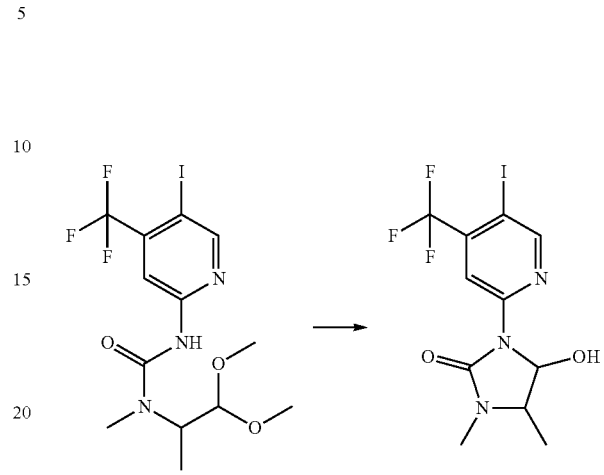

1-(2,2-dimethoxy-1-methyl-ethyl)-3-[5-iodo-4-(trifluoromethyl)-2-pyridyl]-1-methyl-urea (260 mg, 0.581 mmol) was dissolved in acetic acid (5.2 mL) and water (2.6 mL). The reaction mixture was stirred at room temperature for 2 days. The reaction mixture was then evaporated and dried (100 to 1 mBar at 20-35° C.) for 2 h to remove traces of acetic acid to give product as a lilac gum which crystallised to give a solid (230 mg, 98%).

LC-MS: (positive ES MH+ 402).

$^1$H NMR ($CDCl_3$): Major diastereomer: 8.69 (s, 1H), 8.64 (s, 1H), 5.56 (m, 1H), 4.65 (very br s, 1H), 3.53 (m, 1H), 2.93 (s, 3H), 1.33 (d, 3H).

Minor diastereomer: 8.70 (s, 1H), 8.64 (s, 1H), 5.91 (d, 1H), 4.65 (very br s, 1H), 3.76 (m, 1H), 2.88 (s, 3H), 1.38 (d, 3H).

Example 2—Preparation of 5-hydroxy-1-[5-(4-methoxy-3-pyridyl)-4-(trifluoromethyl)-2-pyridyl]-3,4-dimethyl-imidazolidin-2-one (A24)

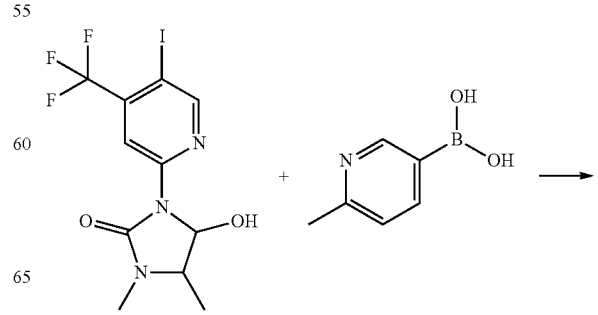

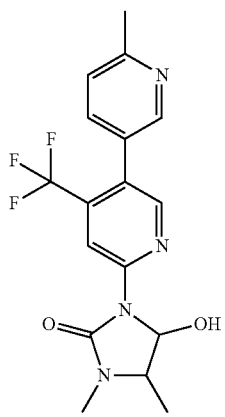

5-hydroxy-1-[5-iodo-4-(trifluoromethyl)-2-pyridyl]-3,4-dimethyl-imidazolidin-2-one (50 mg, 1 equiv. 0.125 mmol), (6-methyl-3-pyridyl)boronic acid (22 mg, 1.1 equiv.), tricyclohexylphosphine (4 mg, 0.12 equiv.) tris(dibenzylideneacetone)dipalladium(0) (6 mg, 0.05 equiv.), in 1,4-dioxane (0.5 mL) was treated with $K_2CO_3$ (38 mg) in water (0.2 mL). The reaction was heated for 80 minutes at 100° C., then treated with further 6-methyl-3-pyridyl)boronic acid (2.2 equiv.), tricyclohexyl phosphine (4 mg, 0.12 equiv.), tris(dibenzylideneacetone)dipalladium(0) (6 mg, 0.05 equiv), $K_3PO_4$ (45 mg, 1.7 equiv.) and the reaction was then heated for a further 75 minutes at 100° C. The reaction mixture was diluted with EtOAc (6 mL) then filtered through celite, evaporated, then chromatographed on silica eluting with 20-100% EtOAc in isohexane. Fractions containing product were evaporated to give desired product as an amber gum (35 mg, 69%).

LC-MS: (positive ES MH+ 367).

$^1$H NMR (CDCl$_3$): Major diastereomer: 8.69 (s, 1H), 8.46 (s, 1H), 8.21 (m, 1H), 7.57 (dm, 1H), 7.25 (dm, 1H), 5.65 (m, 1H), 4.91 (br s, 1H), 3.56 (m, 1H), 2.95 (s, 3H), 2.64 (s, 3H), 1.36 (d, 3H).

Minor diastereomer: 8.69 (s, 1H), 8.46 (s, 1H), 8.21 (m, 1H), 7.57 (dm, 1H), 7.25 (dm, 1H), 6.00 (d, 1H), 4.78 (br s, 1H), 3.79 (m, 1H), 2.92 (s, 3H), 2.64 (s, 3H), 1.42 (d, 3H).

Example 3—Preparation of 5-hydroxy-1-[5-methoxy-4-(trifluoromethyl)-2-pyridyl]-3,4-dimethyl-imidazolidin-2-one (A12)

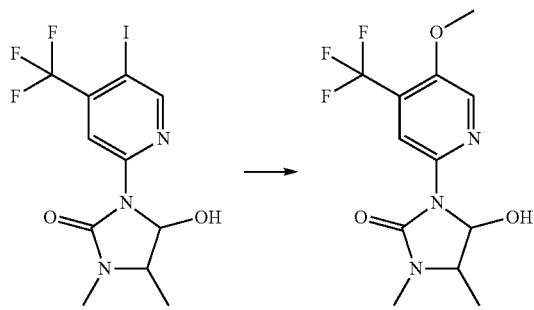 [SMILES: CC1C(O)N(c2cc(C(F)(F)F)c(I)cn2)C(=O)N1C ; COc1cnc(N2C(=O)N(C)C(C)C2O)cc1C(F)(F)F]

A mixture of di-tert-butyl-[6-methoxy-3-methyl-2-(2,4,6-triisopropylphenyl)phenyl]phosphane (RockPhos) (11 mg, 4.5 mol %), allylpalladium(II) chloride dimer (3 mg, 1.5 mol %) and Cs$_2$CO$_3$ (245 mg, 1.5 equiv.) in toluene (0.8 mL) was degassed by bubbling N$_2$ through the reaction mixture for 5 mins. This mixture was then heated to 90° C. for 3 mins then methanol (101 µL, 5 equiv.) was added, followed by 5-hydroxy-1-[5-iodo-4-(trifluoromethyl)-2-pyridyl]-3,4-dimethyl-imidazolidin-2-one (200 mg, 0.499 mmol, 1 equiv.). The reaction was then heated in a sealed tube at 80° C. for 1 h and 25 minutes. Further di-tert-butyl-[6-methoxy-3-methyl-2-(2,4,6-triisopropylphenyl)phenyl]phosphane (RockPhos) (11 mg, 4.5 mol %), allylpalladium(II) chloride dimer (3 mg, 1.5 mol %) and methanol (40 µL, 2 equiv.) was added. The reaction was then heated in a sealed tube at 80° C. for a further 1 h. The reaction mixture was diluted with 4 ml EtOAc, filtered through celite, then evaporated, then chromatographed on silica eluting with 0-100% EtOAc in isohexane. Fractions containing product were evaporated to give desired product as a pale yellow solid (80 mg, 53%).

LC-MS: (positive ES MH+ 306).

$^1$H NMR (CDCl$_3$): Major diastereomer: 8.45 (s, 1H), 8.03 (s, 1H), 5.53 (m, 1H), 4.90 (br s, 1H), 3.95 (s, 3H), 3.50 (m, 1H), 2.91 (s, 3H), 1.33 (d, 3H).

Minor diastereomer: 8.44 (s, 1H), 8.05 (s, 1H), 5.88 (d, 1H), 4.75 (br s, 1H), 3.95 (s, 3H), 3.75 (m, 1H), 2.88 (s, 3H), 1.39 (d, 3H).

Example 4—Preparation of 4-hydroxy-1-methoxy-5-methyl-3-[4-(trifluoromethyl)-2-pyridyl]imidazolidin-2-one (A8)

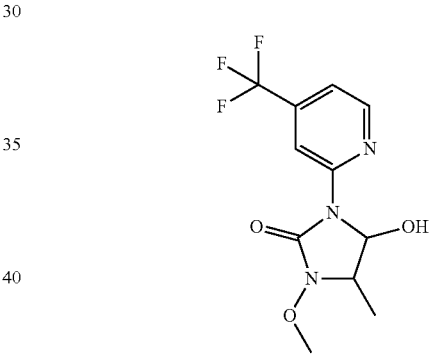

Procedure for Synthesis of N,1,1-trimethoxypropan-2-imine (Step-1)

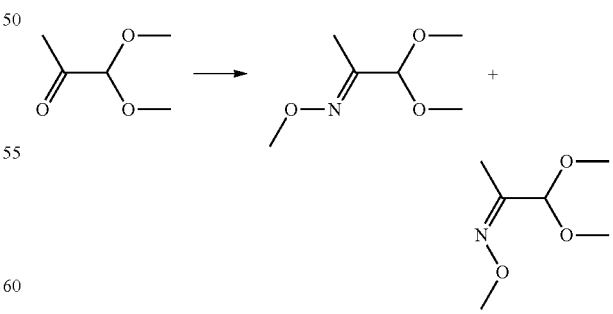

Methoxylamine hydrochloride (21.2 g) was suspended in methanol (65 mL) then potassium acetate (50.4 g, quickly ground in pestle and mortar to break up lumps) was added all at once and the thick white suspension resulting was stirred at room temp for 15 mins then cooled to 15° C. and then 1,1-dimethoxypropan-2-one (30 g) was added slowly over 25 mins. The reaction was stirred at room temperature for 50 mins and then diluted with 200 ml DCM, then 100 ml sat. NaHCO₃ (aq) was added cautiously over 15 mins. After effervescence subsided, the layers were separated, extracted with further DCM (2×80 mL), dried Na₂SO₄, filtered and concentrated at 220 mbar and 35° C. (care as desired product is volatile) to give 37 g amber liquid, which was used without further purification.

¹H NMR (CDCl₃) showed a 3:1 ratio of E:Z isomers.

Procedure for Synthesis of
N,1,1-trimethoxypropan-2-amine (Step-2)

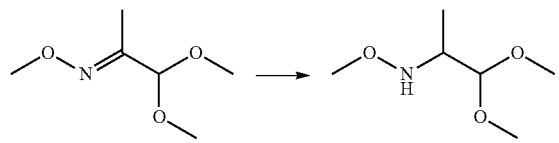

N,1,1-trimethoxypropan-2-imine (20 g) was dissolved in acetic acid (80 mL) then was cooled to 13° C. NaBH₃CN (9.82 g) was added portionwise over 10 mins. After 18 hrs at room temperature, the reaction was concentrated to remove bulk of HOAc then residue dissolved in DCM (300 mL) and satd. NaHCO₃ (aq) (300 mL) was added slowly with stirring. The mixture was stirred at rt for 90 mins, and then 40% NaOH(aq) was added until the solution reached pH 12. The layers were separated, extracted with further DCM (3×100 mL). The combined DCM layers were dried (Na₂SO₄), filtered and evaporated to give 16.4 g of crude product as a pale amber oil, which was further purified by Kugelrohr distillation (120° C. at 70 mBar) to give product (12.0 g, 59% yield) which was approximately 95% pure by NMR and used without further purification.

Procedure for Synthesis of 1-(2,2-dimethoxy-1-methyl-ethyl)-1-methoxy-urea (Step-3)

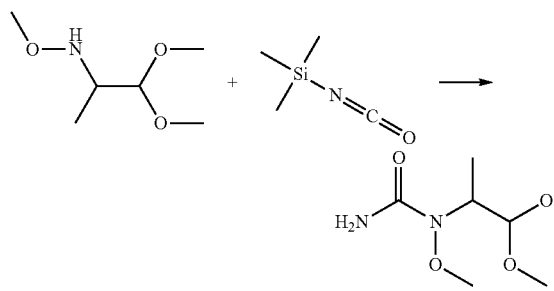

N,1,1-trimethoxypropan-2-amine (2.000 g, 13.41 mmol) was dissolved in IPA (5 mL) and the mixture was cooled to 0° C. under N₂, then trimethylsilyl isocyanate (commercially available) (4.83 mL, 33.51 mmol) was added and the reaction was allowed to warm to room temperature and was stirred at room temperature for 24 h. The reaction mixture was worked up by adding DCM (30 mL) and water (15 mL), extracting with further DCM (2×15 mL), dried (Na₂SO₄), filtered and evaporated then chromatographed on silica eluting with 50-100% EtOAc in isohexane. Fractions containing product were evaporated to give the desired product as a white solid (2.08 g, 81% yield). ¹H NMR (CDCl₃): 5.36 (br s, 2H), 4.47 (d, 1H), 4.32 (pentet, 1H), 3.75 (s, 3H), 3.37 (d, 6H), 1.24 (d, 3H).

Procedure for Synthesis of 1-(2,2-dimethoxy-1-methyl-ethyl)-1-methoxy-3-[4-(trifluoromethyl)-2-pyridyl]urea (Step-4)

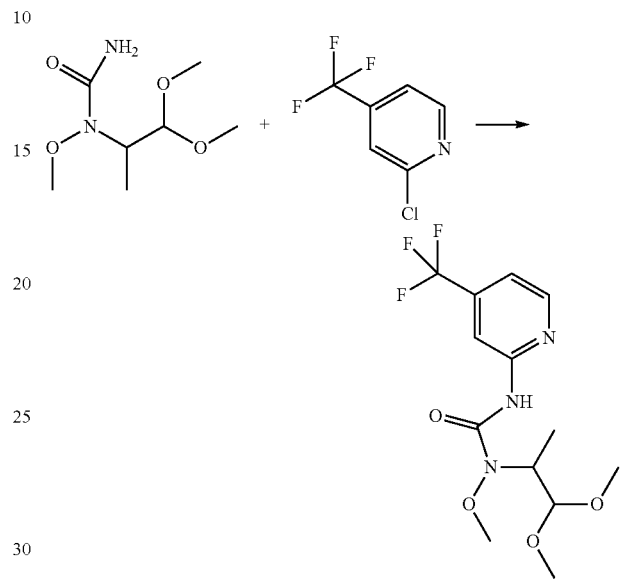

1-(2,2-dimethoxy-1-methyl-ethyl)-1-methoxy-urea (300 mg, 1.56 mmol), 2-chloro-4-(trifluoromethyl)pyridine (commercially available) (312 mg, 1.1 equiv.), potassium carbonate (324 mg), tris(dibenzylideneacetone)dipalladium(0) (30 mg), 4,5-bis(diphenylphosphino)-9,9-dimethylxanthene (70 mg) were suspended in 1-4-dioxane (4 mL) and the mixture was then heated at 105° C. in a sealed vial for 2 h. The mixture was allowed to cool to room temperature, diluted with EtOAc (6 mL), filtered, then chromatographed on silica eluting with 0-100% EtOAc in isohexane. Fractions containing product were evaporated to give the desired product as a yellow gum (170 mg, 32%).

LC-MS: (positive ES MH+ 338).

Procedure for Synthesis of 4-hydroxy-1-methoxy-5-methyl-3-[4-(trifluoromethyl)-2-pyridyl]imidazolidin-2-one (Step-5)

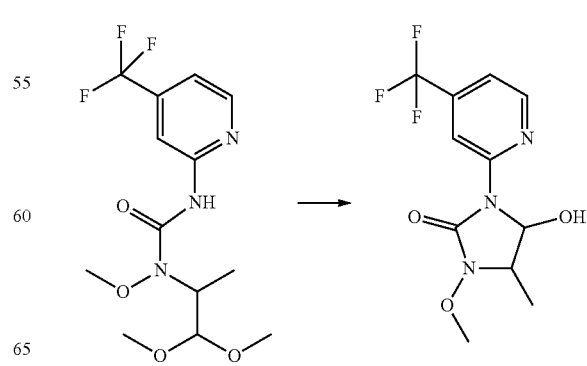

1-(2,2-dimethoxy-1-methyl-ethyl)-1-methoxy-3-[4-(trifluoromethyl)-2-pyridyl]urea (155 mg, 0.459 mmol) was dissolved in acetic acid (1 mL) and water (0.5 mL) and stirred at room temperature for 25 mins and then at 60° C. for 2 h and 45 mins. The reaction was left at room temperature for 18 h before heating again at 60° C. for 2 h. Reaction mixture was evaporated and then chromatographed on silica eluting with 0-24% EtOAc in isohexane. Fractions containing product were evaporated to give the desired product as a pale beige solid (101 mg, 75%).

NMR indicated a ratio of diastereoisomers in approximately a 2:1 ratio.

$^1$H NMR (CDCl$_3$): Major diastereomer: 8.55 (s, 1H), 8.43 (dd, 1H), 7.25 (d, 1H), 5.55 (m, 1H), 5.04 (very br s, 1H), 3.90 (s, 3H), 3.71 (m, 1H), 1.45 (d, 3H).

$^1$H NMR (CDCl$_3$): Minor diastereomer: 8.53 (s, 1H), 8.45 (dd, 1H), 7.24 (d, 1H), 5.87 (d, 1H), 4.60 (very br s, 1H), 3.93 (s, 3H), 3.80 (m, 1H), 1.50 (d, 3H).

LC-MS: (positive ES MH+ 292).

The diastereomeric ratio was found to vary according to conditions for product synthesis, purification and analysis. The stereochemistry of the chiral centre at the carbon containing the hydroxyl group was found to interconvert at room temperature.

Example 5—Preparation of 4-hydroxy-1-methoxy-5-methyl-3-[4-(trifluoromethyl)-2-pyridyl]imidazolidin-2-one (A8)—Alternative Synthesis

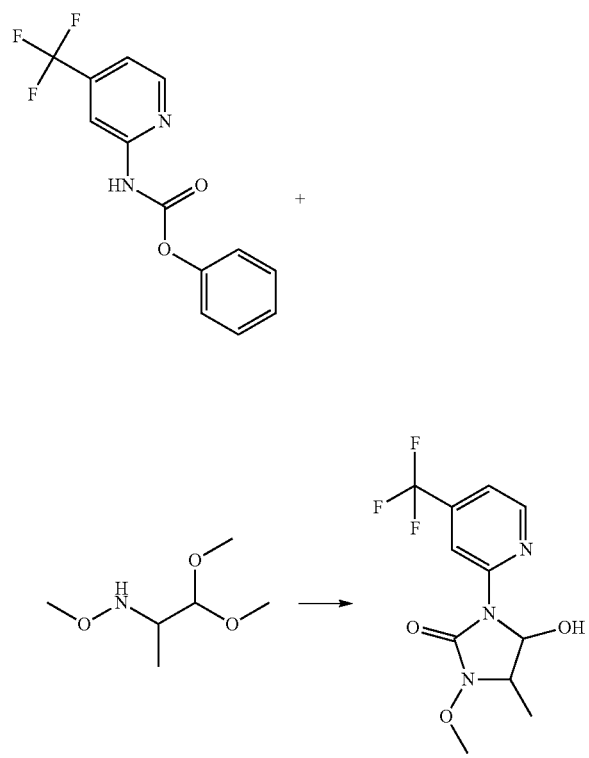

Phenyl N-[4-(trifluoromethyl)-2-pyridyl]carbamate (for a synthesis see WO 2007004749) (9.93 g, 1.05 equiv.) was suspended in 1,4-dioxane (25 mL) under a Nitrogen atmosphere and treated with N,1,1-trimethoxypropan-2-amine (5.00 g, 22.51 mmol, 1 equiv.) and the reaction was heated to reflux for 2.5 h. The reaction was cooled to room temperature, then 2N aqueous HCl (30 mL) was added to the reaction mixture and heated to 50° C. for 25 minutes. EtOAc (100 mL) and water (75 mL) was added and the aqueous layer was further extracted EtOAc (2×75 mL). The combined organic fractions were washed with satd NaHCO$_3$ (aq), dried (Na$_2$SO$_4$), filtered and then chromatographed on silica eluting with 0-26% EtOAc in isohexane. Fractions containing product were evaporated to give the desired product as a crystalline solid (6.865 g).

LC-MS: (positive ES MH+ 292).

NMR and LC-MS data for A3 and A4 were consistant with A8 (example 4).

The diastereomeric ratio was found to vary according to conditions for product synthesis, purification and analysis. The stereochemistry of the chiral centre at the carbon containing the hydroxyl group was found to interconvert at room temperature.

Example 6—Preparation of (4R,5S)-4-hydroxy-1-methoxy-5-methyl-3-[4-(trifluoromethyl)-2-pyridyl] imidazolidin-2-one and (4S,5S)-4-hydroxy-1-methoxy-5-methyl-3-[4-(trifluoromethyl)-2-pyridyl] imidazolidin-2-one (A3) and Example 7—(4R,5R)-4-hydroxy-1-methoxy-5-methyl-3-[4-(trifluoromethyl)-2-pyridyl]imidazolidin-2-one and (4S,5R)-4-hydroxy-1-methoxy-5-methyl-3-[4-(trifluoromethyl)-2-pyridyl] imidazolidin-2-one (A4)

A sample of compound A8 was separated into two major fractions by preparative chiral SFC (Lux Cellulose-4 column, eluting with IPA (7%) with other fractions discarded. The analysis could be performed by HPLC on a Lux Amylose-2 or WHELK-01 column eluting with heptane/IPA in a 70/30 ratio.

One fraction eluting from the SFC column was found to equilibrate to (4R,5R)-4-hydroxy-1-methoxy-5-methyl-3-[4-(trifluoromethyl)-2-pyridyl]imidazolidin-2-one and (4S,5R)-4-hydroxy-1-methoxy-5-methyl-3-[4-(trifluoromethyl)-2-pyridyl]imidazolidin-2-one.

The absolute stereochemistry may be proven by synthesis (in an analogous way to example 8-alternative synthesis below).

Another fraction eluting from the SFC column was found to equilibrate to (4R,5S)-4-hydroxy-1-methoxy-5-methyl-3-[4-(trifluoromethyl)-2-pyridyl]imidazolidin-2-one and (4S,5S)-4-hydroxy-1-methoxy-5-methyl-3-[4-(trifluoromethyl)-2-pyridyl]imidazolidin-2-one.

The absolute stereochemistry could be proven by synthesis (see Example 8—alternative synthesis below) and also by X-ray crystallography after recrystallization of a sample from DCM/isoHexane. NMR and LC-MS data for A3 and A4 were consistant with A8 (example 4).

The diastereomeric ratio was found to vary according to conditions for product synthesis, purification and analysis. The stereochemistry of the chiral centre at the carbon containing the hydroxyl group was found to interconvert at room temperature.

Example 8—Preparation of (4S,5S)-4-hydroxy-1-methoxy-5-methyl-3-[4-(trifluoromethyl)-2-pyridyl]imidazolidin-2-one and (4R,5S)-4-hydroxy-1-methoxy-5-methyl-3-[4-(trifluoromethyl)-2-pyridyl]imidazolidin-2-one (A3)—Alternative Synthesis Procedure for Synthesis of methyl (2S)-2-(methoxyamino)propanoate (Step-1)

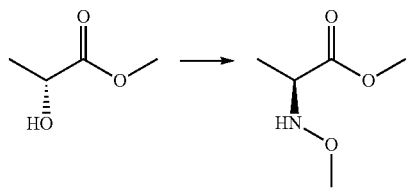

To a stirred solution of methyl (2R)-2-hydroxypropanoate (16.5 g, 158 mmol, 15.1 mL) in DCM (475 mL) at 0° C. was added trifluoromethanesulfonic anhydride (49.7 g, 174 mmol) followed after 5 mins by 2,6-dimethylpyridine (19.5 g, 182 mmol). The resulting mixture was stirred at 0° C. for 10 minutes to give a solution of methyl (2R)-2-(trifluoromethylsulfonyloxy)propanoate. Separately, O-methylhydroxylamine hydrochloride (65.98 g, 790.0 mmol) was dissolved in water (130 mL) then sodium hydroxide (50% aqueous) (33.1 mL 632.0 mmol) was added. The solution of O-methylhydroxylamine in water was added to the solution of methyl (2R)-2-(trifluoromethylsulfonyloxy)propanoate in DCM, and the mixture was stirred at room temperature for 30 minutes. The organic layer was separated and chromatographed on silica eluting with 0-45% EtOAc in isohexane. Fractions containing product were evaporated to give the desired product as a pale yellow oil (23.5 g). The product appears to have some volatility so caution was taken with the evaporation step. The product was used without further purification.

Procedure for Synthesis of methyl (2S)-2-[methoxy-[[4-(trifluoromethyl)-2-pyridyl]carbamoyl]amino]propanoate (Step-2)

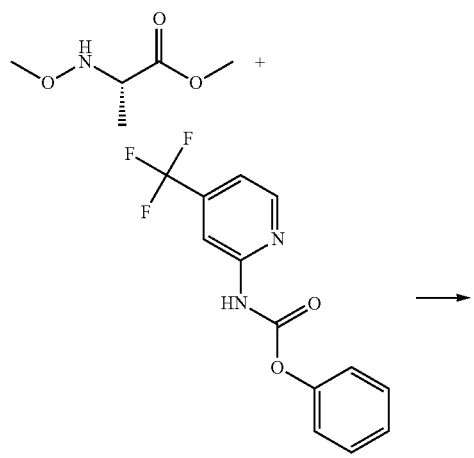

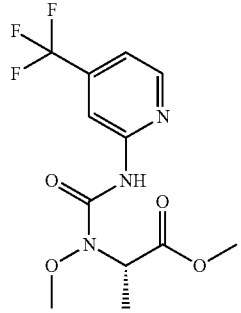

Procedure as for example 5 alternative synthesis.

Procedure for Synthesis of (4S,5S)-4-hydroxy-1-methoxy-5-methyl-3-[4-(trifluoromethyl)-2-pyridyl]imidazolidin-2-one and (4R,5S)-4-hydroxy-1-methoxy-5-methyl-3-[4-(trifluoromethyl)-2-pyridyl]imidazolidin-2-one (A3) (Step-3)

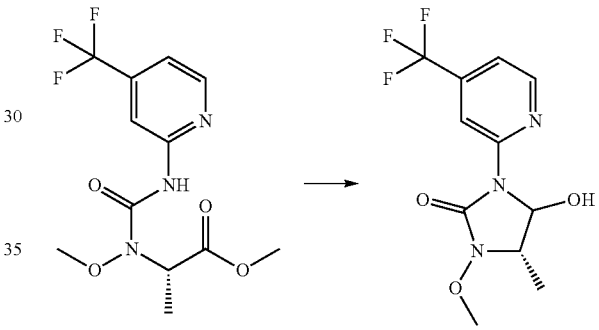

To a stirred solution of methyl (2S)-2-[methoxy-[[4-(trifluoromethyl)-2-pyridyl]carbamoyl]amino]propanoate (18.3 g, 57.0 mmol) in a mixture of tetrahydrofuran (103 mL) and methanol (103 mL) at 5° C. under nitrogen was added $NaBH_4$ (5.10 g, 2.25 equiv.) portionwise over 20 mins, keeping the internal temperature below ~6.5° C. The mixture was then stirred at 6.5° C. for 1 h before the reaction was quenched with acetone (50 mL) slowly over 45 minutes with external cooling to keep the internal temperature below ~6.5° C. Sat. aqueous $NH_4Cl$ solution (150 mL) was added followed by water (150 mL). The reaction was stirred at 15° C. for 10 mins, then extracted with DCM (4×400 mL and then 1×100 mL). Combined DCM fractions were washed with water (50 mL) dried ($Na_2SO_4$), filtered and concentrated to ~200 mL volume, then chromatographed on silica eluting with 0-27% EtOAc in isohexane. Fractions containing product were evaporated to give the desired product as a white solid (5.65 g, 34%).

NMR and LC-MS data for A3 was consistant with A8 (example 4).

The diastereomeric ratio was found to vary according to conditions for product synthesis, purification and analysis. The stereochemistry of the chiral centre at the carbon containing the hydroxyl group was found to interconvert at room temperature.

Examples 9 and 10—Preparation of 4,5-dihydroxy-1-methyl-3-[4-(trifluoromethyl)-2-pyridyl]imidazolidin-2-one (A7) and 5-ethoxy-4-hydroxy-1-methyl-3-[4-(trifluoromethyl)-2-pyridyl]imidazolidin-2-one (A6)

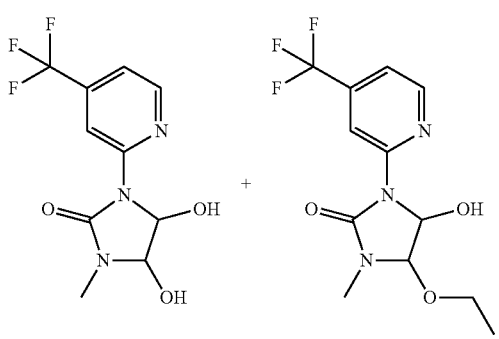 [SMILES: CN1C(=O)N(c2cc(C(F)(F)F)ccn2)C(O)C1O ; CCOC1C(O)N(c2cc(C(F)(F)F)ccn2)C(=O)N1C]

Procedure for Synthesis of 4 1-methyl-3-[4-(trifluoromethyl)-2-pyridyl]urea (Step-1)

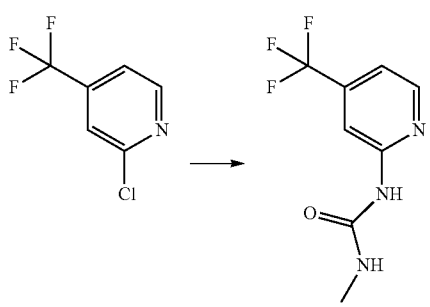

A mixture of tris(dibenzylideneacetone)dipalladium(0) (0.202 g, 0.220 mmol), 4,5-bis(diphenylphosphino)-9,9-dimethylxanthene (0.493 g, 0.826 mmol), potassium carbonate (1.93 g, 13.8 mmol) and methylurea (0.408 g, 5.51 mmol) in 1,4-dioxane (30 mL) was treated with 2-chloro-4-(trifluoromethyl)pyridine (commercially available) (1.0 g, 5.51 mmol), The mixture was warmed to 75-80° C. with stirring under a Nitrogen atmosphere for 3.5 h. The reaction mixture was diluted with EtOAc (20 mL) and water (20 mL) and filtered through a pad of celite, rinsing through with further small portions of EtOAc and water. The organic phase was separated and the aqueous further extracted with EtOAc (5 mL). The organic extracts were combined, washed with brine (10 mL), dried over MgSO$_4$, filtered and the filtrate evaporated giving an orange liquid. This was chromatographed (eluting with an EtOAc/iso-hexane gradient) and fractions containing product were evaporated and triturated with iso-hexane to give the desired product as a light yellow powder (0.669 g, 55%).

$^1$H NMR (CDCl$_3$): 9.44 (br.s, 1H), 9.04 (br.s, 1H), 8.32 (d, 1H), 7.15 (s, 1H), 7.06 (d, 1H), 2.99 (d, 3H).

LC-MS: (positive ES MH+ 220).

Procedure for Synthesis of 4,5-dihydroxy-1-methyl-3-[4-(trifluoromethyl)-2-pyridyl]imidazolidin-2-one (A7) and 5-ethoxy-4-hydroxy-1-methyl-3-[4-(trifluoromethyl)-2-pyridyl]imidazolidin-2-one (A6) (Step-2)

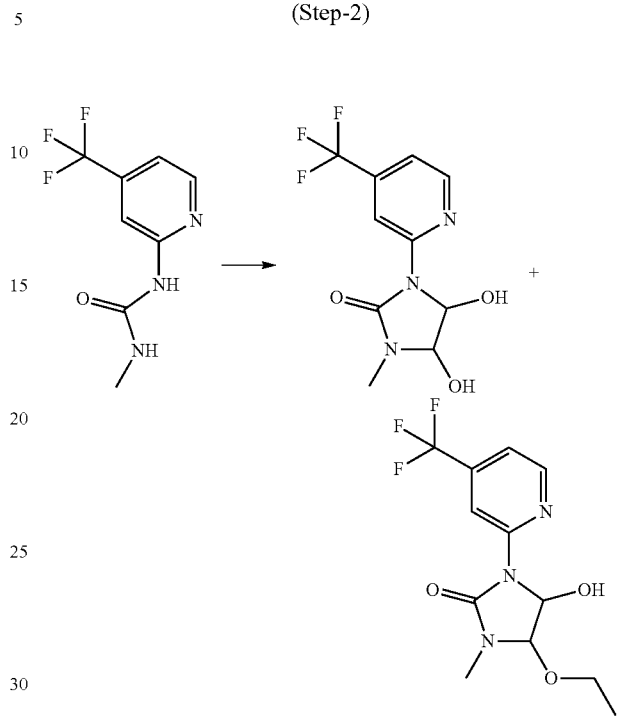

To 1-methyl-3-[4-(trifluoromethyl)-2-pyridyl]urea (0.65 g, 3.0 mmol) in ethanol (20 mL) was added glyoxal (40% aqueous solution) (2.6 g, 18 mmol, 2.0 mL) via syringe, the mixture then being warmed and heated at reflux for 2 hours. The reaction mixture was allowed to cool to room temperature and concentrated to give a syrupy residue. This was dissolved in DCM (50 mL) and washed with brine (2×5 mL). The organic phase was dried (MgSO$_4$) filtered and the filtrate concentrated giving the crude product as a dark green gum (1.07 g). The crude product was dissolved in DCM (20 mL) then chromatographed on silica eluting with EtOAc in isohexane. Fractions containing product were evaporated to give 4,5-dihydroxy-1-methyl-3-[4-(trifluoromethyl)-2-pyridyl]imidazolidin-2-one (0.562 g, 68%) and 5-ethoxy-4-hydroxy-1-methyl-3-[4-(trifluoromethyl)-2-pyridyl]imidazolidin-2-one (0.11 g, 12%).

4,5-Dihydroxy-1-methyl-3-[4-(trifluoromethyl)-2-pyridyl]imidazolidin-2-one $^1$H NMR (CDCl$_3$): Major diastereoisomer: 8.35 (br.s, 1H), 8.32 (d, 1H), 7.12 (dd, 1H), 5.71 (d, 1H); 4.96 (m, 1H), 4.82 (m, 1H), 3.54 (d, 1H), 3.01 (s, 3H).
Minor diastereoisomer: 8.47 (br.s, 1H), 8.38 (d, 1H), 7.19 (dd, 1H), 5.89 (d, 1H), 5.15 (m, 1H), 5.12 (m, 1H), 3.82 (d, 1H), 2.97 (s, 3H).

LC-MS: (positive ES MH+ 278).

5-Ethoxy-4-hydroxy-1-methyl-3-[4-(trifluoromethyl)-2-pyridyl]imidazolidin-2-one (Existing Predominately as the Trans Diastereoisomer)

$^1$H NMR (CDCl$_3$): 8.46 (s, 1H), 8.38 (d, 1H), 7.18 (dd, 1H), 5.73 (d, 1H), 4.82 (d, 1H), 4.71 (s, 1H), 3.66 (m, 2H), 3.00 (s, 3H), 1.28 (t, 3H).

LC-MS: (positive ES MH+ 306).

Examples 11 and 12—Preparation of 5-ethoxy-4-hydroxy-1-methyl-3-[4-(trifluoromethyl)-2-pyridyl]imidazolidin-2-one (Enantiomer 1, A34) and 5-ethoxy-4-hydroxy-1-methyl-3-[4-(trifluoromethyl)-2-pyridyl]imidazolidin-2-one (Enantiomer 2, A35)

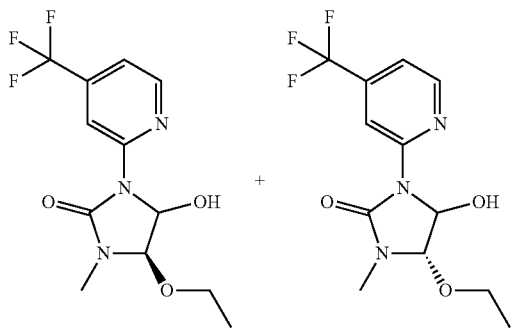 [SMILES: CCO[C@@H]1C(O)N(c2cc(C(F)(F)F)ccn2)C(=O)N1C ; CCO[C@H]1C(O)N(c2cc(C(F)(F)F)ccn2)C(=O)N1C]

5-ethoxy-4-hydroxy-1-methyl-3-[4-(trifluoromethyl)-2-pyridyl]imidazolidin-2-one (A6) was separated into individual enantiomers E1 and E2 by preparative chiral HPLC (CHIRALPAK IC column, eluting with isoHexane (containing 0.1% TFA) and IPA).

The first eluting enantiomer E1 was purified further by chromatography on silica eluting with EtOAc in isohexane. Fractions containing product were evaporated to give pure enantiomer E1 (A34). A34 could be assigned as (5R)-5-ethoxy-4-hydroxy-1-methyl-3-[4-(trifluoromethyl)-2-pyridyl]imidazolidin-2-one by inference from biological activity of related compounds of known absolute configuration and comparison of elution time from chiral HPLC.

Enantiomer E2 (A35) was sufficiently pure after the chiral HPLC purification and could be assigned as (5S)-5-ethoxy-4-hydroxy-1-methyl-3-[4-(trifluoromethyl)-2-pyridyl]imidazolidin-2-one by inference from biological activity of related compounds of known absolute configuration and comparison of elution time from chiral HPLC.

NMR and LC-MS data was consistant with racemic 5-ethoxy-4-hydroxy-1-methyl-3-[4-(trifluoromethyl)-2-pyridyl]imidazolidin-2-one (A6)—both enantiomers were of predominantly trans configuration as determined by NMR.

Example 13—Preparation of 4-hydroxy-1,5-dimethyl-3-[4-(trifluoromethyl)-2-pyridyl]imidazolidin-2-one (A19)

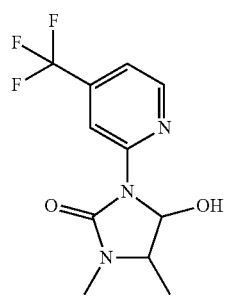 [SMILES: CC1C(O)N(c2cc(C(F)(F)F)ccn2)C(=O)N1C]

Procedure for Synthesis of 1,1-dimethoxy-N-methyl-propan-2-amine (Step 1)

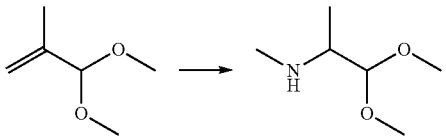

Ti(O-iPr)$_4$ (34.3 g, 2 equiv.) was cooled to 10° C. under a nitrogen atmosphere then ethanol (89 mL) was added followed by 1,1-dimethoxypropan-2-one (7.14 g, 1 equiv), methylamine hydrochloride (8.16 g, 2 equiv.) and triethylamine (16.8 mL, 2 equiv.). The reaction was stirred at room temperature for 15 h. The reaction was cooled to 10° C. and then NaBH$_4$ (3.43 g, 1.5 equiv.) was added and the reaction was stirred at room temperature for 6 h. The reaction was cooled to 10° C., then carefully over 10 minutes poured into ice cold aqueous ammonia (180 mL, 2M). The mixture was filtered, washing through with DCM (300 mL). The layers were separated and then the aqueous layer was extracted with further DCM (3×100 mL). The combined DCM layers were dried (Na$_2$SO$_4$), filtered and evaporated with care as to not lose any of the volatile product. This crude material was distilled on a Kugelrohr (70 to 110° C. 14 mBar) to give product (4.41 g) as a colourless oil, which was used without further purification.

1H NMR (CDCl$_3$): 4.11 (d, 1H), 3.41 (s, 6H), 2.69 (pentet, 1H), 2.43 (s, 3H), 1.06 (d, 3H).

Procedure for Synthesis of 1-(2,2-dimethoxy-1-methyl-ethyl)-1-methyl-urea (Step 2)

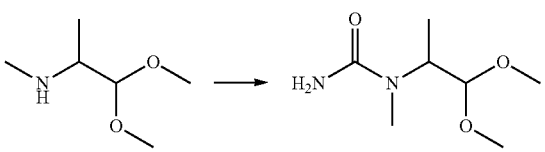

1,1-dimethoxy-N-methyl-propan-2-amine (1.0 g, 7.50 mmol) was dissolved in CDCl$_3$ (1.5 mL). Trimethylsilyl isocyanate (commercially available) (2 equiv.) was added and the reaction was stirred at room temp for 4 days. The reaction mixture heated to reflux for 160 minutes while incrementally adding a further trimethylsilyl isocyanate (1.5 equiv.) The reaction was evaporated and treated with water (10 mL), stirred for 90 minutes, then evaporated to give crude product (1.08 g) which was used without further purification.

1H NMR (CDCl$_3$): 4.60 (br s, 2H), 4.30 (br s, 1H), 4.24 (d, 1H), 3.41 (s, 6H), 2.71 (s, 3H), 1.18 (d, 3H).

Procedure for Synthesis of 1-(2,2-dimethoxy-1-methyl-ethyl)-1-methyl-3-[4-(trifluoromethyl)-2-pyridyl]urea (Step 3)

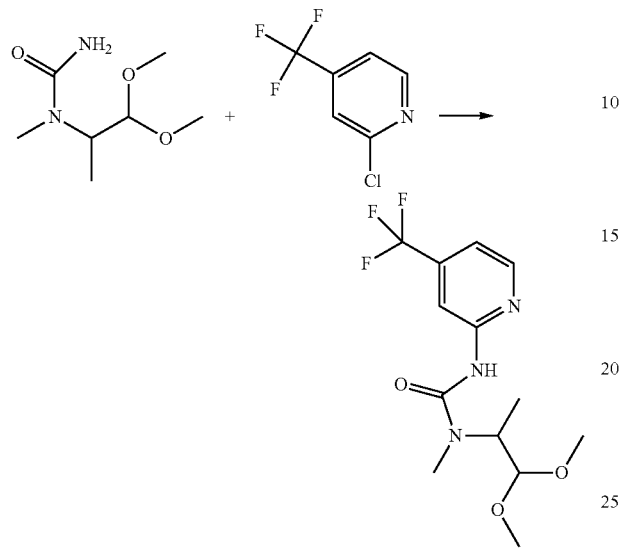

1-(2,2-dimethoxy-1-methyl-ethyl)-1-methyl-urea (220 mg, 1.249 mmol), 2-chloro-4-(trifluoromethyl)pyridine (commercially available) (272 mg, 1.2 equiv.), potassium carbonate (259 mg, 1.5 equiv.), tris(dibenzylideneacetone)dipalladium(0) (47 mg), 4,5-bis(diphenylphosphino)-9,9-dimethylxanthene (111 mg) were suspended in 1-4-dioxane (6 mL) and the mixture was then heated at 105° C. in a sealed vial for 1 h. The mixture was allowed to cool to room temperature, diluted with EtOAc (6 mL), filtered then chromatographed on silica eluting with 0-100% EtOAc in isohexane. Fractions containing product were evaporated to give the desired product as a colourless gum (282 mg, 70%).

LC-MS: (positive ES MH+ 322).

Procedure for Synthesis of 4-hydroxy-1,5-dimethyl-3-[4-(trifluoromethyl)-2-pyridyl]-imidazolidin-2-one (A19) (Step 4)

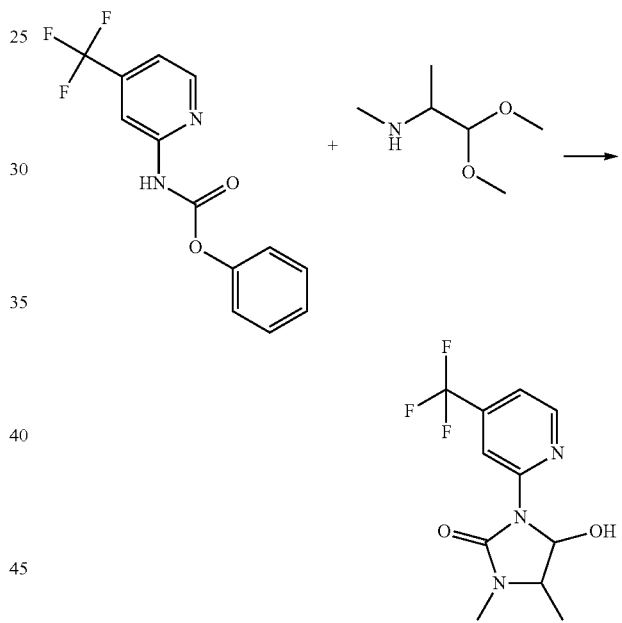

1-(2,2-dimethoxy-1-methyl-ethyl)-1-methyl-3-[4-(trifluoromethyl)-2-pyridyl]urea (240 mg, 0.787 mmol) was dissolved in acetic acid (6 mL), then water (3 mL) was added to give a homogeneous solution. This was stirred at room temperature for 2 days and then at 60° C. for 1 h. The reaction was evaporated (100 to 1 mBar at 20-35° C. for 2 h) to remove traces of HOAc to give product (204 mg, 99%) as an amber gum.

1H NMR (CDCl$_3$): Major diastereomer: 8.54 (s, 1H), 8.37 (d, 1H), 7.16 (d, 1H), 5.61 (m, 1H), 4.95 (br s, 1H), 3.53 (m, 1H), 2.93 (s, 3H), 1.34 (d, 3H).

Minor diastereomer: 8.54 (s, 1H), 8.39 (m, 1H), 7.16 (d, 1H), 5.95 (d, 1H), 4.81 (br s, 1H), 3.76 (pentet, 1H), 2.89 (s, 3H), 1.40 (d, 3H).

LC-MS: (positive ES MH+ 276).

The diastereomeric ratio was found to vary according to conditions for product synthesis, purification and analysis. The stereochemistry of the chiral centre at the carbon containing the hydroxyl group was found to interconvert at room temperature.

Example 14—Preparation of 4-hydroxy-1,5-dimethyl-3-[4-(trifluoromethyl)-2-pyridyl]imidazolidin-2-one (A19)—Alternative Synthesis Phenyl N-[4-(trifluoromethyl)-2-pyridyl]carbamate (for a synthesis see WO 2007004749) (4.54 g, 1.05 equiv.) was suspended in 1,4-dioxane (12 mL) under a Nitrogen atmosphere and then 1,1-dimethoxy-N-methyl-propan-2-amine (3.46 g, 15.3 mmol) was added and the reaction was heated at 105° C. for 25 mins. Aqueous 2N HCl (20 mL) was added to the reaction mixture and this was heated to 32° C. for 30 mins. EtOAc (5 mL) and water (50 mL) were added and the aqueous phase was extracted with further EtOAc (2×50 mL). The combined EtOAc layers were washed with sat. aqueous NaHCO$_3$ (5 mL), evaporated and then chromatographed on silica eluting with 0-100% EtOAc in isohexane. Fractions containing product were evaporated to give a colourless gum which slowly crystallised to give product (3.80 g, 90%).

NMR and LC-MS consistant with A19 from example 13 above.

The diastereomeric ratio was found to vary according to conditions for product synthesis, purification and analysis.

The stereochemistry of the chiral centre at the carbon containing the hydroxyl group was found to interconvert at room temperature.

Example 15—Preparation of 5-allyl-4-hydroxy-1-methyl-3-[4-(trifluoromethyl)-2-pyridyl]imidazolidin-2-one (A32)

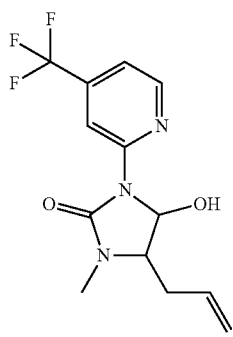 [SMILES: C=CCC1C(O)N(c2cc(C(F)(F)F)ccn2)C(=O)N1C]

Procedure for Synthesis of methyl 2-[[4-(trifluoromethyl)-2-pyridyl]carbamoylamino]pent-4-enoate (Step 1)

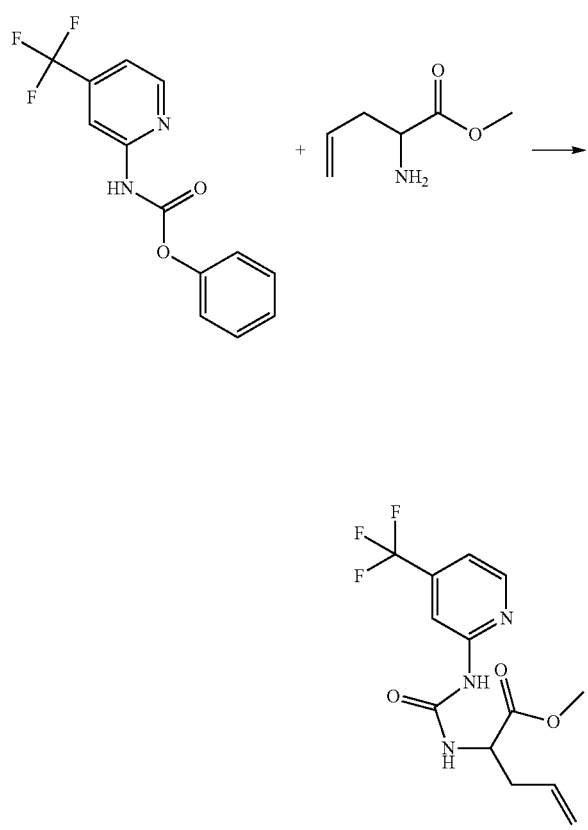

To phenyl N-[4-(trifluoromethyl)-2-pyridyl]carbamate (for a synthesis see WO 2007004749) (0.328 g, 1.16 mmol) dissolved in 1,4-dioxane (6 mL), under a Nitrogen atmosphere, was added methyl 2-aminopent-4-enoate (for a synthesis see WO2007137168) (0.150 g, 1.16 mmol). The mixture was then warmed to 80° C. for 3 h. The reaction temperature was then raised to 100° C., and heating continued for a further 1.5 h. The reaction mixture was concentrated to remove the bulk of solvent, the oily residue being taken up in EtOAc (20 mL) and washed with water (2×5 mL). The organic phase was separated and dried over MgSO$_4$, filtered and then chromatographed on silica eluting with EtOAc in isohexane. Fractions containing product were evaporated to give product as a white solid (0.167 g, 45%) LC-MS: (positive ES MH+ 318).

Procedure for Synthesis of 5-allyl-3-[4-(trifluoromethyl)-2-pyridyl]imidazolidine-2,4-dione (Step 2)

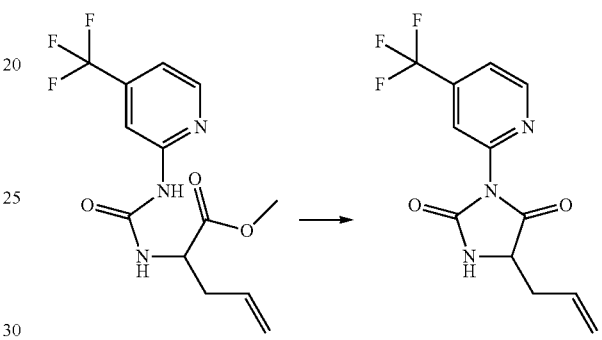

Methyl 2-[[4-(trifluoromethyl)-2-pyridyl]carbamoylamino]pent-4-enoate (0.114 g, 0.359 mmol) was dissolved in 1,4-dioxane (4 mL) was treated with 2N hydrochloric acid (4 mL) and the mixture was heated at 60-70° C. for 3 h. The reaction temp was raised to 85° C. and heating continued for a further 1 h. The reaction mixture then being allowed to cool to room temperature and then concentrated. The residue was taken into DCM (15 mL) and the organic phase separated. The aqueous was further extracted with DCM (2×10 mL) and the DCM extracts combined, dried over MgSO$_4$, filtered and the filtrate concentrated giving crude intermediate 2-[[4-(trifluoromethyl)-2-pyridyl]carbamoylamino] pent-4-enoic acid as a white gum (47 mg). The aqueous phase was evaporated giving further 2-[[4-(trifluoromethyl)-2-pyridyl]carbamoylamino]pent-4-enoic acid as a white foam (73 mg). Both fractions of 2-[[4-(trifluoromethyl)-2-pyridyl]carbamoylamino]pent-4-enoic acid were combined and used with further purification in the next step. The crude 2-[[4-(trifluoromethyl)-2-pyridyl]carbamoylamino]pent-4-enoic acid was taken into DCM (4 mL), then oxalyl chloride (0.0912 g, 0.719 mmol) was added to the fine slurry at room temperature. The reaction mixture was stirred for 2 h and then allowed to stand overnight. The reaction mixture was concentrated and the residue taken into EtOAc (20 mL) and washed with water (5 mL). The organic phase was separated, the aqueous being further extracted with EtOAc (10 mL). The organic extracts were then combined, washed with water (3 mL), dried over MgSO$_4$, filtered and the filtrate concentrated giving crude product as a light brown gum that began to solidify on standing (141 mg). This was used in the next step without further purification.

LC-MS: (positive ES MH+ 286).

Procedure for Synthesis of 5-allyl-1-methyl-3-[4-(trifluoromethyl)-2-pyridyl]imidazolidine-2,4-dione (Step 3)

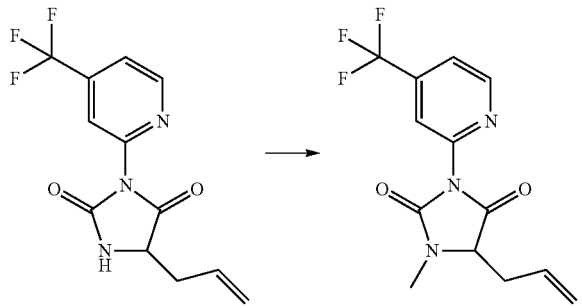 [SMILES: C=CCC1NC(=O)N(c2cc(C(F)(F)F)ccn2)C1=O ; C=CCC1C(=O)N(c2cc(C(F)(F)F)ccn2)C(=O)N1C]

A solution of 5-allyl-3-[4-(trifluoromethyl)-2-pyridyl]imidazolidine-2,4-dione (0.120 g, 0.421 mmol) in DMF (1.5 mL) was cooled to 0-5° C. in an ice bath was treated dropwise with LiHMDS (1.0M in THF, 0.442 mmol, 0.442 mL). The resultant solution was stirred 5 minutes, then iodomethane (0.0717 g, 0.505 mmol) was added and stirring continued for 40 minutes. The reaction mixture was concentrated and the oily residue being taken up in EtOAc (15 mL) and washed with brine (3×2 mL), dried over MgSO$_4$, filtered and the filtrate concentrated giving crude product, which was chromatographed on silica eluting with EtOAc in isohexane. Fractions containing product were evaporated to give product as a white solid (0.060 g, 48%).

LC-MS: (positive ES MH+ 300).

Procedure for Synthesis of 5-allyl-4-hydroxy-1-methyl-3-[4-(trifluoromethyl)-2-pyridyl]imidazolidin-2-one (Step 4)

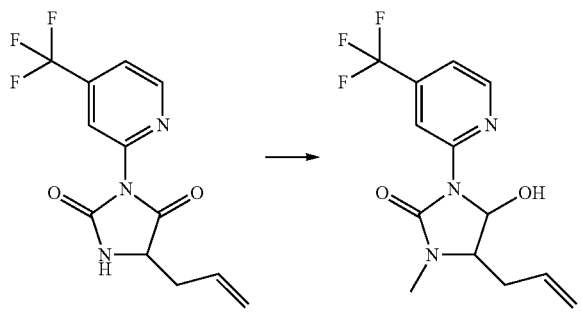 [SMILES: C=CCC1NC(=O)N(c2cc(C(F)(F)F)ccn2)C1=O ; C=CCC1C(O)N(c2cc(C(F)(F)F)ccn2)C(=O)N1C]

5-allyl-1-methyl-3-[4-(trifluoromethyl)-2-pyridyl]imidazolidine-2,4-dione (0.057 g, 0.19 mmol) in methanol (10 mL) was cooled to around −35° C. (acetone/CO$_2$ bath). NaBH$_4$ (0.0073 g, 0.19 mmol) was added in a single portion and the reaction was stirred for 30 minutes at between −30 and −40° C. The reaction mixture was allowed to warm slowly to room temperature. Further NaBH$_4$ (0.0073 g, 0.19 mmol) was added and the mixture stirred at room temp for a further 30 minutes. The reaction mixture was quenched by the careful addition of water (2 mL), then concentrated and the residue being left to stand at room temperature for 72 h. The mixture was diluted with EtOAc (20 mL) and the organic phase separated. The aqueous phase was further extracted with EtOAc (15 mL) and the organic extracts combined, washed with water (5 mL), dried over MgSO$_4$, filtered and evaporated to give product as a light grey gum (56 mg, 98%).

LC-MS: (positive ES MH+ 302).

1H NMR (CDCl$_3$): Major diastereomer: 8.15 (s, 1H), 8.37 (d, 1H), 7.15 (dd, 1H), 5.75 (m, 1H), 5.70 (d, 1H), 5.23 (dd, 1H), 5.20 (dd, 1H), 4.90 (d, 1H), 3.54 (ddd, 1H), 2.96 (s, 3H), 2.55 (m, 1H), 2.53 (m, 1H).

1H NMR (CDCl$_3$): Minor diastereomer: 8.15 (s, 1H), 8.37 (d, 1H), 7.15 (dd, 1H), 5.98 (m, 1H), 5.70 (d, 1H), 5.26 (dd, 1H), 5.18 (d, 1H), 4.79 (br.s, 1H), 3.65 (ddd, 1H), 2.91 (s, 3H), 2.69 (m, 1H), 2.55 (m, 1H).

Example 16—Preparation of 4-hydroxy-1-methyl-5-(trifluoromethyl)-3-[4-(trifluoromethyl)-2-pyridyl]imidazolidin-2-one (A33)

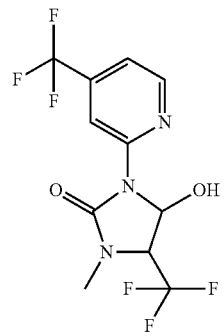 [SMILES: CN1C(=O)N(c2cc(C(F)(F)F)ccn2)C(O)C1C(F)(F)F]

Procedure for Synthesis of 2,2-dimethoxy-N-methyl-ethanimine (Step 1)

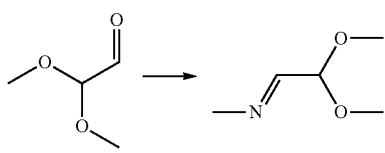

Methylamine hydrochloride (4.05 g, 1.05 equiv.) in DCM (60 mL) was cooled to 0° C., then K$_2$CO$_3$ (5.53 g, 1 equiv.) was added over 5 minutes. Reaction was stirred at 0° C. for a further 10 minutes then 2,2-dimethoxyacetaldehyde (6.04 mL, 40 mmol) was added and the reaction was stirred vigorously at 0° C. After 5 minutes at 0° C., the reaction was allowed to warm to room temperature. After 15 minutes at room temperature, DCM was decanted off, solid was extracted with DCM (2×15 mL). Combined DCM fractions were dried (Na$_2$SO$_4$), filtered, and evaporated to give product which was used without further purification (4.10 g, 87%).

Procedure for Synthesis of 1,1,1-trifluoro-3,3-dimethoxy-N-methyl-propan-2-amine (Step 2)

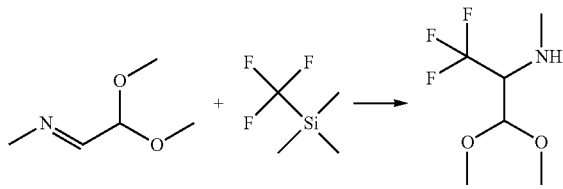

KHF$_2$ (2.01 g, 0.75 equiv.) was suspended in MeCN (69 mL) and DMF (8.0 mL) under Nitrogen, and cooled to 0° C. then 2,2-dimethoxy-N-methyl-ethanimine (4.02 g, 1 equiv.) was added followed by dropwise addition of TFA (3.28 mL, 1.25 equiv.) over 2 minutes. Reaction was stirred at 0° C. for 5 minutes, then trimethyl(trifluoromethyl)silane (7.6 mL, 1.5 equiv.) was added over 5 minutes and the reaction was stirred at 0° C. for 3 h. Reaction was then treated with sat. aqueous NaHCO$_3$ (50 mL) over 3 minutes The reaction mixture was then extracted with diethyl ether (3×200 mL), dried (Na$_2$SO$_4$), filtered and evaporated (care as product is volatile) to give product (14.1 g, 44%), which was used without further purification.

Procedure for Synthesis of 1,1,1-trifluoro-3,3-dimethoxy-N-methyl-propan-2-amine (Step 3)

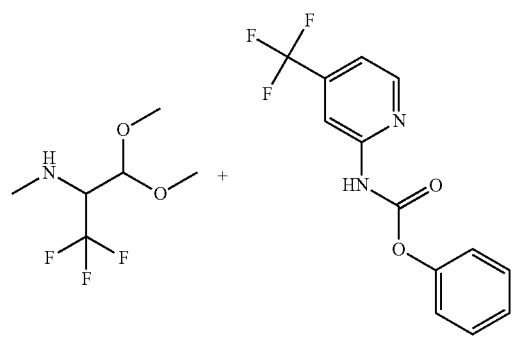

Crude 1,1,1-trifluoro-3,3-dimethoxy-N-methyl-propan-2-amine (3.58 g, 1.2 equiv.) was dissolved in 1,4-dioxane (2.5 mL) and treated with N-[4-(trifluoromethyl)-2-pyridyl]carbamate (for a synthesis see WO 2007004749) (1.00 g, 3.19 mmol) and heated at 110° C. for 2 h 15 minutes. Reaction mixture was then evaporated and the residue chromatographed on silica eluting with EtOAc in isohexane (0-35%). Fractions containing product were evaporated to give product as a gum (0.40 g, 33%).

LC-MS: (positive ES MH+ 376).

Procedure for Synthesis of 4-hydroxy-1-methyl-5-(trifluoromethyl)-3-[4-(trifluoromethyl)-2-pyridyl]imidazolidin-2-one (Step 4)

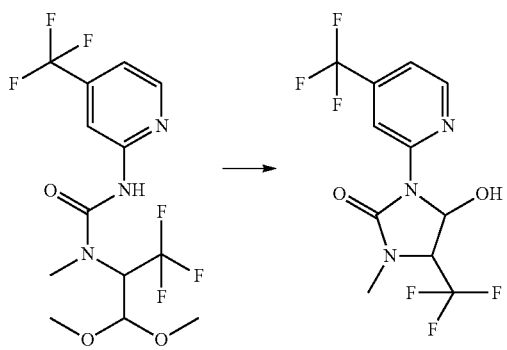 [SMILES: COC(OC)C(N(C)C(=O)Nc1cc(C(F)(F)F)ccn1)C(F)(F)F ; CN1C(=O)N(c2cc(C(F)(F)F)ccn2)C(O)C1C(F)(F)F]

1,1,1-trifluoro-3,3-dimethoxy-N-methyl-propan-2-amine (0.377 g) was suspended in water (2 mL) and then treated with TFA (2 mL) and the reaction mixture was then heated to 60° C. for 1.5 h. The reaction was evaporated and treated with sat. aqueous NaHCO$_3$ (15 mL) and DCM (15 mL). The aqueous phase was further extracted with DCM (2×10 mL) and then the combined DCM phases were dried (Na$_2$SO$_4$), filtered and evaporated to give product as a white solid (320 mg, 97%).

LC-MS: (positive ES MH+ 330).

1H NMR (CDCl$_3$): 8.48 (s, 1H), 8.42 (d, 1H), 7.25 (d, 1H), 6.02 (m, 1H), 5.01 (br s, 1H), 3.93 (m, 1H), 3.10 (s, 3H).

Example 17—Preparation of (4R,5S)-4-hydroxy-1,5-dimethyl-3-[4-(trifluoromethyl)-2-pyridyl]imidazolidin-2-one and (4S,5S)-4-hydroxy-1,5-dimethyl-3-[4-(trifluoromethyl)-2-pyridyl]imidazolidin-2-one (A37)

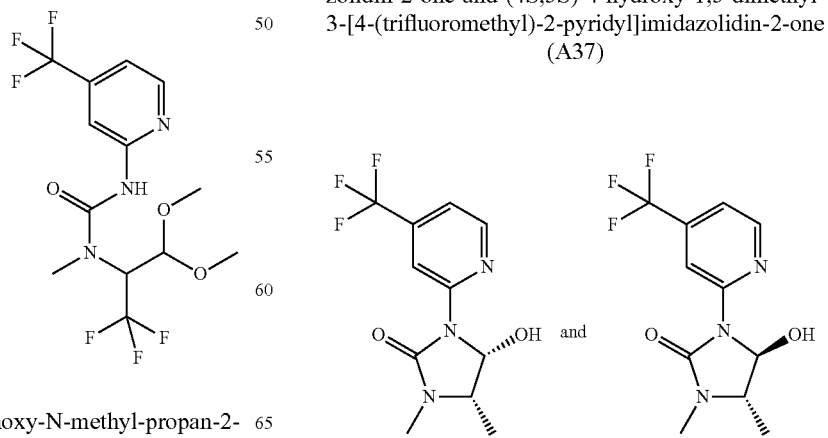

Procedure for Synthesis of (4-nitrophenyl) N-[4-(trifluoromethyl)-2-pyridyl]carbamate (Step 1)

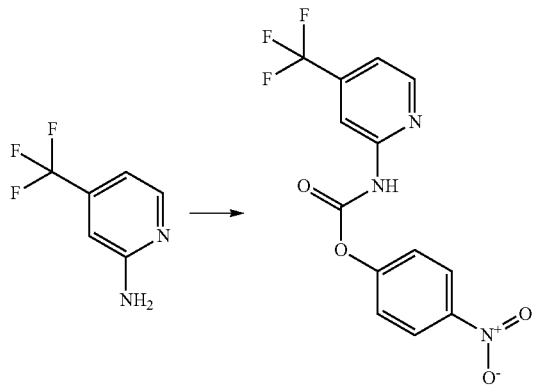 [SMILES: Nc1cc(C(F)(F)F)ccn1 ; O=C(Nc1cc(C(F)(F)F)ccn1)Oc1ccc([N+](=O)[O-])cc1]

To a stirred solution of 4-(trifluoromethyl)pyridin-2-amine (5 g, 30.84 mmol) and pyridine (2.56 g, 32.38 mmol) in DCM (75 mL) at 0° C. (internal temp) was added (4-nitrophenyl) carbonochloridate (6.22 g, 30.84 mmol,) over 15 mins, keeping temp at or below 8° C., and the reaction mixture was then stirred at 0° C. for 1 h. After 90 mins at 0° C., the reaction was allowed to warm to room temperature, and stirred at for 1 hr. Ice cold water (25 mL) was added. The biphasic mixture was filtered and the precipitate washed with ice cold water (10 mL) and DCM (2×10 mL). The precipitate was dried under vacuum to give product as a white solid (7.60 g, 75%).

LC-MS: (positive ES MH+ 328).

Procedure for Synthesis of (5S)-1,5-dimethyl-3-[4-(trifluoromethyl)-2-pyridyl]imidazolidine-2,4-dione (Step 2)

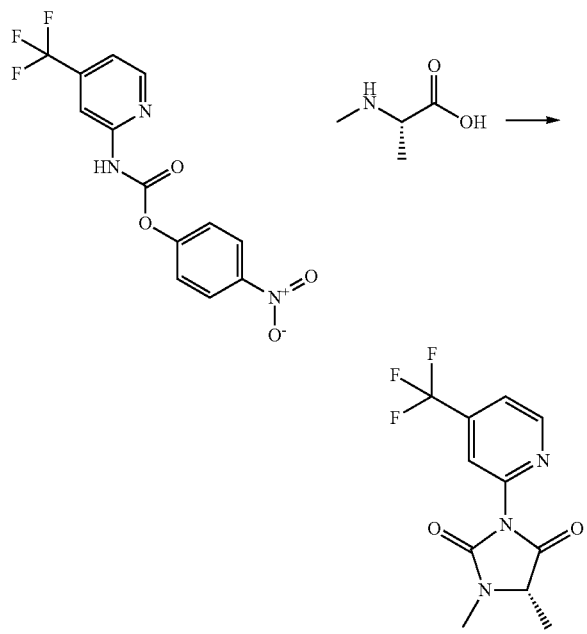

A mixture of (4-nitrophenyl) N-[4-(trifluoromethyl)-2-pyridyl]carbamate (1.20 g, 3.67 mmol) and 1,4-dioxane (12 mL), under a nitrogen atmosphere, was treated with (2S)-2-(methylamino)propanoic acid (commercially available) (0.416 g, 4.03 mmol, and the mixture was stirred at room temperature for 5 h then at 60° C. for 1.5 h, left at room temperature overnight, then heated at 80° C. for 1.5 h and then left over the weekend at rt. The reaction mixture was filtered rinsing through with small portions of EtOAc, then the filtrate and washings were combined and concentrated to give a deep yellow oily residue. The oily residue was taken into EtOAc (25 mL) and washed with saturated NaHCO₃ solution (3×15 mL) and brine (10 mL). The organic phase was dried over MgSO₄, filtered, evaporated and the residue chromatographed on silica eluting with EtOAc in isohexane. Fractions containing product were evaporated to give product (0.675 g, 67%).

LC-MS: (positive ES MH+ 274).

Procedure for Synthesis of (4R,5S)-4-hydroxy-1,5-dimethyl-3-[4-(trifluoromethyl)-2-pyridyl]imidazolidin-2-one and (4S,5S)-4-hydroxy-1,5-dimethyl-3-[4-(trifluoromethyl)-2-pyridyl]imidazolidin-2-one (A37) (Step 3)

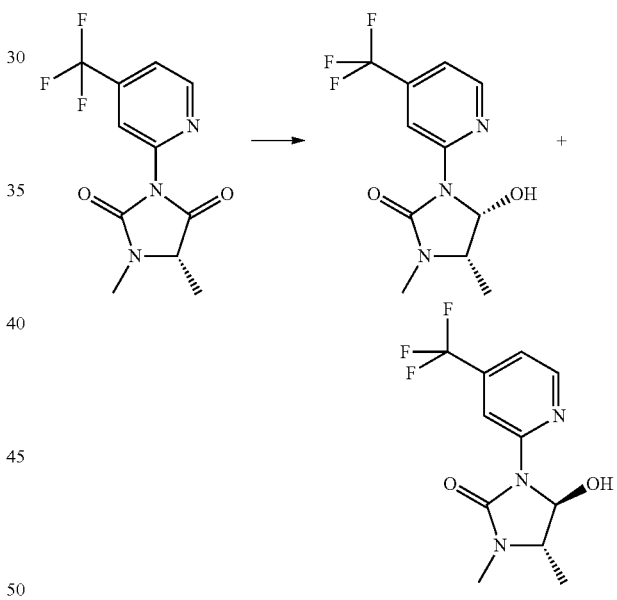

(5S)-1,5-dimethyl-3-[4-(trifluoromethyl)-2-pyridyl]imidazolidine-2,4-dione (0.660 g, 2.42 mmol) was stirred in methanol (20 mL) and the solution was cooled to around −15° C. (ice-salt bath). Sodium borohydride (0.0933 g, 2.42 mmol) was added in a single portion and the reaction was allowed to warm to 15° C. over 1 h, and was then quenched by the careful addition of water (0.5 mL). After 5 minutes stirring the mixture was diluted further with water (40 mL). A white precipitate formed, which was filtered off, washed with water and dried under suction giving a white powder. The combined filtrate and washings were extracted with DCM (3×20 mL). The organic extracts were then combined, washed with brine (2×20 mL), dried over MgSO₄, filtered and the filtrate concentrated giving a light grey gum, (0.367 g, 55%).

NMR and LC-MS consistant with example 13 (A19).

The diastereomeric ratio was found to vary according to conditions for product synthesis, purification and analysis. The stereochemistry of the chiral centre at the carbon containing the hydroxyl group was found to interconvert at room temperature.

Example 18—Preparation of (4R,5R)-4-hydroxy-1,5-dimethyl-3-[4-(trifluoromethyl)-2-pyridyl]imidazolidin-2-one and (4S,5R)-4-hydroxy-1,5-dimethyl-3-[4-(trifluoromethyl)-2-pyridyl]imidazolidin-2-one (A38)

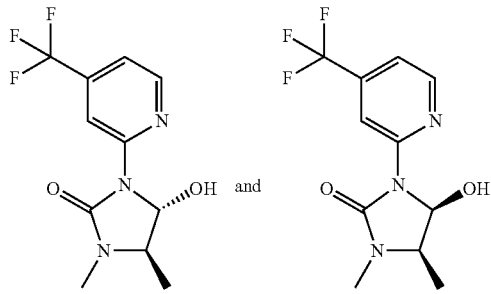 [SMILES: C[C@@H]1[C@@H](O)N(c2cc(C(F)(F)F)ccn2)C(=O)N1C ; C[C@@H]1[C@H](O)N(c2cc(C(F)(F)F)ccn2)C(=O)N1C]

Method as for example 17 but using (2R)-2-(methylamino)propanoic acid (commercially available).
NMR and LC-MS consistant with example 13 (A19).

The diastereomeric ratio was found to vary according to conditions for product synthesis, purification and analysis. The stereochemistry of the chiral centre at the carbon containing the hydroxyl group was found to interconvert at room temperature.

Table 1 lists examples of compounds of the general formula (I)

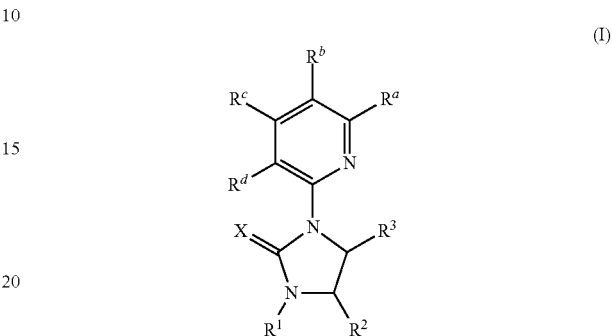

(I)

wherein $R^a$, $R^b$, $R^c$, $R^d$, $R^1$, $R^2$, $R^3$ and X are as defined above.

These compounds were made by the general methods described.

TABLE 1

| Compound | STRUCTURE | 1H NMR (measured in CDCl₃ unless otherwise indicated) δ | LC-MS |
|---|---|---|---|
| A1 | 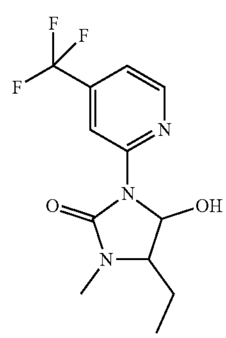 [SMILES: CCC1C(O)N(c2cc(C(F)(F)F)ccn2)C(=O)N1C] | 8.52 (s, 1H), 8.39 (d, 1H), 7.15 (d, 1H), 5.68 (m, 1H), 4.94 (br s, 1H), 3.40 (m, 1H), 2.92 (s, 3H), 1.85 (m, 1H), 1.55 (m, 1H), 0.98 (t, 3H). | positive ES MH+ 290 |
| A2 | 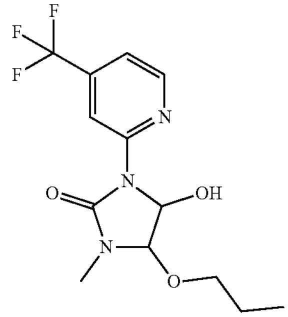 [SMILES: CCCOC1C(O)N(c2cc(C(F)(F)F)ccn2)C(=O)N1C] | 8.47 (s, 1H), 8.38 (d, 1H), 7.18 (dd, 1H), 5.72 (d, 1H), 4.81 (d, 1H), 4.71 (s, 1H), 3.54 (ddq, 2H), 3.00 (s, 3H), 1.65 (m, 2H), 0.96 (t, 3H). | positive ES MH+ 320 |

TABLE 1-continued

| Compound | STRUCTURE | 1H NMR (measured in CDCl₃ unless otherwise indicated) δ | LC-MS |
|---|---|---|---|
| A3 | 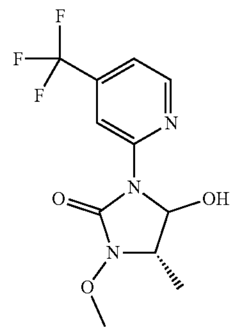 [SMILES: CON1C(=O)N(c2cc(C(F)(F)F)ccn2)C(O)[C@@H]1C] | As for A8 | As for A8 |
| A4 | 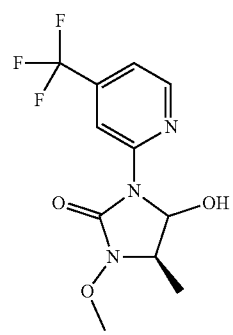 | As for A8 | As for A8 |
| A5 | 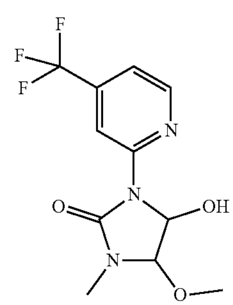 [SMILES: COC1C(O)N(c2cc(C(F)(F)F)ccn2)C(=O)N1C] | 8.46 (s, 1H), 8.39 (d, 1H), 7.19 (d, 1H), 5.74 (d, 1H), 4.82 (d, 1H), 4.67 (s, 1H), 3.43 (s, 3H), 3.01 (s, 3H). | positive ES MH+ 292 |
| A6 | 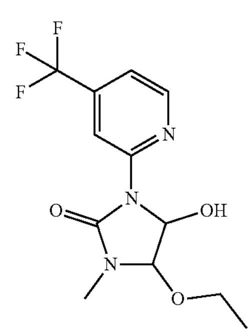 [SMILES: CCOC1C(O)N(c2cc(C(F)(F)F)ccn2)C(=O)N1C] | 8.46 (s, 1H), 8.38 (d, 1H), 7.18 (dd, 1H), 5.73 (d, 1H), 4.82 (d, 1H), 4.71 (s, 1H), 3.66 (m, 2H), 3.00 (s, 3H), 1.28 (t, 3H). | positive ES MH+ 306 |

TABLE 1-continued

| Compound | STRUCTURE | 1H NMR (measured in CDCl₃ unless otherwise indicated) δ | LC-MS |
|---|---|---|---|
| A7 | 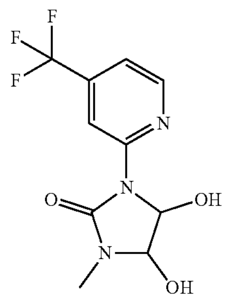 [SMILES: CN1C(=O)N(c2cc(C(F)(F)F)ccn2)C(O)C1O] | Major diastereoisomer: 8.35 (br.s, 1H), 8.32 (d, 1H), 7.12 (dd, 1H), 5.71 (d, 1H); 4.96 (m, 1H), 4.82 (m, 1H), 3.54 (d, 1H), 3.01 (s, 3H). Minor diastereoisomer: 8.47 (br.s, 1H), 8.38 (d, 1H), 7.19 (dd, 1H), 5.89 (d, 1H), 5.15 (m, 1H), 5.12 (m, 1H), 3.82 (d, 1H), 2.97 (s, 3H). | positive ES MH+ 278 |
| A8 | 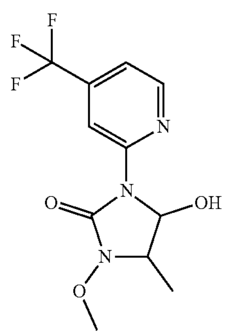 [SMILES: CON1C(=O)N(c2cc(C(F)(F)F)ccn2)C(O)C1C] | Major diastereomer: 8.55 (s, 1H), 8.43 (dd, 1H), 7.25 (d, 1H), 5.55 (m, 1H), 5.04 (very br s, 1H), 3.90 (s, 3H), 3.71 (m, 1H), 1.45 (d, 3H). Minor diastereomer: 8.53 (s, 1H), 8.45 (dd, 1H), 7.24 (d, 1H), 5.87 (d, 1H), 4.60 (very br s, 1H), 3.93 (s, 3H), 3.80 (m, 1H), 1.50 (d, 3H). | positive ES MH+ 292 |
| A9 | 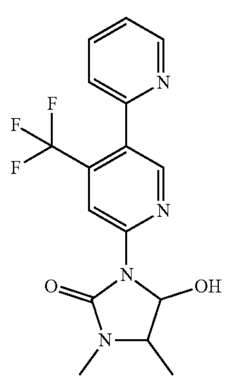 [SMILES: CC1C(O)N(c2cc(C(F)(F)F)c(-c3ccccn3)cn2)C(=O)N1C] | Major diastereomer: 8.72 (m, 1H), 8.67 (s, 1H), 8.42 (s, 1H), 7.78 (t, 1H), 7.45 (d, 1H), 7.35 (dd, 1H), 5.65 (s, 1H), 4.94 (s, 1H), 3.56 (m, 1H), 2.94 (s, 3H), 1.36 (d, 3H). Minor diastereomer: 8.72 (m, 1H), 8.67 (s, 1H), 8.44 (s, 1H), 7.78 (t, 1H), 7.45 (d, 1H), 7.35 (dd, 1H), 5.99 (d, 1H), 4.77 (s, 1H), 3.79 (pentet, 1H), 2.95 (s, 3H), 1.41 (d, 3H). | positive ES MH+ 353 |
| A10 | 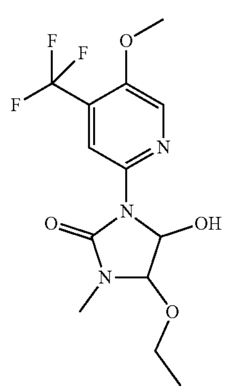 [SMILES: CCOC1C(O)N(c2cc(C(F)(F)F)c(OC)cn2)C(=O)N1C] | 8.36 (s, 1H), 8.03 (s, 1H), 5.66 (s, 1H), 4.80 (br s, 1H), 4.69 (s, 1H), 3.95 (s, 3H), 3.65 (m, 2H), 2.97 (s, 3H), 1.26 (t, 3H). | positive ES MH+ 336 |

TABLE 1-continued

| Compound | STRUCTURE | 1H NMR (measured in CDCl₃ unless otherwise indicated) δ | LC-MS |
|---|---|---|---|
| A11 | 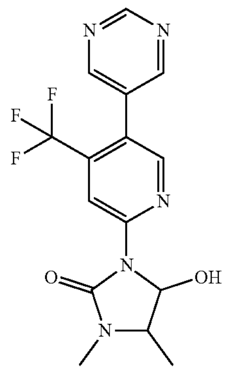 [SMILES: CC1C(O)N(c2cc(C(F)(F)F)c(-c3cncnc3)cn2)C(=O)N1C] | Major diastereomer: 9.30 (s, 1H), 8.75 (s, 1H) 8.72 (s, 2H), 8.24 (s, 1H), 5.65 (m, 1H), 4.80 (m, 1H), 3.55 (m, 1H), 2.96 (s, 3H), 1.35 (d, 3H).<br>Minor diastereomer: 9.30 (s, 1H), 8.75 (s, 1H) 8.72 (s, 2H), 8.24 (s, 1H), 6.00 (d, 1H), 4.65 (s, 1H), 3.85 (m, 1H), 2.92 (s, 3H), 1.42 (d, 3H). | positive ES MH+ 354 |
| A12 | 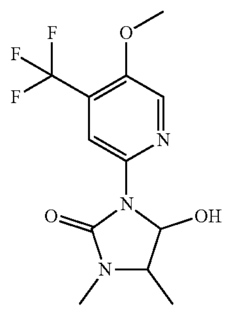 [SMILES: COc1cnc(N2C(=O)N(C)C(C)C2O)cc1C(F)(F)F] | Major diastereomer: 8.45 (s, 1H), 8.03 (s, 1H), 5.53 (m, 1H), 4.90 (br s, 1H), 3.95 (s, 3H), 3.50 (m, 1H), 2.91 (s, 3H), 1.33 (d, 3H).<br>Minor diastereomer: 8.44 (s, 1H), 8.05 (s, 1H), 5.88 (d, 1H), 4.75 (br s, 1H), 3.95 (s, 3H), 3.75 (m, 1H), 2.88 (s, 3H), 1.39 (d, 3H). | positive ES MH+ 306 |
| A13 | 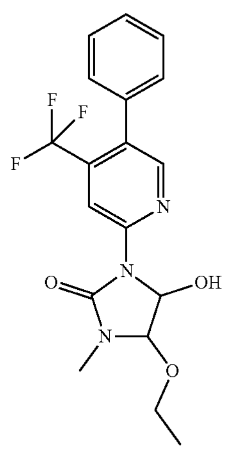 [SMILES: CCOC1C(O)N(c2cc(C(F)(F)F)c(-c3ccccc3)cn2)C(=O)N1C] | 8.56 (s, 1H), 8.23 (s, 1H), 7.44 (m, 3H), 7.32 (m, 2H), 5.77 (d, 1H), 4.81 (d, 1H), 4.74 (s, 1H), 3.66 (m, 2H), 3.03 (s, 3H), 1.28 (m, 3H). | positive ES MH+ 382 |
| A14 | 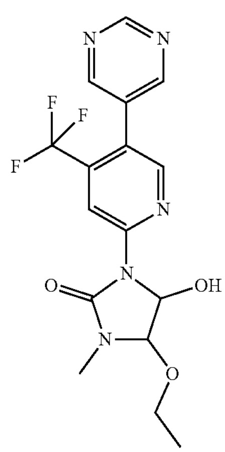 [SMILES: CCOC1C(O)N(c2cc(C(F)(F)F)c(-c3cncnc3)cn2)C(=O)N1C] | 9.30 (s, 1H), 8.75 (s, 2H), 8.70 (s, 1H), 8.24 (s, 1H), 5.80 (d, 1H), 4.75 (s, 1H), 4.71 (d, 1H), 3.69 (m, 2H), 3.04 (s, 3H), 1.29 (t, 3H). | positive ES MH+ 384 |

TABLE 1-continued

| Compound | STRUCTURE | 1H NMR (measured in CDCl₃ unless otherwise indicated) δ | LC-MS |
|---|---|---|---|
| A15 | 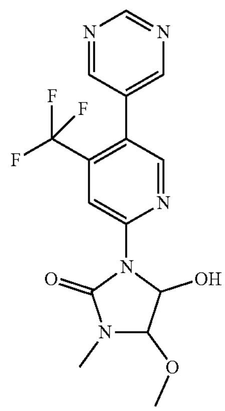 [SMILES: COC1C(O)N(c2cc(C(F)(F)F)c(-c3cncnc3)cn2)C(=O)N1C] | 9.30 (s, 1H), 8.75 (s, 2H), 8.70 (s, 1H), 8.25 (s, 1H), 5.81 (d, 1H), 4.71 (s, 1H), 4.70 (d, 1H), 3.46. (s, 3H), 3.05 (s, 3H). | positive ES MH+ 370 |
| A16 | 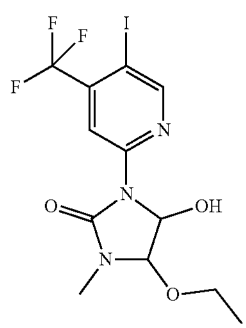 [SMILES: CCOC1C(O)N(c2cc(C(F)(F)F)c(I)cn2)C(=O)N1C] | 8.70 (s, 1H), 8.58 (s, 1H), 5.70 (d, 1H), 4.71 (s, 1H), 4.54 (d, 1H), 3.66 (m, 2H), 3.00 (s, 3H), 1.27 (t, 3H). | positive ES MH+ 432 |
| A17 | 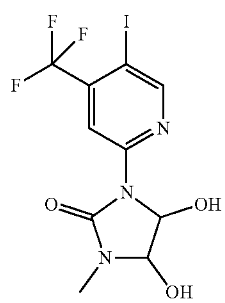 [SMILES: CN1C(=O)N(c2cc(C(F)(F)F)c(I)cn2)C(O)C1O] | 8.81 (s, 1H), 8.62 (s, 1H), 5.65 (d, 1H), 4.84 (d, 1H), 4.81 (d, 1H), 2.91 (s, 3H). | positive ES MH+ 404 |
| A18 | 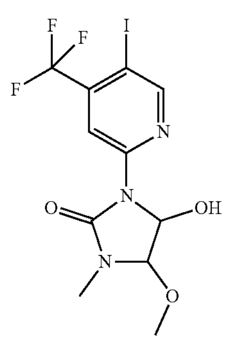 [SMILES: COC1C(O)N(c2cc(C(F)(F)F)c(I)cn2)C(=O)N1C] | 8.70 (s, 1H), 8.57 (s, 1H), 5.71 (d, 1H), 4.66 (s, 1H), 4.58 (d, 1H), 3.43 (s, 3H), 3.00 (s, 3H). | positive ES MH+ 418 |

TABLE 1-continued

| Compound | STRUCTURE | 1H NMR (measured in CDCl₃ unless otherwise indicated) δ | LC-MS |
|---|---|---|---|
| A19 | 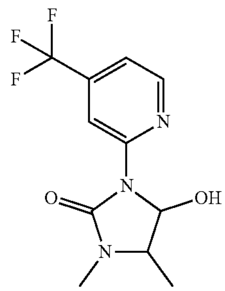 | Major diastereomer: 8.54 (s, 1H), 8.37 (d, 1H), 7.16 (d, 1H), 5.61 (m, 1H), 4.95 (br s, 1H), 3.53 (m, 1H), 2.93 (s, 3H), 1.34 (d, 3H). Minor diastereomer: 8.54 (s, 1H), 8.39 (m, 1H), 7.16 (d, 1H), 5.95 (d, 1H), 4.81 (br s, 1H), 3.76 (pentet, 1H), 2.89 (s, 3H), 1.40 (d, 3H). | positive ES MH+ 276 |
| A20 | 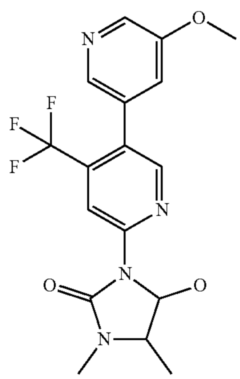 [SMILES: COc1cncc(-c2cnc(N3C(=O)N(C)C(C)C3O)cc2C(F)(F)F)c1] | Major diastereomer: 8.70 (m, 1H), 8.48 (s, 1H), 8.25 (s, 1H), 8.20 (s, 1H), 7.18 (s, 1H), 5.62 (s, 1H), 4.92 (s, 1H), 3.90 (s, 3H), 3.55 (m, 1H), 2.94 (s, 3H), 1.36 (d, 3H). | positive ES MH+ 383 |
| A21 | 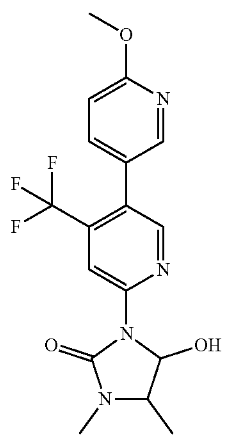 [SMILES: COc1ccc(-c2cnc(N3C(=O)N(C)C(C)C3O)cc2C(F)(F)F)cn1] | Major diastereomer: 8.65 (m, 1H), 8.20 (s, 1H), 8.12 (s, 1H), 7.55 (s, 1H), 6.82 (s, 1H), 5.62 (s, 1H), 4.85 (s, 1H), 3.90 (s, 3H), 3.55 (m, 1H), 2.95 (s, 3H), 1.35 (d, 3H). | positive ES MH+ 383 |
| A22 | 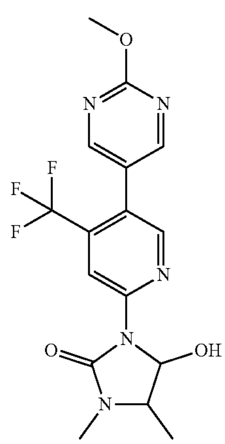 [SMILES: COc1ncc(-c2cnc(N3C(=O)N(C)C(C)C3O)cc2C(F)(F)F)cn1] | Major diastereomer: 8.72 (s, 1H), 8.50 (s, 2H), 8.20 (s, 1H), 5.62 (s, 1H), 4.83 (s, 1H), 4.08 (s, 3H), 3.55 (m, 1H), 2.94 (s, 3H), 1.35 (d, 3H). | positive ES MH+ 384 |

TABLE 1-continued

| Compound | STRUCTURE | 1H NMR (measured in CDCl₃ unless otherwise indicated) δ | LC-MS |
|---|---|---|---|
| A23 | 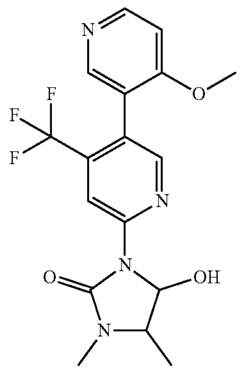 [SMILES: COc1ccncc1-c1cnc(N2C(=O)N(C)C(C)C2O)cc1C(F)(F)F] | Major diastereomer: 8.68 (m, 1H), 8.55 (d, 1H), 8.28 (s, 1H), 8.15 (s, 1H), 6.89 (d, 1H), 5.62 (s, 1H), 4.95 (br s, 1H), 3.70 (s, 3H), 3.54 (m, 1H), 2.95 (s, 3H), 1.35 (d, 3H). | positive ES MH+ 383 |
| A24 | 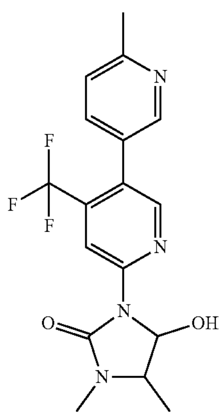 [SMILES: Cc1ccc(-c2cnc(N3C(=O)N(C)C(C)C3O)cc2C(F)(F)F)cn1] | Major diastereomer: 8.69 (s, 1H), 8.46 (s, 1H), 8.21 (m, 1H), 7.57 (dm, 1H), 7.25 (dm, 1H), 5.65 (m, 1H), 4.91 (br s, 1H), 3.56 (m, 1H), 2.95 (s, 3H), 2.64 (s, 3H), 1.36 (d, 3H). Minor diastereomer: 8.69 (s, 1H), 8.46 (s, 1H), 8.21 (m, 1H), 7.57 (dm, 1H), 7.25 (dm, 1H), 6.00 (d, 1H), 4.78 (br s, 1H), 3.79 (m, 1H), 2.92 (s, 3H), 2.64 (s, 3H), 1.42 (d, 3H). | positive ES MH+ 367 |
| A25 | 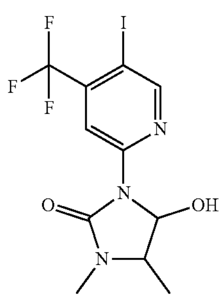 [SMILES: CC1C(O)N(c2cc(C(F)(F)F)c(I)cn2)C(=O)N1C] | Major diastereomer: 8.69 (s, 1H), 8.64 (s, 1H), 5.56 (m, 1H), 4.65 (very br s, 1H), 3.53 (m, 1H), 2.93 (s, 3H), 1.33 (d, 3H). Minor diastereomer: 8.70 (s, 1H), 8.64 (s, 1H), 5.91 (d, 1H), 4.65 (very br s, 1H), 3.76 (m, 1H), 2.88 (s, 3H), 1.38 (d, 3H). | positive ES MH+ 402 |
| A26 | 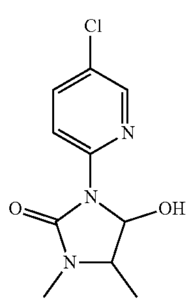 [SMILES: CC1C(O)N(c2ccc(Cl)cn2)C(=O)N1C] | Major diastereomer 8.32 (s, 1H), 8.16 (d, 1H), 7.86 (d, 1H), 6.43 (d, 1H), 5.58 (d, 1H), 3.37 (m, 1H), 2.80 (s, 3H), 1.18 (d, 3H). Minor diastereomer 8.32 (s, 1H), 8.17 (d, 1H), 7.86 (d, 1H), 6.18 (d, 1H), 5.91 (d, 1H), 3.39 (m, 1H), 2.72 (s, 3H), 1.18 (d, 3H). | Positive ES MH+ 242 |

TABLE 1-continued

| Compound | STRUCTURE | 1H NMR (measured in CDCl$_3$ unless otherwise indicated) δ | LC-MS |
|---|---|---|---|
| A27 | 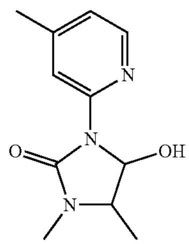 [SMILES: Cc1ccnc(N2C(=O)N(C)C(C)C2O)c1] | Major diastereomer 8.48 (s, 1H), 8.15 (d, 1H), 7.05 (d, 1H), 5.79 (d, 1H), 3.65 (m, 1H), 2.97 (s, 3H), 2.5 (s, 3H), 1.4 (d, 3H). Minor diastereomer 8.58 (s, 1H), 8.16 (d, 1H), 7.07 (d, 1H), 6.21 (d, 1H), 3.88 (m, 1H), 2.94 (s, 3H), 2.55 (s, 3H), 1.45 (d, 3H). | Positive ES MH+ 222 |
| A28 | 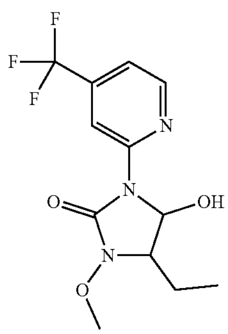 | Major diastereomer 8.55 (s, 1H), 8.43 (dd, 1H), 7.25 (d, 1H), 5.55 (d, 1H), 5.04 (very br s, 1H), 3.90 (s, 3H), 3.38 (d, 1H), 1.45 (d, 3H). Minor diastereomer 8.53 (s, 1H), 8.45 (dd, 1H), 7.24 (d, 1H), 5.87 (d, 1H), 4.60 (very br s, 1H), 3.93 (s, 3H), 3.71 (m, 1H), 1.50 (d, 3H). | positive ES MH+ 306 |
| A29 | 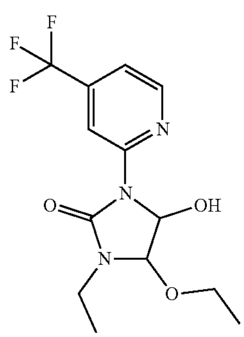 [SMILES: CCOC1C(O)N(c2cc(C(F)(F)F)ccn2)C(=O)N1CC] | 8.46 (s, 1H), 8.38 (d, 1H), 7.18 (dd, 1H), 5.74 (d, 1H), 4.80 (d, 1H), 4.79 (s, 1H), 3.51-3.73 (m, 3H), 3.33 (m, 1H), 1.27 (t, 3H), 1.25 (t, 3H). | positive ES MH+ 320 |
| A30 | 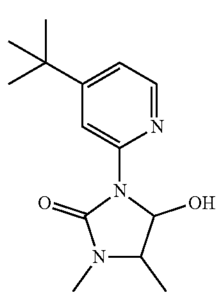 [SMILES: CC1C(O)N(c2cc(C(C)(C)C)ccn2)C(=O)N1C] | Major diastereomer 8.17 (d, 1H), 8.04 (d, 1H), 6.91 (d, 1H), 5.50 (d, 1H), 3.41 (m, 1H), 2.84 (s, 3H), 1.31 (d, 3H), 1.24 (s, 9H). Minor diastereomers 8.17 (d, 1H), 8.05 (d, 1H), 6.92 (d, 1H), 5.85 (d, 1H), 3.63 (m, 1H), 2.80 (s, 3H), 1.31 (d, 3H), 1.27 (s, 9H). | Positive ES MH+ 264 |
| A31 | 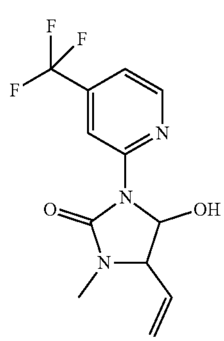 [SMILES: C=CC1C(O)N(c2cc(C(F)(F)F)ccn2)C(=O)N1C] | Major diastereomer: 8.54 (s, 1H), 8.37 (d, 1H), 7.17 (m, 1H), 5.75 (ddd, 1H), 5.70 (d, 1H), 5.44 (m, 1H), 5.43 (m, 1H), 5.01 (br s, 1H), 3.89 (m, 1H), 2.89 (s, 3H). Minor diastereomer: 8.54 (s, 1H), 8.39 (m, 1H), 7.17 (m, 1H), 6.02 (m, 2H), 5.51 (m, 2H), 4.06 (m, 1H), 2.83 (s, 3H). | positive ES MH+ 288 |

TABLE 1-continued

| Compound | STRUCTURE | 1H NMR (measured in CDCl₃ unless otherwise indicated) δ | LC-MS |
|---|---|---|---|
| A32 | 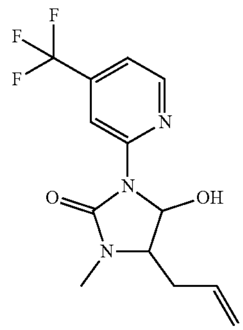 [SMILES: C=CCC1C(O)N(c2cc(C(F)(F)F)ccn2)C(=O)N1C] | Major diastereomer: 8.15 (s, 1H), 8.37 (d, 1H), 7.15 (dd, 1H), 5.75 (m, 1H), 5.70 (d, 1H), 5.23 (dd, 1H), 5.20 (dd, 1H), 4.90 (d, 1H), 3.54 (ddd, 1H), 2.96 (s, 3H), 2.55 (m, 1H), 2.53 (m, 1H). Minor diastereomer: 8.15 (s, 1H), 8.37 (d, 1H), 7.15 (dd, 1H), 5.98 (m, 1H), 5.70 (d, 1H), 5.26 (dd, 1H), 5.18 (d, 1H), 4.79 (br.s, 1H), 3.65 (ddd, 1H), 2.91 (s, 3H), 2.69 (m, 1H), 2.55 (m, 1H). | positive ES MH+ 302 |
| A33 | 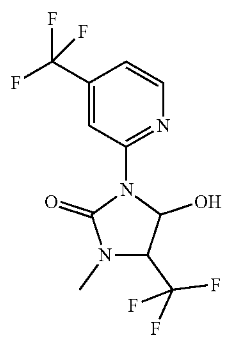 [SMILES: CN1C(=O)N(c2cc(C(F)(F)F)ccn2)C(O)C1C(F)(F)F] | 8.48 (s, 1H), 8.42 (d, 1H), 7.25 (d, 1H), 6.02 (m, 1H), 5.01 (br s, 1H), 3.93 (m, 1H), 3.10 (s, 3H). | positive ES MH+ 330 |
| A34 | 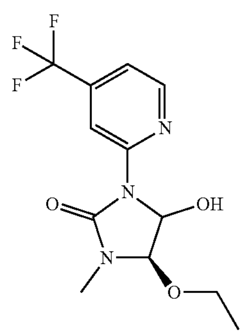 [SMILES: CCO[C@@H]1C(O)N(c2cc(C(F)(F)F)ccn2)C(=O)N1C] | As for A6 | As for A6 |
| A35 | 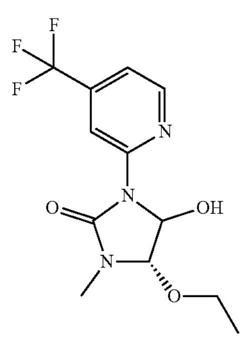 [SMILES: CCO[C@H]1C(O)N(c2cc(C(F)(F)F)ccn2)C(=O)N1C] | As for A6 | As for A6 |

TABLE 1-continued

| Compound | STRUCTURE | 1H NMR (measured in CDCl₃ unless otherwise indicated) δ | LC-MS |
|---|---|---|---|
| A36 | 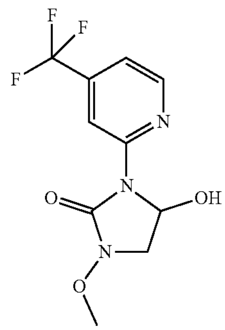 [SMILES: CON1CC(O)N(c2cc(C(F)(F)F)ccn2)C1=O] | 8.54 (s, 1H), 8.45 (dd, 1H), 7.25 (d, 1H), 6.02 (m, 1H), 4.75 (very br s, 1H), 3.89 (s, 3H), 3.75 (m, 1H), 3.68 (m, 1H). | positive ES MH+ 278 |
| A37 | 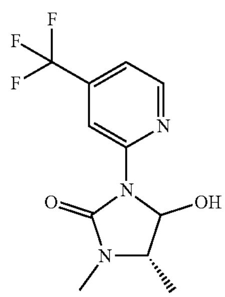 | As for A19 | As for A19 |
| A38 | 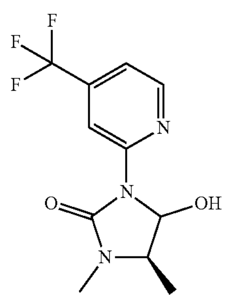 [SMILES: C[C@@H]1C(O)N(c2cc(C(F)(F)F)ccn2)C(=O)N1C] | As for A19 | As for A19 |
| A39 | 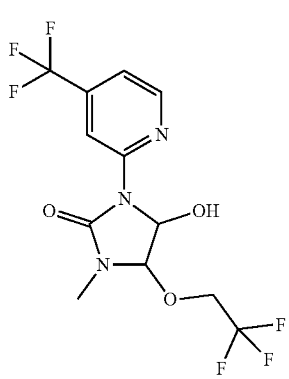 [SMILES: CN1C(=O)N(c2cc(C(F)(F)F)ccn2)C(O)C1OCC(F)(F)F] | 8.44 (s, 1H), 8.40 (d, 1H), 7.22 (d, 1H), 5.77 (d, 1H), 4.86 (s, 1H), 4.85 (d, 1H), 3.99 (m, 2H), 3.03 (s, 3H). | positive ES MH+ 360 |

TABLE 1-continued

| Compound | STRUCTURE | 1H NMR (measured in CDCl₃ unless otherwise indicated) δ | LC-MS |
|---|---|---|---|
| A40 | 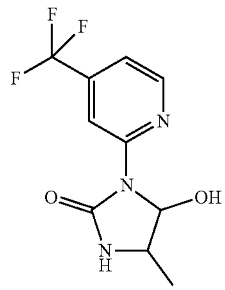 [SMILES: CC1NC(=O)N(c2cc(C(F)(F)F)ccn2)C1O] | (DMSO-d6): 8.57 (d, 1H), 8.47 (s, 1H), 7.75 (s, 1H), 7.36 (d, 1H), 6.46 (d, 1H), 5.68 (d, 1H), 3.43 (q, 1H), 1.15 (d, 3H). | positive ES MH+ 262 |
| A41 | 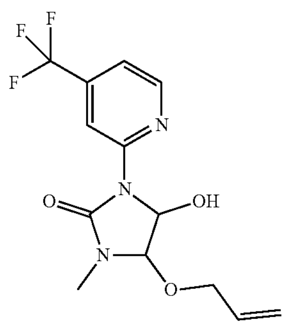 [SMILES: C=CCOC1C(O)N(c2cc(C(F)(F)F)ccn2)C(=O)N1C] | 8.46 (s, 1H), 8.38 (d, 1H), 7.19 (dd, 1H), 5.94 (m, 1H), 5.75 (d, 1H), 5.36 (dd, 1H), 5.26 (dd, 1H), 4.80 (d, 1H), 4.77 (s, 1H), 4.15 (m, 2H), 3.01 (s, 3H). | positive ES MH+ 318 |
| A42 | 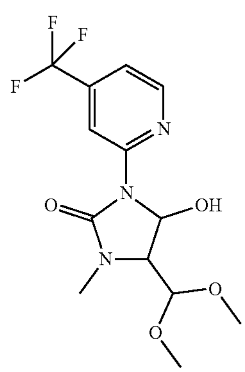 [SMILES: COC(OC)C1C(O)N(c2cc(C(F)(F)F)ccn2)C(=O)N1C] | 8.50 (s, 1H), 8.37 (d, 1H), 7.16 (d, 1H), 5.89 (s, 1H), 4.90 (s, 1H), 4.37 (d, 1H), 3.57 (m, 1H), 3.49 (d, 6H), 3.04 (s, 3H). | positive ES MH+ 336 |
| A43 | 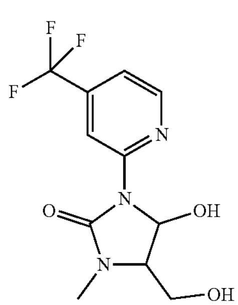 [SMILES: CN1C(=O)N(c2cc(C(F)(F)F)ccn2)C(O)C1CO] | Major diastereomer: 8.50 (s, 1H), 8.37 (d, 1H), 7.16 (d, 1H), 5.89 (m, 1H), 5.03 (m, 1H), 3.91 (m, 1H), 3.82 (m, 1H), 3.51 (q, 1H), 2.96 (s, 3H), 2.36 (br m, 1H) Minor diastereomer: 8.55 (s, 1H), 8.37 (d, 1H), 7.18 (m, 1H), 5.89 (m, 1H), 5.46 (br s, 1H), 3.96 (m, 1H), 3.76 (m, 1H), 3.51 (q, 1H), 2.96 (s, 3H), 2.36 (br m, 1H) | positive ES MH+ 292 |

TABLE 1-continued

| Compound | STRUCTURE | 1H NMR (measured in CDCl₃ unless otherwise indicated) δ | LC-MS |
|---|---|---|---|
| A44 | 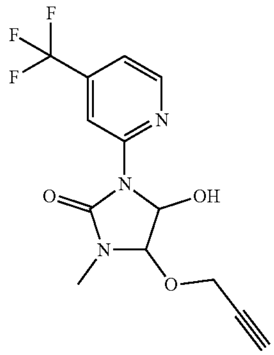 [SMILES: C#CCOC1C(O)N(c2cc(C(F)(F)F)ccn2)C(=O)N1C] | 8.44 (s, 1H), 8.38 (d, 1H), 7.19 (dd, 1H), 5.82 (d, 1H), 4.92 (s, 1H), 4.79 (d, 1H), 4.32 (d, 2H), 3.03 (s, 3H), 2.54 (t, 1H) | positive ES MH+ 316 |
| A45 | 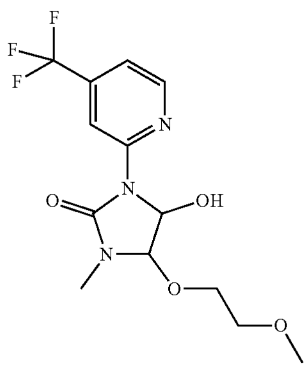 [SMILES: COCCOC1C(O)N(c2cc(C(F)(F)F)ccn2)C(=O)N1C] | 8.45 (s, 1H), 8.38 (d, 1H), 7.18 (d, 1H), 5.77 (d, 1H), 4.80 (s, 1H), 4.78 (d, 1H), 3.74 (q, 2H), 3.58 (t, 2H), 3.39 (s, 3H), 3.01 (s, 3H). | positive ES MH+ 336 |
| A46 | 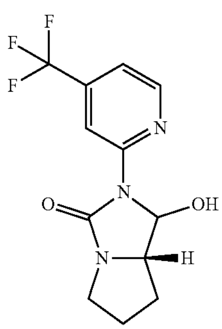 [SMILES: O=C1N(c2cc(C(F)(F)F)ccn2)C(O)[C@@H]2CCCN12] | 8.62 (s, 1H), 8.42 (d, 1H), 7.20 (dd, 1H), 5.92 (t, 1H), 4.98 (d, 1H), 3.68-3.77 (m, 2H), 3.21-3.29 (m, 1H), 2.14-2.22 (m, 1H), 2.02-2.13 (m, 1H), 1.89-2.02 (m, 1H), 1.36-1.49 (m, 1H). | positive ES MH+ 288 |
| A47 | 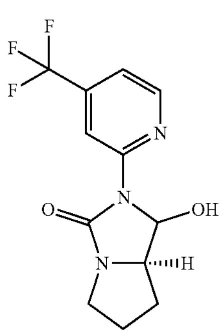 [SMILES: O=C1N(c2cc(C(F)(F)F)ccn2)C(O)[C@H]2CCCN12] | As for A46 | As for A46 |

TABLE 1-continued

| Compound | STRUCTURE | 1H NMR (measured in CDCl₃ unless otherwise indicated) δ | LC-MS |
|---|---|---|---|
| A48 | 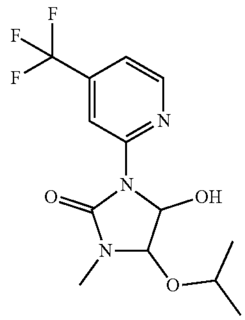 [SMILES: CC(C)OC1C(O)N(c2cc(C(F)(F)F)ccn2)C(=O)N1C] | 8.46 (s, 1H), 8.37 (d, 1H), 7.17 (d, 1H), 5.66 (d, 1H), 4.80 (d, 1H), 4.71 (s, 1H), 3.93 (dt, 1H), 2.96 (s, 3H), 1.27 (dd, 6H). | positive ES MH+ 320 |
| A49 | 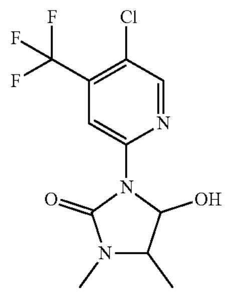 [SMILES: CC1C(O)N(c2cc(C(F)(F)F)c(Cl)cn2)C(=O)N1C] | Major diastereomer: 8.64 (s, 1H), 8.33 (s, 1H), 5.56 (t, 1H), 4.63 (d, 1H), 3.52 (m, 1H), 2.93 (s, 3H), 1.34 (d, 3H). Minor diastereomer: 8.64 (s, 1H), 8.35 (s, 1H), 5.91 (dd, 1H), 4.46 (d, 1H), 3.76 (m, 1H), 2.89 (s, 3H), 1.39 (d, 3H). | positive ES MH+ 310 |
| A50 | 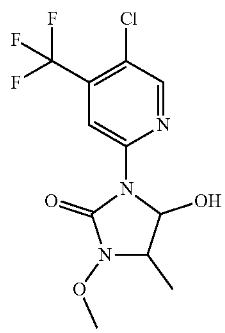 [SMILES: CON1C(=O)N(c2cc(C(F)(F)F)c(Cl)cn2)C(O)C1C] | Major diastereomer: 8.64 (s, 1H), 8.38 (s, 1H), 5.51 (dd, 1H), 4.68 (d, 1H), 3.89 (s, 3H), 3.72 (m, 1H), 1.45 (d, 3H). Minor diastereomer: 8.62 (s, 1H), 8.40 (s, 1H), 5.83 (dd, 1H), 4.28 (d, 1H), 3.92 (s, 3H), 3.79 (m, 1H), 1.50 (d, 3H). | positive ES MH+ 326 |
| A51 | 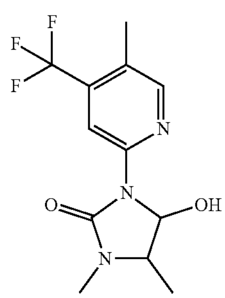 [SMILES: Cc1cnc(N2C(=O)N(C)C(C)C2O)cc1C(F)(F)F] | Major diastereomer 8.48 (s, 1H), 8.15 (s, 1H), 5.56 (d, 1H), 4.98 (br s, 1H), 3.51 (dq, 1H), 2.92 (s, 3H), 2.40 (s, 3H), 1.33 (d, 3H). Minor diastereomer 8.47 (s, 1H), 8.17 (s, 1H), 5.91 (d, 1H), 4.83 (br s, 1H), 3.74 (pentet, 1H), 2.88 (s, 3H), 2.40 (s, 3H), 1.39 (d, 3H). | positive ES MH+ 290 |
| A52 | 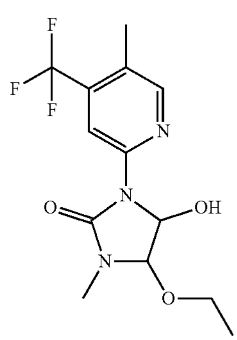 [SMILES: CCOC1C(O)N(c2cc(C(F)(F)F)c(C)cn2)C(=O)N1C] | 8.41 (s, 1H), 8.17 (s, 1H), 5.70 (s, 1H), 4.70 (s, 1H), 3.64 (m, 2H), 3.00 (s, 3H), 2.40 (s, 3H), 1.27 (t, 3H). | positive ES MH+ 320 |

TABLE 1-continued

| Compound | STRUCTURE | 1H NMR (measured in CDCl₃ unless otherwise indicated) δ | LC-MS |
|---|---|---|---|
| A53 | 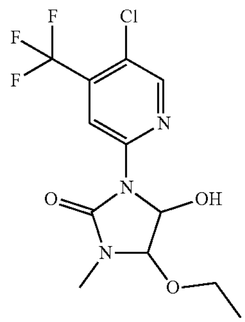 [SMILES: CCOC1C(O)N(c2cc(C(F)(F)F)c(Cl)cn2)C(=O)N1C] | 8.57 (s, 1H), 8.34 (s, 1H), 5.70 (d, 1H), 4.70 (s, 1H), 4.52 (d, 1H), 3.67 (m, 2H), 3.00 (s, 3H), 1.28 (t, 3H). | positive ES MH+ 340 |
| A54 | 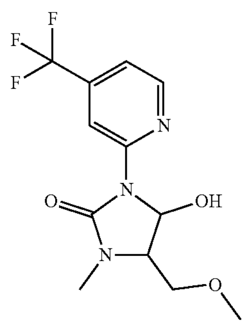 [SMILES: COCC1C(O)N(c2cc(C(F)(F)F)ccn2)C(=O)N1C] | 8.55 (s, 1H), 8.39 (d, 1H), 7.17 (d, 1H), 5.82 (s, 1H), 3.58 (br s, 3H), 3.39 (s, 3H), 2.98 (s, 3H). | positive ES MH+ 306 |
| A55 | 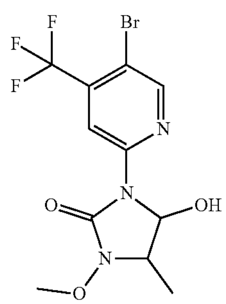 [SMILES: CON1C(=O)N(c2cc(C(F)(F)F)c(Br)cn2)C(O)C1C] | Major diastereomer 8.63 (s, 1H), 8.54 (s, 1H), 5.83 (d, 1H), 4.30 (br s, 1H), 3.93 (s, 3H), 3.80 (m, 1H), 1.50 (d, 3H). Minor diastereomer 8.65 (s, 1H), 8.52 (s, 1H), 5.51 (d, 1H), 4.70 (br s, 1H), 3.90 (s, 3H), 3.72 (m, 1H), 1.45 (d, 3H). | positive ES MH+ 370/372 |
| A56 | 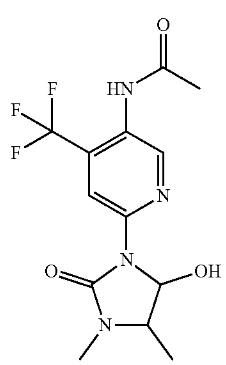 [SMILES: CC(=O)Nc1cnc(N2C(=O)N(C)C(C)C2O)cc1C(F)(F)F] | Major diastereomer 8.85 (s, 1H), 8.53 (s, 1H), 7.22 (br s, 1H), 5.60 (m, 1H), 4.84 (br s, 1H), 3.53 (m, 1H), 2.92 (s, 3H), 2.23 (s, 3H), 1.33 (d, 3H). Minor diastereomer 8.85 (s, 1H), 8.52 (s, 1H), 7.22 (br s, 1H), 5.93 (m, 1H), 4.70 (br s, 1H), 3.75 (m, 1H), 2.88 (s, 3H), 2.23 (s, 3H), 1.39 (d, 3H). | positive ES MH+ 333 |

TABLE 1-continued

| Compound | STRUCTURE | 1H NMR (measured in CDCl₃ unless otherwise indicated) δ | LC-MS |
|---|---|---|---|
| A57 | 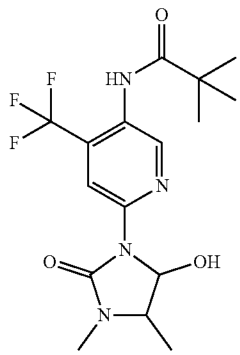 [SMILES: CC1C(O)N(c2cc(C(F)(F)F)c(NC(=O)C(C)(C)C)cn2)C(=O)N1C] | Major diastereomer 8.95 (s, 1H), 8.53 (s, 1H), 7.48 (br s, 1H), 5.60 (m, 1H), 4.86 (m, 1H), 3.52 (m, 1H), 2.92 (s, 3H), 1.33 (d, 3H), 1.33 (s, 9H).<br>Minor diastereomer 8.97 (s, 1H), 8.52 (s, 1H), 7.48 (br s, 1H), 5.94 (m, 1H), 4.71 (m, 1H), 3.75 (m, 1H), 2.88 (s, 3H), 1.39 (d, 3H), 1.33 (s, 9H). | positive ES MH+ 375 |
| A58 | 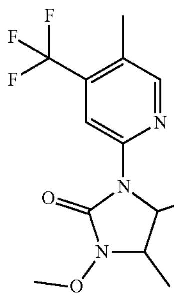 | Major diastereomer 8.50 (s, 1H), 8.20 (s, 1H), 5.50 (m, 1H), 5.02 (m, 1H), 3.89 (s, 3H), 3.68 (m, 1H), 2.41 (s, 3H), 1.44 (d, 3H).<br>Minor diastereomer 8.47 (s, 1H), 8.23 (s, 1H), 5.81 (m, 1H), 4.59 (m, 1H), 3.93 (s, 3H), 3.76 (quintet, 1H), 2.41 (s, 3H), 1.48 (d, 3H). | positive ES MH+ 306 |
| A59 | 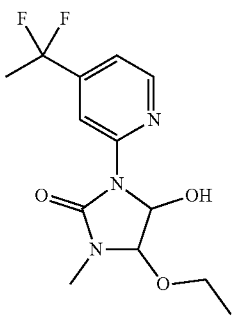 [SMILES: CCOC1C(O)N(c2cc(C(C)(F)F)ccn2)C(=O)N1C] | 8.28 (m, 2H), 7.10 (dd, 1H), 5.72 (d, 1H), 5.00 (d, 1H), 4.71 (s, 1H), 3.66 (m, 2H), 2.99 (s, 3H), 1.91 (t, 3H), 1.27 (t, 3H). | positive ES MH+ 302 |
| A60 | 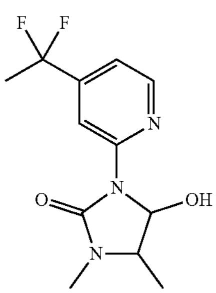 [SMILES: CC1C(O)N(c2cc(C(C)(F)F)ccn2)C(=O)N1C] | Major diastereomer: 8.36 (d, 1H), 8.30 (d, 1H), 7.09 (dd, 1H), 5.59 (m, 1H), 5.12 (d, 1H), 3.51 (m, 1H), 2.93 (s, 3H), 1.92 (t, 3H), 1.33 (d, 3H).<br>Minor diastereomer: 8.36 (d, 1H), 8.30 (d, 1H), 7.09 (dd, 1H), 5.92 (m, 1H), 4.98 (d, 1H), 3.74 (m, 1H), 2.89 (s, 3H), 1.92 (t, 3H), 1.40 (d, 3H). | positive ES MH+ 272 |
| A61 | 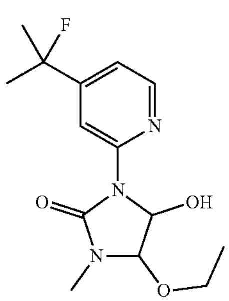 [SMILES: CCOC1C(O)N(c2cc(C(C)(C)F)ccn2)C(=O)N1C] | 8.21 (d, 1H), 8.06 (m, 1H), 7.07 (dd, 1H), 5.71 (s, 1H), 5.19 (s, 1H), 4.70 (s, 1H), 3.65 (m, 2H), 2.98 (s, 3H), 1.70 (d, 3H), 1.63 (d, 3H), 1.27 (t, 3H). | positive ES MH+ 298 |

TABLE 1-continued

| Compound | STRUCTURE | 1H NMR (measured in CDCl₃ unless otherwise indicated) δ | LC-MS |
|---|---|---|---|
| A62 | 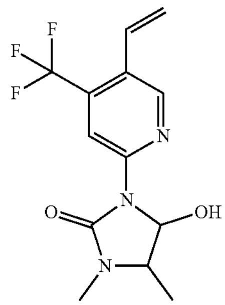 [SMILES: C=Cc1cnc(N2C(=O)N(C)C(C)C2O)cc1C(F)(F)F] | Major diastereomer: 8.51 (s, 1H), 8.50 (s, 1H), 6.93 (m, 1H), 5.71 (d, 1H), 5.60 (m, 1H), 5.42 (d, 1H), 4.91 (m, 1H), 3.53 (m, 1H), 2.93 (s, 3H), 1.33 (d, 3H). Minor diastereomer: 8.51 (s, 1H), 8.50 (s, 1H), 6.93 (m, 1H), 5.94 (m, 1H), 5.71 (d, 1H), 5.42 (d, 1H), 4.76 (m, 1H), 3.76 (m, 1H), 2.88 (s, 3H), 1.39 (d, 3H). | positive ES MH+ 302 |
| A63 | 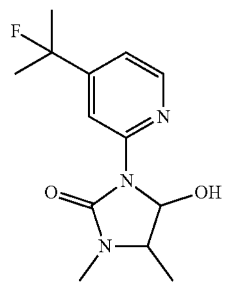 [SMILES: CC1C(O)N(c2cc(C(C)(C)F)ccn2)C(=O)N1C] | Major diastereomer 8.15 (d, 1H), 8.11 (m, 1H), 7.01 (dd, 1H), 5.54 (d, 1H), 3.46 (m, 1H), 2.88 (s, 3H), 1.66 (d, 3H), 1.60 (d, 3H), 1.28 (d, 3H). Minor diastereomer 8.15 (d, 1H), 8.11 (m, 1H), 7.01 (dd, 1H), 5.88 (d, 1H), 3.68 (m, 1H), 2.83 (s, 3H), 1.66 (d, 3H), 1.60 (d, 3H), 1.34 (d, 3H). | positive ES MH+ 268 |
| A64 | 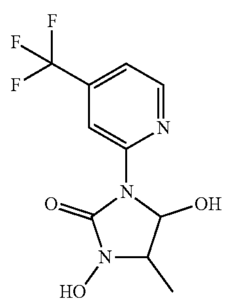 [SMILES: CC1C(O)N(c2cc(C(F)(F)F)ccn2)C(=O)N1O] | Major diastereomer: 8.47 (s, 1H), 8.42 (d, 1H), 7.25 (m, 1H), 5.57 (d, 1H), 3.73 (m, 1H), 1.47 (d, 3H). Minor diastereomer: 8.44 (s, 1H), 8.35 (d, 1H), 7.27 (m, 1H), 5.94 (d, 1H), 3.86 (m, 1H), 1.48 (d, 3H). | positive ES MH+ 278 |
| A65 | 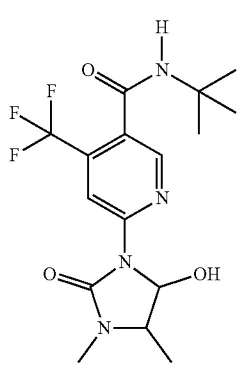 [SMILES: CC1C(O)N(c2cc(C(F)(F)F)c(C(=O)NC(C)(C)C)cn2)C(=O)N1C] | Major diastereomer: 8.58 (s, 1H), 8.46 (s, 1H), 5.63 (br. s., 1H), 4.77 (d, 1H), 4.12 (m, 1H), 3.54 (qd, 1H), 2.94 (s, 3H), 1.46 (s, 9H) 1.35 (d, 3H). Minor diastereomer: 8.58 (s, 1H), 8.46 (s, 1H), 5.95 (dd, 1H), 5.60 (t, 1H), 4.60 (d, 1H), 3.78 (t, 1H), 2.90 (s, 3H), 1.46 (s, 9H) 1.35 (d, 3H). | positive ES MH+ |

TABLE 1-continued

| Compound | STRUCTURE | 1H NMR (measured in CDCl₃ unless otherwise indicated) δ | LC-MS |
| --- | --- | --- | --- |
| A66 | 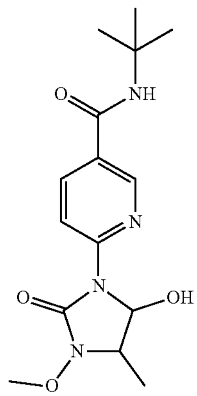 [SMILES: CON1C(=O)N(c2ccc(C(=O)NC(C)(C)C)cn2)C(O)C1C] | Major diastereomer: 8.65 (d, 1H), 8.26 (dd, 1H), 8.02 (t, 1H), 5.87 (br.s, 1H), 5.53 (d, 1H), 5.20 (br.s, 1H), 3.89 (s, 3H), 3.70 (m, 1H), 1.48 (s, 9H), 1.45 (d, 3H). Minor diastereomer: 8.67 (d, 1H), 8.24 (dd, 1H), 8.00 (t, 1H), 5.87 (br.s, 1H), 5.85 (d, 1H), 4.75 (br.s, 1H), 3.92 (s, 3H), 3.78 (m, 1H), 1.50 (d, 3H), 1.48 (s, 9H). | positive ES MH+ 323 |
| A67 | 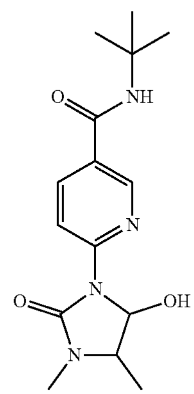 [SMILES: CC1C(O)N(c2ccc(C(=O)NC(C)(C)C)cn2)C(=O)N1C] | Major diastereomer: 8.62 (d, 1H), 8.25 (d, 1H), 7.96 (dd, 1H), 5.84 (br.s, 1H), 5.59 (t, 1H), 5.11 (d, 1H), 3.51 (ddd, 1H), 2.92 (s, 3H), 1.48 (s, 9H), 1.34 (d, 3H). Minor diastereomer: 8.62 (d, 1H), 8.25 (d, 1H); 7.96 (dd, 1H), 5.94 (dd, 1H), 5.84 (br.s, 1H), 4.96 (d, 1H), 3.75 (m, 1H), 2.88 (s, 3H), 1.48 (s, 9H), 1.38 (d, 3H). | positive ES MH+ 307 |
| A68 | 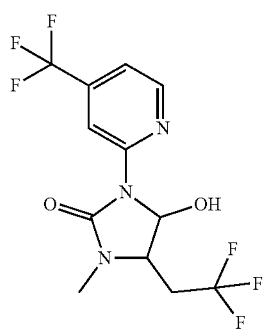 [SMILES: CN1C(=O)N(c2cc(C(F)(F)F)ccn2)C(O)C1CC(F)(F)F] | Major diastereomer: 8.44 (d, 1H), 7.98 (s, 1H), 7.26 (dd, 1H), 5.81 (m, 1H), 5.12 (d, 1H), 4.13 (m, 1H), 3.18 (d, 3H), 2.65-2.36 (m, 2H). Minor diastereomer: 8.46 (d, 1H), 8.29 (s, 1H), 7.28 (dd, 1H), 5.72 (m, 1H), 5.40 (t, 1H), 4.00 (m, 1H), 3.18 (d, 3H), 2.65-2.36 (m, 2H). | positive ES MH+ 344 |
| A69 | 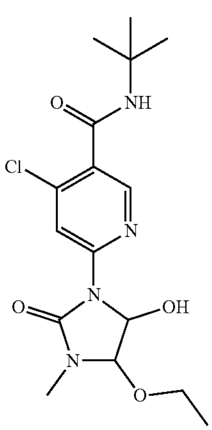 [SMILES: CCOC1C(O)N(c2cc(Cl)c(C(=O)NC(C)(C)C)cn2)C(=O)N1C] | 8.58 (s, 1H), 8.24 (s, 1H), 6.20 (brs, 1H), 5.71 (s, 1H), 4.79 (brs, 1H), 4.69 (s, 1H), 3.68 (m, 2H), 2.99 (s, 3H), 1.48 (s, 9H), 1.28 (t, 3H). | positive ES MH+ 371 |

TABLE 1-continued

| Compound | STRUCTURE | 1H NMR (measured in CDCl₃ unless otherwise indicated) δ | LC-MS |
|---|---|---|---|
| A70 | 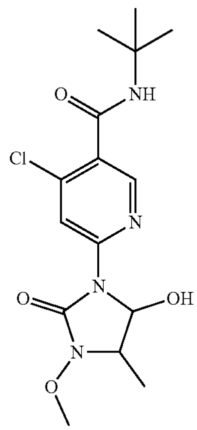 [SMILES: CON1C(=O)N(c2cc(Cl)c(C(=O)NC(C)(C)C)cn2)C(O)C1C] | Major diastereomer: 8.59 (s, 1H), 8.34 (s, 1H), 6.15 (s, 1H), 5.53 (d, 1H), 3.90 (s, 3H), 3.72 (m, 1H), 1.49 (s, 9H), 1.46 (d, 3H). Minor diastereomer: 8.59 (s, 1H), 8.34 (s, 1H), 6.15 (s, 1H), 5.85 (d, 1H), 3.93 (s, 3H), 3.79 (m, 1H), 1.49 (s, 9H), 1.46 (d, 3H). | positive ES MH+ 357 |
| A71 | 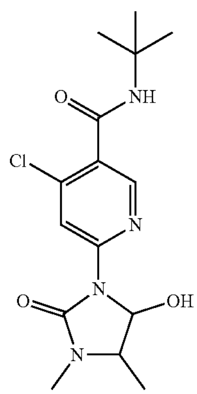 [SMILES: CC1C(O)N(c2cc(Cl)c(C(=O)NC(C)(C)C)cn2)C(=O)N1C] | Major diastereomer: 8.52 (s, 1H), 8.27 (s, 1H), 6.28 (s, 1H), 5.56 (d, 1H), 4.98 (brs, 1H), 3.51 (m, 1H), 2.91 (s, 3H), 1.47 (s, 9H), 1.32 (d, 3H). Minor diastereomer: 8.52 (s, 1H), 8.27 (s, 1H), 6.28 (s, 1H), 5.91 (d, 1H), 4.80 (brs, 1H), 3.73 (m, 1H), 2.87 (s, 3H), 1.47 (s, 9H), 1.37 (d, 3H). | positive ES MH+ 341 |
| A72 | 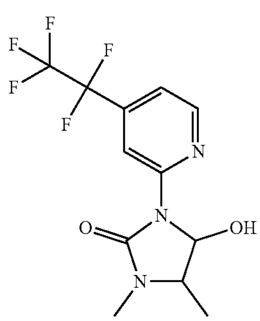 [SMILES: CC1C(O)N(c2cc(C(F)(F)C(F)(F)F)ccn2)C(=O)N1C] | Major diastereomer 8.37 (s, 1H), 8.30 (d, 1H), 7.11 (dd, 1H), 5.59 (d, 1H), 5.51 (brs, 1H), 3.53 (m, 1H), 2.93 (s, 3H), 1.33 (d, 3H). Minor diastereomer 8.37 (s, 1H), 8.30 (d, 1H), 7.11 (dd, 1H), 5.93 (d, 1H), 5.51 (brs, 1H), 3.73 (m, 1H), 2.89 (s, 3H), 1.40 (d, 3H). | positive ES MH+ 326 |
| A73 | 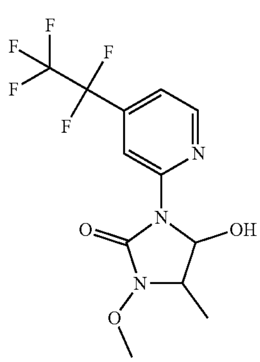 [SMILES: CON1C(=O)N(c2cc(C(F)(F)C(F)(F)F)ccn2)C(O)C1C] | Major diastereomer: 8.57 (s, 1H), 8.46 (d, 1H), 7.26 (m, 1H), 5.58 (d, 1H), 5.03 (brs, 1H), 3.92 (s, 3H), 3.74 (m, 1H), 1.47 (d, 3H). Minor diastereomer: 8.55 (s, 1H), 8.47 (d, 1H), 7.26 (m, 1H), 5.89 (d, 1H), 5.03 (brs, 1H), 3.95 (s, 3H), 3.81 (m, 1H), 1.51 (d, 3H). | positive ES MH+ 342 |

TABLE 1-continued

| Compound | STRUCTURE | 1H NMR (measured in CDCl₃ unless otherwise indicated) δ | LC-MS |
|---|---|---|---|
| A74 | 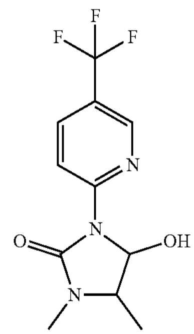 [SMILES: CC1C(O)N(c2ccc(C(F)(F)F)cn2)C(=O)N1C] | Major diastereomer: 8.49 (m, 1H), 8.36 (d, 1H), 7.88 (dd, 1H), 5.60 (d, 1H), 4.94 (br.s, 1H), 3.53 (ddd, 1H), 2.93 (s, 3H), 1.34 (d, 3H). Minor diastereomer: 8.49 (m, 1H), 8.36 (d, 1H), 7.88 (dd, 1H), 5.96 (d, 1H), 4.78 (br.s, 1H), 3.77 (pent, 1H), 2.89 (s, 3H), 1.40 (d, 3H). | positive ES MH+ 276 |
| A75 | 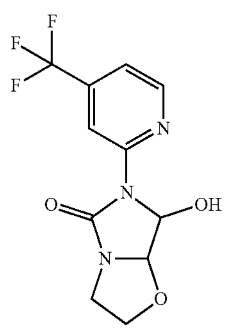 [SMILES: O=C1N2CCOC2C(O)N1c1cc(C(F)(F)F)ccn1] | 8.49-8.61 (m, 1H), 8.45 (d, 1H), 7.21-7.28 (m, 1H), 5.86-5.94 (m, 1H), 4.88-4.93 (m, 1H), 4.78-4.86 (m, 1H), 3.86-4.08 (m, 3H), 3.29-3.42 (m, 1H). | positive ES MH+ 290 |
| A76 | 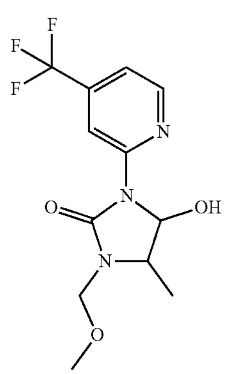 [SMILES: COCN1C(=O)N(c2cc(C(F)(F)F)ccn2)C(O)C1C] | Major diastereomer: 8.50 (s, 1H), 8.36-8.44 (m, 1H), 7.21 (d, 1H), 5.60-5.67 (m, 1H), 4.92-4.98 (m, 1H), 4.58-4.92 (m, 2H), 3.67-3.79 (m, 1H), 3.32-3.39 (m, 3H), 1.34-1.41 (m, 3H). Minor diastereomer: 8.50 (s, 1H), 8.36-8.44 (m, 1H), 7.21 (d, 1H), 5.97 (dd, 1H), 4.92-4.98 (m, 1H), 4.58-4.92 (m, 2H), 3.94-4.06 (m, 1H), 3.40-3.52 (m, 3H) 1.41-1.47 (m, 3H). | positive ES MH+ 306 |
| A77 | 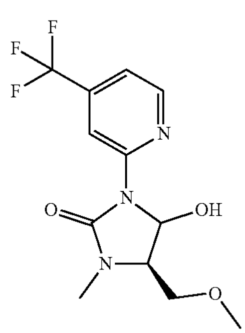 [SMILES: COC[C@@H]1C(O)N(c2cc(C(F)(F)F)ccn2)C(=O)N1C] | 8.54 (s, 1H) 8.38 (d, 1H) 7.12-7.19 (m, 1H) 5.81 (s, 1H) 4.96 (d, 1H) 3.58 (s, 3H) 3.40 (s, 3H) 2.99 (s, 3H). | positive ES MH+ 306 |

TABLE 1-continued

| Compound | STRUCTURE | 1H NMR (measured in CDCl₃ unless otherwise indicated) δ | LC-MS |
|---|---|---|---|
| A78 | 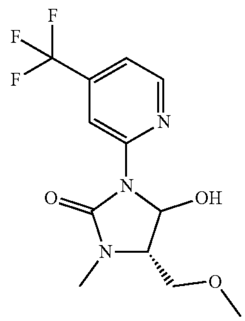 [SMILES: COC[C@H]1C(O)N(c2cc(C(F)(F)F)ccn2)C(=O)N1C] | As for A77 | As for A77 |
| A79 | 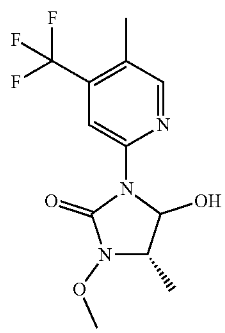 [SMILES: CON1C(=O)N(c2cc(C(F)(F)F)c(C)cn2)C(O)[C@@H]1C] | Major diastereomer: 8.48 (s, 1H), 8.25 (s, 1H), 6.80 (d, 1H), 5.61 (dd, 1H), 3.76 (s, 3H), 3.61 (dq, 1H), 2.39 (s, 3H), 1.27 (d, 3H). Minor diastereomer: 8.49 (s, 1H), 8.33 (s, 1H), 6.56 (d, 1H), 5.92 (t, 1H), 3.77 (s, 3H), 3.70 (quin, 1H), 2.39 (s, 3H), 1.30 (d, 3H). | positive ES MH+ 306 |
| A80 | 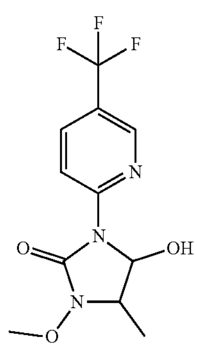 [SMILES: CON1C(=O)N(c2ccc(C(F)(F)F)cn2)C(O)C1C] | Major diastereomer: 8.53 (m, 1H), 8.39 (d, 1H), 7.93 (dd, 1H), 5.55 (d, 1H), 5.00 (br.s, 1H), 3.90 (s, 3H), 3.72 (ddd, 1H), 1.45 (d, 3H). Minor diastereomer: 8.56 (m, 1H), 8.37 (d, 1H), 7.93 (dd, 1H), 5.87 (d, 1H), 4.56 (br.s, 1H), 3.93 (s, 3H), 3.80 (pent, 1H), 1.50 (d, 3H). | positive ES MH+ 292 |
| A81 | 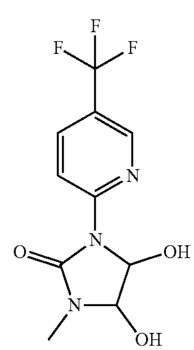 [SMILES: CN1C(=O)N(c2ccc(C(F)(F)F)cn2)C(O)C1O] | 8.49 (d, 1H), 8.28 (d, 1H), 7.89 (dd, 1H), 5.73 (d, 1H), 5.00 (d, 1H), 4.79 (d, 1H), 3.02 (s, 3H), 2.74 (d, 1H). | positive ES MH+ 278 |

TABLE 1-continued

| Compound | STRUCTURE | 1H NMR (measured in CDCl₃ unless otherwise indicated) δ | LC-MS |
|---|---|---|---|
| A82 | 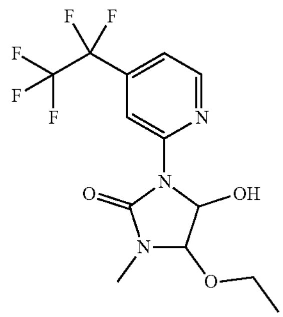 [SMILES: CCOC1C(O)N(c2cc(C(F)(F)C(F)(F)F)ccn2)C(=O)N1C] | 8.47 (s, 1H), 8.40 (d, 1H), 7.18 (d, 1H), 5.74 (s, 1H), 4.85 (brs, 1H), 4.71 (s, 1H), 3.67 (m, 2H), 3.00 (s, 3H), 1.28 (t, 3H). | positive ES MH+ 356 |
| A83 | 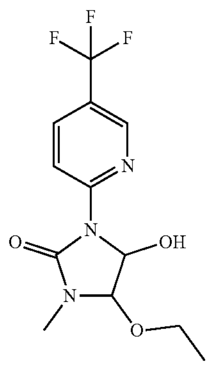 [SMILES: CCOC1C(O)N(c2ccc(C(F)(F)F)cn2)C(=O)N1C] | 8.50 (d, 1H), 8.30 (d, 1H), 7.89 (dd, 1H), 5.74 (d, 1H), 4.80 (d, 1H), 4.71 (s, 1H), 3.68 (m, 2H), 3.00 (s, 3H), 1.28 (t, 3H). | positive ES MH+ 306 |
| A84 | 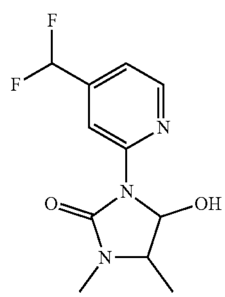 [SMILES: CC1C(O)N(c2cc(C(F)F)ccn2)C(=O)N1C] | Major diastereomer: 8.35 (s, 1H), 8.32 (d, 1H), 7.11 (d, 1H), 6.60 (t, 1H), 5.59 (d, 1H), 5.10 (br. s., 1H), 3.51 (dq, 1H), 2.92 (s, 3H), 1.33 (d, 3H).<br>Minor diastereomer: 8.34 (s, 1H), 8.32 (d, 1H), 7.11 (d, 1H), 6.60 (t, 1H), 5.93 (d, 1H), 4.96 (br. s., 1H), 3.74 (pentet, 1H), 2.88 (s, 3H), 1.39 (d, 3H). | positive ES MH+ 258 |
| A85 | 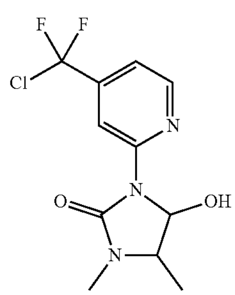 [SMILES: CC1C(O)N(c2cc(C(F)(F)Cl)ccn2)C(=O)N1C] | Major diastereomer: 8.53 (d, 1H), 8.35 (d, 1H), 7.16 (dd, 1H), 5.59 (t, 1H), 4.97 (d, 1H), 3.53 (dq, 1H), 2.93 (s, 3H), 1.34 (d, 3H).<br>Major diastereomer: 8.53 (d, 1H), 8.36 (d, 1H), 7.16 (dd, 1H), 5.94 (dd, 1H), 4.83 (d, 1H), 3.75 (t, 1H), 2.89 (s, 3H), 1.39 (d, 3H). | positive ES MH+ 292 |
| A86 | 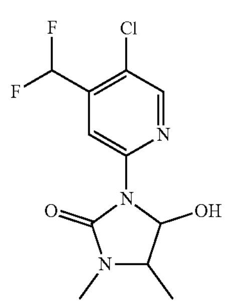 [SMILES: CC1C(O)N(c2cc(C(F)F)c(Cl)cn2)C(=O)N1C] | Major diastereomer: 8.31 (s, 1H), 7.12 (s, 1H), 6.57 (t, 1H), 5.59 (t, 1H), 4.61 (d, 1H), 3.53 (dq, 1H), 2.92 (s, 3H), 1.33 (d, 3H).<br>Major diastereomer: 8.31 (s, 1H), 7.12 (s, 1H), 6.57 (t, 1H), 5.94 (dd, 1H), 4.45 (d, 1H), 3.75 (pentet, 1H), 2.88 (s, 3H), 1.39 (d, 3H). | positive ES MH+ 292 |

TABLE 1-continued

| Compound | STRUCTURE | 1H NMR (measured in CDCl₃ unless otherwise indicated) δ | LC-MS |
|---|---|---|---|
| A87 | 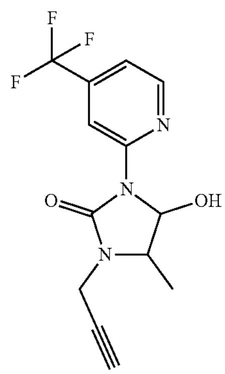 [SMILES: C#CCN1C(=O)N(c2cc(C(F)(F)F)ccn2)C(O)C1C] | Major diastereomer: 8.45-8.61 (m, 1H), 8.23-8.44 (m, 1H), 7.07-7.22 (m, 1H), 5.64-5.62 (m, 1H), 4.97-4.99 (m, 1H), 4.42 (dd, 1H), 3.92 (dd, 1H), 3.67-3.84 (m, 1H), 2.15-2.33 (m, 1H), 1.34-1.46 ppm (m, 3H). Minor diastereomer: 8.45-8.61 (m, 1H), 8.23-8.44 (m, 1H), 7.07-7.22 (m, 1H), 5.85-6.03 (m, 1H), 4.74 (d, 1H), 4.57 (dd, 1H), 4.02 (quin, 1H), 3.67-3.84 (m, 1H), 2.15-2.33 (m, 1H), 1.34-1.46 ppm (m, 3H). | positive ES MH+ 300 |
| A88 | 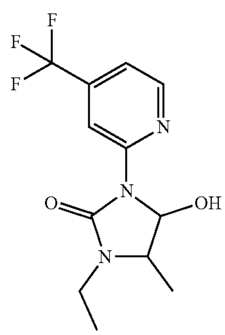 [SMILES: CCN1C(=O)N(c2cc(C(F)(F)F)ccn2)C(O)C1C] | Major diastereomer: 8.55 (s, 1H), 8.39 (d, 1H), 7.16 (d, 1H), 5.94 (d, 1H), 3.92 (m, 1H), 3.62 (m, 1H), 3.19 (m, 1H), 1.39 (d, 3H), 1.18 (t, 3H). Minor diastereomer: 8.55 (s, 1H), 8.39 (d, 1H), 7.16 (d, 1H), 5.57 (d, 1H), 3.62 (m, 2H), 3.19 (m, 1H), 1.35 (d, 3H), 1.20 (t, 3H). | positive ES MH+ 290 |
| A89 | 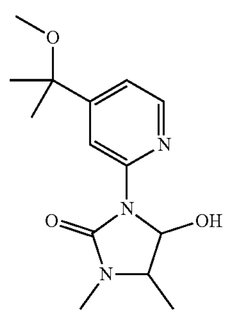 [SMILES: COC(C)(C)c1ccnc(N2C(=O)N(C)C(C)C2O)c1] | Major diastereomer: 8.19 (m, 2H), 7.09 (d, 1H), 5.59 (d, 1H), 3.50 (m, 1H), 3.13 (s, 3H), 2.92 (s, 3H), 1.52 (s, 6H), 1.33 (d, 3H). Minor diastereomer: 8.19 (m, 2H), 7.09 (d, 1H, 5.93 (d, 1H), 3.73 (m, 1H), 3.13 (s, 3H), 2.88 (s, 3H), 1.52 (s, 6H), 1.40 (d, 3H). | positive ES MH+ 280 |
| A90 | 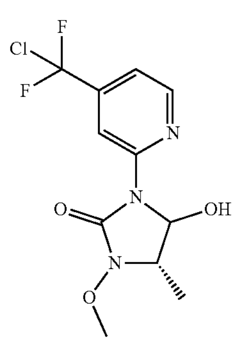 [SMILES: CON1C(=O)N(c2cc(C(F)(F)Cl)ccn2)C(O)[C@@H]1C] | Major diastereomer: 8.54 (m, 1H), 8.39 (d, 1H), 7.26 (dd, 1H), 5.53 (dd, 1H), 5.03 (d, 1H), 3.90 (s, 3H), 3.71 (ddd, 1H), 1.45 (d, 3H). Minor diastereomer: 8.52 (m, 1H), 8.42 (d, 1H), 7.24 (dd, 1H), 5.85 (dd, 1H), 4.59 (d, 1H), 3.93 (s, 3H), 3.79 (pentet, 1H), 1.49 (d, 3H). | positive ES MH+ 308 |

TABLE 1-continued

| Compound | STRUCTURE | 1H NMR (measured in CDCl₃ unless otherwise indicated) δ | LC-MS |
|---|---|---|---|
| A91 | 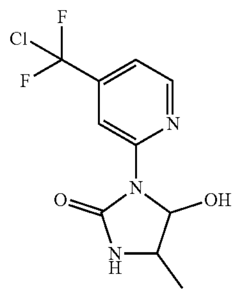 [SMILES: CC1NC(=O)N(c2cc(C(F)(F)Cl)ccn2)C1O] | Major diastereomer: 8.50 (s, 1H), 8.38 (d, 1H), 7.19 (dd, 1H), 5.86 (br s, 1H), 5.68 (m, 1H), 4.98 (d, 1H), 3.74 (m, 1H), 1.36 (d, 3H). Minor diastereomer: 8.46 (s, 1H), 8.36 (d, 1H), 7.12 (dd, 1H), 5.99 (d, 1H), 5.71 (br s, 1H), 4.88 (d, 1H), 4.04 (pentet, 1H), 1.39 (d, 3H). | positive ES MH+ 278 |
| A92 | 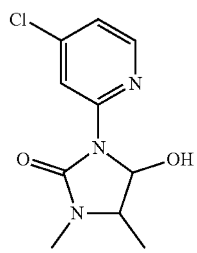 [SMILES: CC1C(O)N(c2cc(Cl)ccn2)C(=O)N1C] | Major diastereomer: 8.28 (d, 1H), 8.10 (d, 1H), 6.96 (dd, 1H), 5.55 (t, 1H), 5.07 (d, 1H), 3.49 (ddd, 1H), 2.91 (s, 3H), 1.32 (d, 3H). Minor diastereomer: 8.27 (d, 1H), 8.11 (d, 1H), 6.96 (dd, 1H), 5.89 (dd, 1H), 4.94 (d, 1H), 3.72 (m, 1H), 2.87 (s, 3H), 1.37 (d, 3H). | positive ES MH+ 242 |
| A93 | 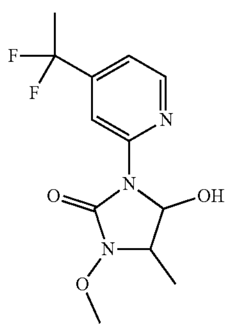 [SMILES: CON1C(=O)N(c2cc(C(C)(F)F)ccn2)C(O)C1C] | Major diastereomer 8.36 (m, 2H), 7.18 (m, 1H), 5.52 (d, 1H), 4.47 (brs, 1H), 3.90 (s, 3H), 3.70 (m, 1H), 1.92 (t, 3H), 1.48 (d, 3H). Minor diastereomer 8.36 (m, 2H), 7.18 (m, 1H), 5.83 (d, 1H), 5.21 (brs, 1H), 3.93 (s, 3H), 3.77 (m, 1H), 1.92 (t, 3H), 1.49 (d, 3H). | positive ES MH+ 288 |
| A94 | 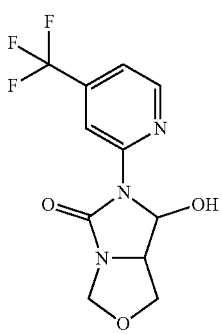 [SMILES: O=C1N2COCC2C(O)N1c1cc(C(F)(F)F)ccn1] | Major diastereomer 8.59 (s, 1H), 8.45 (d, 1H), 7.28 (dd, 1H), 5.97 (d, 1H), 5.39 (d, 1H), 5.03 (brs, 1H), 4.42 (m, 1H), 4.12 (m, 1H), 4.00 (m, 1H), 3.63 (m, 1H). Minor diastereomer 8.59 (s, 1H), 8.45 (d, 1H), 7.28 (dd, 1H), 6.17 (d, 1H), 5.39 (d, 1H), 5.24 (brs, 1H), 4.41 (m, 1H), 4.39 (m, 1H), 4.26 (m, 1H), 3.88 (m, 1H). | positive ES MH+ 290 |
| A95 | 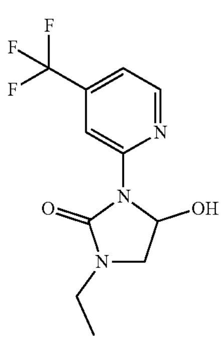 [SMILES: CCN1CC(O)N(c2cc(C(F)(F)F)ccn2)C1=O] | 8.55 (s, 1H), 8.39 (d, 1H), 7.17 (d, 1H), 6.07 (d, 1H), 5.0 (br.s, 1H), 3.72 (m, 1H), 3.42 (m, 3H), 1.22 (t, 3H). | positive ES MH+ 276 |

TABLE 1-continued

| Compound | STRUCTURE | 1H NMR (measured in CDCl₃ unless otherwise indicated) δ | LC-MS |
| --- | --- | --- | --- |
| A96 | 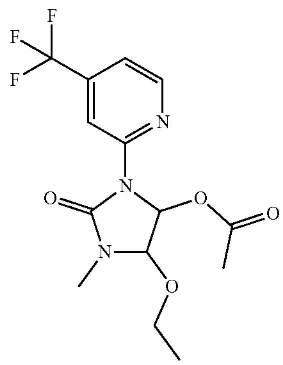 [SMILES: CCOC1C(OC(C)=O)N(c2cc(C(F)(F)F)ccn2)C(=O)N1C] | 8.57 (s, 1H), 8.40 (d, 1H), 7.17 (d, 1H), 6.90 (s, 1H), 4.62 (s, 1H), 3.87 (m, 1H), 3.64 (m, 1H), 2.99 (s, 3H), 2.07 (s, 3H), 1.27 (t, 3H). | positive ES MH+ 348 |
| A97 | 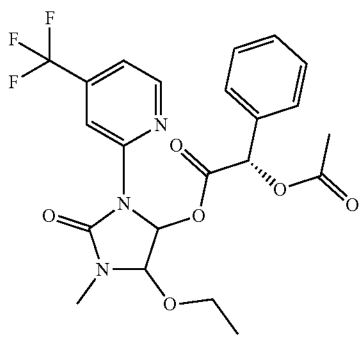 [SMILES: CCOC1C(OC(=O)[C@@H](OC(C)=O)c2ccccc2)N(c2cc(C(F)(F)F)ccn2)C(=O)N1C] | | positive ES MH+ 482 |
| A98 | 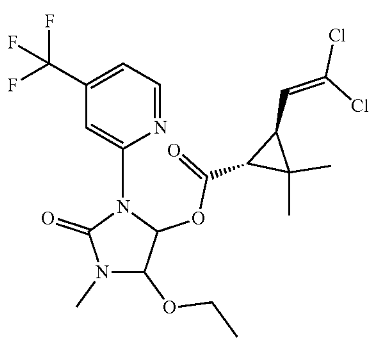 [SMILES: CCOC1C(OC(=O)[C@@H]2[C@@H](C=C(Cl)Cl)C2(C)C)N(c2cc(C(F)(F)F)ccn2)C(=O)N1C] | | positive ES MH+ 496/498 |
| A99 | 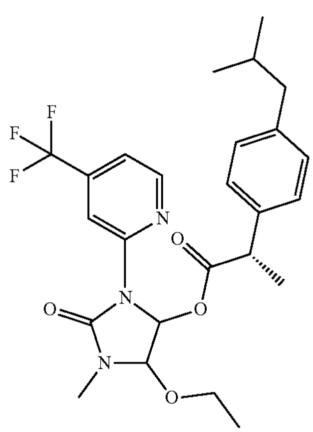 [SMILES: CCOC1C(OC(=O)[C@@H](C)c2ccc(CC(C)C)cc2)N(c2cc(C(F)(F)F)ccn2)C(=O)N1C] | | positive ES MH+ 494 |

TABLE 1-continued

| Compound | STRUCTURE | 1H NMR (measured in CDCl₃ unless otherwise indicated) δ | LC-MS |
|---|---|---|---|
| A100 | 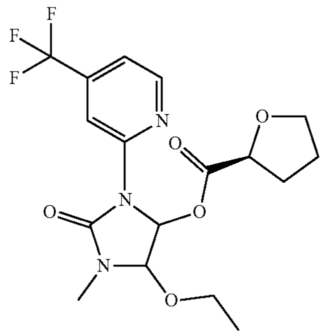 [SMILES: CCOC1C(OC(=O)[C@@H]2CCCO2)N(c2cc(C(F)(F)F)ccn2)C(=O)N1C] | | positive ES MH+ 404 |
| A101 | 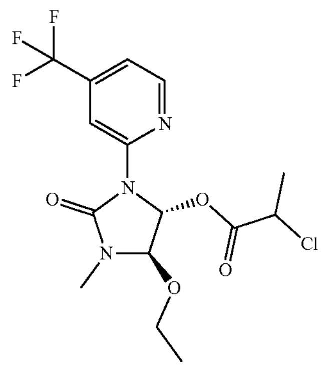 [SMILES: CCO[C@@H]1[C@@H](OC(=O)C(C)Cl)N(c2cc(C(F)(F)F)ccn2)C(=O)N1C] | | positive ES MH+ 396 |
| A102 | 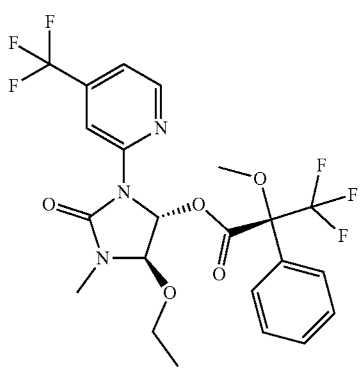 [SMILES: CCO[C@@H]1[C@@H](OC(=O)[C@](OC)(c2ccccc2)C(F)(F)F)N(c2cc(C(F)(F)F)ccn2)C(=O)N1C] | 8.49 (s, 1H), 8.27 (d, 1H), 7.55 (d, 2H), 7.33-7.41 (m, 3H), 7.14 (dd, 1H), 7.10 (s, 1H), 4.70 (s, 1H), 3.92 (dq, 1H), 3.68 (dq, 1H), 3.39 (s, 3H), 3.00 (s, 3H), 1.30 (t, 3H). | positive ES MH+ 522 |
| A103 | 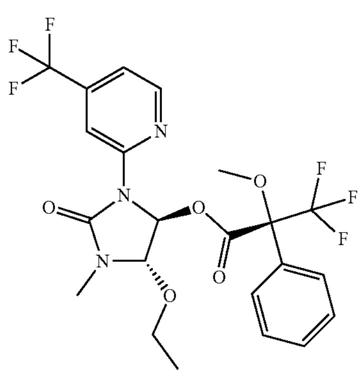 [SMILES: CCO[C@H]1[C@H](OC(=O)[C@](OC)(c2ccccc2)C(F)(F)F)N(c2cc(C(F)(F)F)ccn2)C(=O)N1C] | 8.55 (s, 1H), 8.42 (d, 1H), 7.53 (d, 2H), 7.31-7.41 (m, 3H), 7.21 (dd, 1H), 7.11 (s, 1H), 4.51 (s, 1H), 3.91 (dq, 1H), 3.66 (dq, 1H), 3.46 (s, 3H), 2.92 (s, 3H), 1.30 (t, 3H). | positive ES MH+ 522 |

TABLE 1-continued

| Compound | STRUCTURE | 1H NMR (measured in CDCl₃ unless otherwise indicated) δ | LC-MS |
|---|---|---|---|
| A104 | 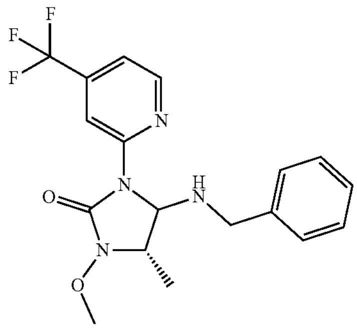 [SMILES: CON1C(=O)N(c2cc(C(F)(F)F)ccn2)C(NCc2ccccc2)[C@@H]1C] | Major diastereomer: 8.50 (s, 1H), 8.40 (d, 1H), 7.28-7.13 (m, 6H), 5.13 (d, 1H), 3.89 (s, 3H), 3.77-3.71 (m, 2H), 3.53 (d, 1H), 3.16 (br. s., 1H), 1.45 (d, 3H) Minor diastereomer: 8.57 (s, 1H), 8.40 (d, 1H), 7.28-7.13 (m, 6H), 5.52 (d, 1H), 3.94 (s, 3H), 3.90-3.73 (m, 2H), 3.57 (d, 1H), 3.30 (very br. s., 1H), 1.53 (d, 3H). | positive ES MH+ 381 |
| A105 | 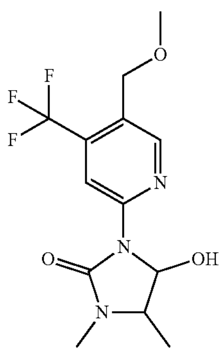 [SMILES: COCc1cnc(N2C(=O)N(C)C(C)C2O)cc1C(F)(F)F] | Major diastereomer: 8.53 (s, 1H), 8.46 (s, 1H), 5.59 (t, 1H), 4.97 (t, 1H), 4.57 (s, 2H), 3.52 (m, 1H), 3.45 (s, 3H), 2.92 (d, 3H), 1.33 (dd, 3H). Minor diastereomer: 8.53 (s, 1H), 8.47 (s, 1H), 5.94 (dd, 1H), 4.82 (t, 1H), 4.57 (s, 2H), 3.75 (m, 1H), 3.45 (s, 3H), 2.88 (d, 3H), 1.39 (dd, 3H). | positive ES MH+ 320 |
| A106 | 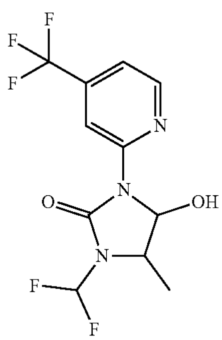 [SMILES: CC1C(O)N(c2cc(C(F)(F)F)ccn2)C(=O)N1C(F)F] | Major diastereomer: 8.30-8.56 (m, 2H), 7.27-7.32 (m, 1H), 6.80-7.23 (m, 1H), 5.59-5.75 (m, 1H), 4.80-4.97 (m, 1H), 3.83-4.10 (m, 1H), 1.40-1.53 (m, 3H). Minor diastereomer: 8.30-8.56 (m, 2H), 7.27-7.32 (m, 1H), 6.80-7.23 (m, 1H), 5.87-6.09 (m, 1H), 4.69-4.80 (m, 1H), 4.10-4.35 (m, 1H), 1.53-1.60 (m, 3H). | positive ES MH+ 312 |
| A107 | 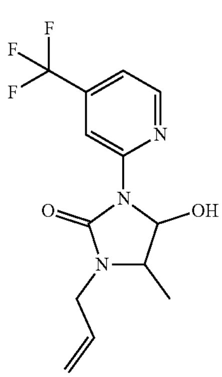 [SMILES: C=CCN1C(=O)N(c2cc(C(F)(F)F)ccn2)C(O)C1C] | Major diastereomer: 8.53 (s, 1H), 8.29-8.44 (m, 1H), 7.07-7.23 (m, 1H), 5.73-5.89 (m, 1H), 5.62 (t, 1H), 5.17-5.36 (m, 2H), 4.92 (d, 1H), 4.15-4.33 (m, 1H), 3.51-3.77 (m, 2H), 1.24-1.34 (m, 3H). Minor diastereomer: 8.53 (s, 1H), 8.29-8.44 (m, 1H), 7.07-7.23 (m, 1H), 5.94 (dd, 1H), 5.73-5.89 (m, 1H), 5.17-5.36 (m, 2H), 4.80 (d, 1H), 4.15-4.33 (m, 1H), 3.89 (quin, 1H), 3.51-3.77 (m, 1H), 1.36 (d, 3H). | positive ES MH+ 302 |

TABLE 1-continued

| Compound | STRUCTURE | 1H NMR (measured in CDCl₃ unless otherwise indicated) δ | LC-MS |
|---|---|---|---|
| A108 | 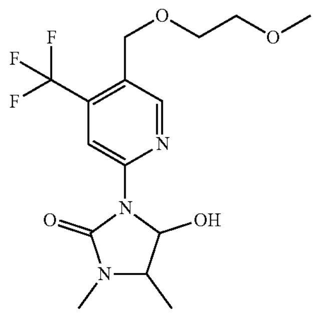 [SMILES: COCCOCc1cnc(N2C(=O)N(C)C(C)C2O)cc1C(F)(F)F] | Major diastereomer: 8.52 (s, 1H), 8.51 (s, 1H), 5.58 (t, 1H), 4.96 (br t, 1H), 4.69 (s, 2H), 3.69 (m, 2H), 3.60 (m, 2H), 3.52 (dq, 1H), 3.40 (d, 3H), 2.92 (d, 3H), 1.33 (dd, 3H).<br>Minor diastereomer: 8.52 (s, 1H), 8.51 (s, 1H), 5.93 (dd, 1H), 4.81 (dd, 1H), 4.69 (s, 2H), 3.75 (m, 1H), 3.69 (m, 2H), 3.60 (m, 2H), 3.40 (d, 3H), 2.88 (d, 3H), 1.38 (dd, 3H). | positive ES MH+ 364 |
| A109 | 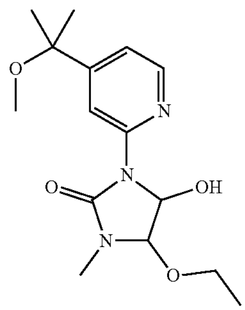 [SMILES: CCOC1C(O)N(c2cc(C(C)(C)OC)ccn2)C(=O)N1C] | 8.27 (d, 1H), 8.13 (s, 1H), 7.04 (d, 1H), 5.75 (s, 1H), 4.62 (s, 1H), 3.58 (m, 2H), 3.02 (s, 3H), 2.85 (s, 3H), 1.42 (s, 6H), 1.15 (t, 3H). | positive ES MH+ 310 |
| A110 | 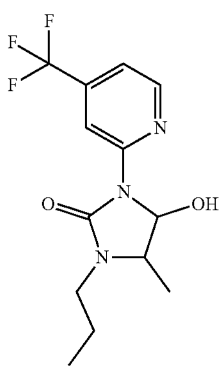 [SMILES: CCCN1C(=O)N(c2cc(C(F)(F)F)ccn2)C(O)C1C] | Major diastereomer: 8.53 (s, 1H), 8.35-8.38 (m, 1H), 7.12-7.18 (m, 1H), 5.59-5.65 (m, 1H), 4.96 (br. s., 1H), 3.54-3.63 (m, 2H), 3.02-3.17 (m, 1H), 1.45-1.77 (m, 2H), 1.32 (d, 2H), 0.90-1.02 (m, 3H).<br>Minor diastereomer: 8.53 (s, 1H), 8.35-8.38 (m, 1H), 7.12-7.18 (m, 1H), 5.94 (d, 1H), 4.84 (br. s., 1H), 3.85-3.95 (m, 1H), 3.02-3.17 (m, 1H), 1.45-1.77 (m, 2H), 1.38 (d, 1H), 0.90-1.02 (m, 3H). | positive ES MH+ 304 |
| A111 | 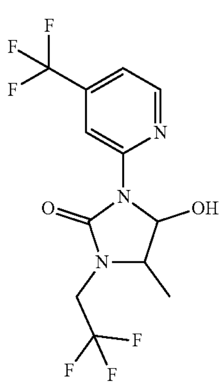 [SMILES: CC1C(O)N(c2cc(C(F)(F)F)ccn2)C(=O)N1CC(F)(F)F] | Major diastereomer: 8.50 (s, 1H), 8.42 (d, 1H), 7.17-7.25 (m, 1H), 5.66-5.71 (m, 1H), 4.92 (br. s., 1H), 4.16-4.38 (m, 1H), 3.79 (qd, 1H), 3.53-3.74 (m, 1H), 1.38 (d, 3H).<br>Minor diasteromer: 8.48 (s, 1H), 8.42 (d, 1H), 7.17-7.25 (m, 1H), 6.00 (d, 1H), 4.80 (br. s., 1H), 4.16-4.38 (m, 1H), 3.99-4.08 (m, 1H), 3.53-3.74 (m, 1H), 1.41-1.47 (m, 3H). | positive ES MH+ 344 |

TABLE 1-continued

| Compound | STRUCTURE | 1H NMR (measured in CDCl₃ unless otherwise indicated) δ | LC-MS |
|---|---|---|---|
| A112 | 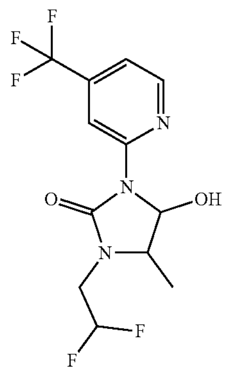 [SMILES: CC1C(O)N(c2cc(C(F)(F)F)ccn2)C(=O)N1CC(F)F] | Major diastereomer: 8.47 (s, 1H), 8.36-8.43 (m, 1H), 7.20 (d, 1H), 5.79-6.15 (m, 1H), 5.61-5.69 (m, 1H), 4.92 (br. s., 1H), 3.95-4.07 (m, 1H), 3.67-3.78 (m, 1H), 3.38-3.56 (m, 1H), 1.36 (d, 3H).<br>Minor diastereomer: 8.47 (s, 1H), 8.36-8.43 (m, 1H), 7.20 (d, 1H), 5.79-6.15 (m, 2H), 4.69-4.82 (m, 1H), 3.95-4.07 (m, 1H), 3.78-3.94 (m, 1H), 3.38-3.56 (m, 1H), 1.39-1.44 (m, 3H). | positive ES MH+ 326 |
| A113 | 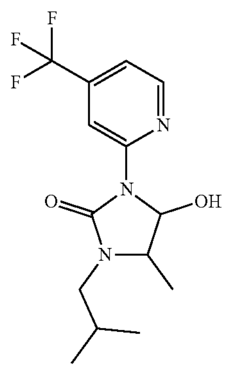 [SMILES: CC(C)CN1C(=O)N(c2cc(C(F)(F)F)ccn2)C(O)C1C] | Major diastereomer: 8.44-8.59 (m, 1H), 8.31-8.42 (m, 1H), 7.16 (d, 1H), 5.94 (d, 1H), 4.83 (br. s., 1H), 3.83-3.96 (m, 1H), 3.17-3.33 (m, 1H), 3.02 (dd, 1H), 1.83-2.13 (m, 1H), 1.38 (d, 3H), 0.87-1.05 (m, 6H) -<br>Minor diastereomer: 8.44-8.59 (m, 1H), 8.31-8.42 (m, 1H), 7.16 (d, 1H), 5.61 (s, 1H), 4.87-5.00 (m, 1H), 3.52-3.69 (m, 1H), 3.33-3.47 (m, 1H), 2.90 (dd, 1H), 1.83-2.13 (m, 1H), 1.31 (d, 3H), 0.87-1.05 (m, 6H). | positive ES MH+ 318 |
| A114 | 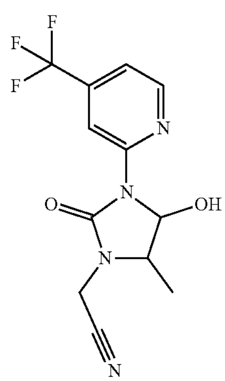 [SMILES: CC1C(O)N(c2cc(C(F)(F)F)ccn2)C(=O)N1CC#N] | Major diastereomer: 8.36-8.49 (m, 2H), 7.25 (d, 1H), 5.69 (d, 1H), 4.32-4.47 (m, 1H), 4.16-4.28 (m, 1H), 3.66-3.84 (m, 1H), 1.40-1.50 (m, 3H).<br>Minor diastereomer: 8.36-8.49 (m, 2H), 7.25 (d, 1H), 6.02 (d, 1H), 4.56-4.70 (m, 1H), 3.89-4.03 (m, 1H), 3.66-3.84 (m, 1H), 1.40-1.50 (m, 3H). | positive ES MH+ 301 |
| A115 | 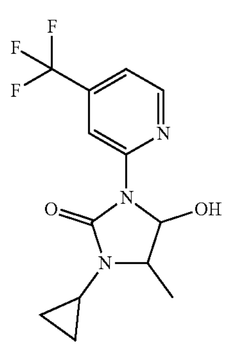 [SMILES: CC1C(O)N(c2cc(C(F)(F)F)ccn2)C(=O)N1C1CC1] | Major diastereomer: 8.48-8.60 (m, 1H), 8.29-8.44 (m, 1H), 7.06-7.21 (m, 1H), 5.51-5.65 (m, 1H), 4.82 (br. s., 1H), 3.48-3.57 (m, 1H), 2.48-2.58 (m, 1H), 1.33-1.41 (m, 3H), 0.59-1.06 (m, 4H).<br>Minor diastereomer 8.48-8.60 (m, 1H), 8.29-8.44 (m, 1H), 7.06-7.21 (m, 1H), 5.89 (d, 1H), 4.88-4.99 (m, 1H), 3.76-3.88 (m, 1H), 2.36-2.47 (m, 1H), 1.42-1.50 (m, 3H), 0.59-1.06 (m, 4H). | positive ES MH+ 302 |

TABLE 1-continued

| Compound | STRUCTURE | 1H NMR (measured in CDCl₃ unless otherwise indicated) δ | LC-MS |
|---|---|---|---|
| A116 | 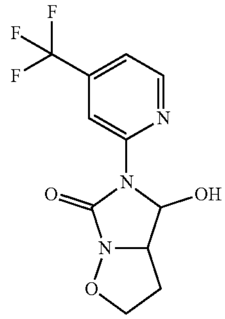 [SMILES: O=C1N2OCCC2C(O)N1c1cc(C(F)(F)F)ccn1] | Major diastereomer 8.59 (s, 1H), 8.49 (d, 1H), 7.32 (d, 1H), 6.05 (s, 1H), 4.84 (brs, 1H), 4.18 (m, 1H), 3.98 (m, 1H), 3.91 (m, 1H), 2.68 (m, 1H), 2.13 (m, 1H). Minor diastereomer 8.59 (s, 1H), 8.46 (d, 1H), 7.32 (d, 1H), 6.15 (d, 1H), 5.39 (brs, 1H), 4.23 (m, 1H), 3.98 (m, 1H), 3.91 (m, 1H), 2.80 (m, 1H), 2.35 (m, 1H). | positive ES MH+ 290 |

Example 19: Preparation of 1,1,3-trimethoxy-N-methyl-propan-2-amine as Used for Synthesis of Examples of the Type A54, A77 and A78 (Chiral Preparative HPLC of Racemic Product A54 Gave Separated Enantiomers A77 and A78)

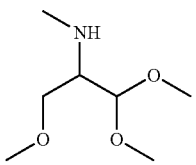

Procedure for Synthesis of 1,1,3-trimethoxy-N-methyl-propan-2-amine (Step 1)

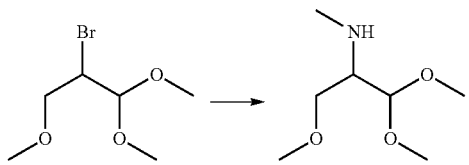

A solution of 2-bromo-1,1,3-trimethoxy-propane (commercially available) (7 g, 32.85 mmol) in methylamine (40% aqueous solution) (105 mL, 210 mmol) was divided into seven equal portions and these were heated at 130° C. for 1 h in a microwave. The combined reaction mixtures were then concentrated and the residue obtained was treated with toluene and evaporated again. The residue was then stirred with DCM, filtered and evaporated to give the crude product that was taken to next step without further purification.

Example 20: Preparation of 2-chloro-4-(1-fluoro-1-methyl-ethyl)pyridine as Used for Synthesis of Examples of the Type A63

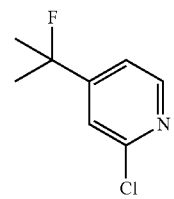

Procedure for Synthesis of 2-chloro-4-(1-fluoro-1-methyl-ethyl)pyridine (Step 1)

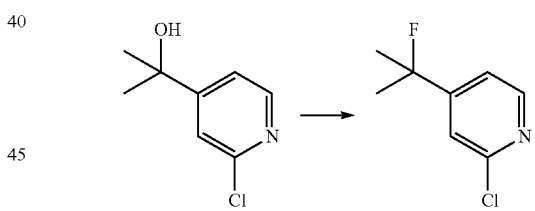

2-(2-chloro-4-pyridyl)propan-2-ol (commercially available) (180 mg, 1.0 mmol) was dissolved in DCM and the resultant mixture was cooled to 0° C. Diethylaminosulfur trifluoride (2.5 equiv., 5.2 mmol) was added dropwise such that the temperature did not exceed 5° C. After the addition the reaction was allowed to warm to room temperature and was then added portionwise with stirring to a mixture of ice (100 ml) and NaHCO₃ in a beaker (some effervescence), making sure that the pH of the solution was >7 at all times. After ~30 mins, the mixture was diluted with DCM (30 mL) and water (20 mL) and transferred to a sep funnel. The organic phase was separated. The aqueous phase was further extracted with DCM (2×20 mL), the organic extracts were then combined, washed with water (15 mL), dried over MgSO₄, filtered and the filtrate evaporated giving a yellow-brown liquid. This was chromatographed on silica. Fractions containing product were evaporated to give the desired product, which was used without further purification.

LC-MS: (positive ES MH+ 174).

Example 21: Preparation of 4-(1,1,2,2,2-pentafluoroethyl)pyridin-2-amine as Used for Synthesis of Examples of the Type A72, A73

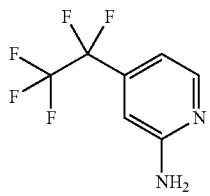 [SMILES: Nc1cc(C(F)(F)C(F)(F)F)ccn1]

Procedure for Synthesis of 4-(1,1,2,2,2-pentafluoroethyl)pyridin-2-amine (Step 1)

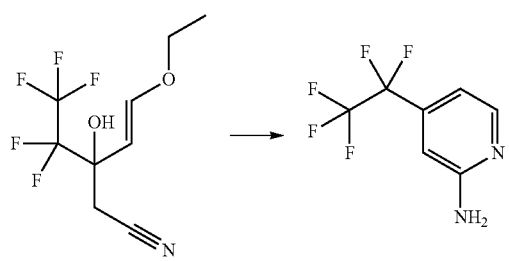 [SMILES: CCO/C=C/C(O)(CC#N)C(F)(F)C(F)(F)F ; Nc1cc(C(F)(F)C(F)(F)F)ccn1]

Prepared by analogy to the synthesis of 4-(trifluoromethyl)pyridin-2-amine (as described in EP2228366) using (E)-5-ethoxy-3-hydroxy-3-(1,1,2,2,2-pentafluoroethyl)pent-4-enenitrile (for a synthesis see Martins et al, *ARKIVOC* Issue 13, pages 187-194) as starting material. This synthesis can be applied to the synthesis of a range of related pyridine intermediates.

Example 22: Preparation of 2-chloro-4-[chloro(difluoro)methyl]pyridine as Used for Synthesis of Examples of the Type A90, A91

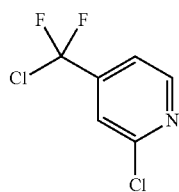 [SMILES: FC(F)(Cl)c1ccnc(Cl)c1]

Procedure for Synthesis of 2-chloro-4-[chloro(difluoro)methyl]pyridine (Step 1)

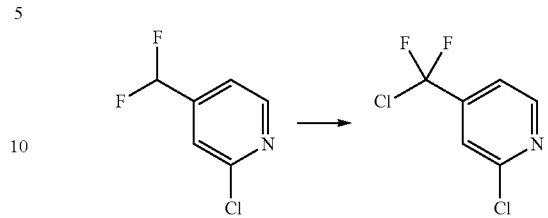

2-chloro-4-(difluoromethyl)pyridine (commercially available) (0.950 g, 5.81 mmol) was suspended in CCl$_4$ (3.3 ml), then 1,3,5-trichloro-1,3,5-triazinane-2,4,6-trione (675 mg, 0.5 equiv.) and benzoyl benzenecarboperoxoate (70 mg, 0.05 equiv.) were added and the mixture was microwaved to 160° C. for 30 mins. Further benzoyl benzenecarboperoxoate (70 mg, 0.05 equiv.) was added and the mixture was further microwaved to 180° C. for 20 mins. Even further benzoyl benzenecarboperoxoate (70 mg, 0.05 equiv.) was added and the mixture was further microwaved at 180° C. for 20 mins. The mixture wa filtered through celite, washed through with DCM then chromatographed eluting with 0-7% ethyl acetate in isohexane. Fractions contained product were combined and evaporated to give product as a colourless oil (700 mg, 61% yield).

$^1$H NMR: 8.58 (dd, 1H), 7.57 (d, 1H), 7.45 (dd, 1H).

Example 23: Preparation of 2-chloro-4-(1-methoxy-1-methyl-ethyl)pyridine as Used for Synthesis of Examples of the Type A89

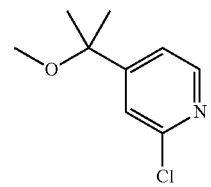

Procedure for Synthesis of 2-chloro-4-[chloro(difluoro)methyl]pyridine (Step 1)

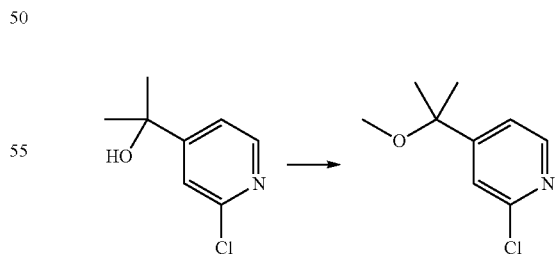

A mixture of 2-(2-chloro-4-pyridyl)propan-2-ol (commercially available) (2.4 g, 14 mmol) in THF (120 mL) and methyl iodide (1.8 mL, 28 mmol) was treated with sodium hydride (0.71 g, 28 mmol). The mixture was stirred for 16 h at rt. and then the reaction mix was poured into water (500 mL), and extracted with ethyl acetate. The combined organic layers were dried over sodium sulfate and chromatographed.

Fractions contained product were combined and evaporated to give product as a colourless oil (2.31 g, 89% yield).
LC-MS: (positive ES MH+ 186).

Example 24: Preparation of N-[6-chloro-4-(trifluoromethyl)-3-pyridyl]-2,2-dimethyl-propanamideas Used for Synthesis of Examples of the Type A57

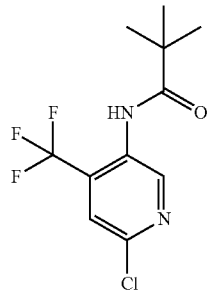

Procedure for Synthesis of N-[6-chloro-4-(trifluoromethyl)-3-pyridyl]-2,2-dimethyl-propanamide (Step 1)

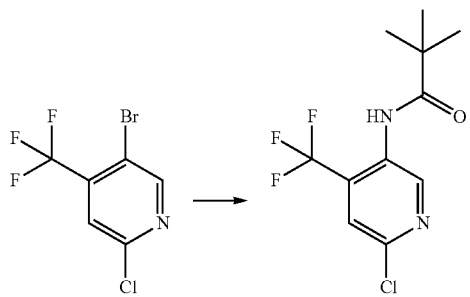 [SMILES: FC(F)(F)c1cc(Cl)ncc1Br ; CC(C)(C)C(=O)Nc1cnc(Cl)cc1C(F)(F)F]

A mixture of 5-bromo-2-chloro-4-(trifluoromethyl)pyridine (commercially available) (75 mg, 0.288 mmol), 2,2-dimethylpropanamide (32 mg, 0.317 mmol), XantPhos Pd G3 precatalyst (13 mg, 0.014 mmol), K$_2$CO$_3$ (79 mg, 0.57 mmol) in 1,4-Dioxane (0.5 mL) was heated at 90° C. for 0.5 h and then 110° C. for 2 h. Purification by reverse phase HPLC delivered product (14 mg, 15%).
LC-MS: (positive ES MH+ 281).

Example 25: Preparation of N-tert-butyl-6-chloro-4-(trifluoromethyl)pyridine-3-carboxamide as Used for Synthesis of Examples of the Type A65

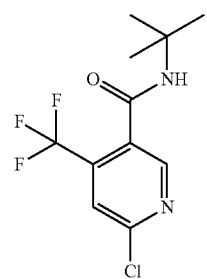 [SMILES: CC(C)(C)NC(=O)c1cnc(Cl)cc1C(F)(F)F]

Procedure for Synthesis of N-tert-butyl-6-chloro-4-(trifluoromethyl)pyridine-3-carboxamide (Step 1)

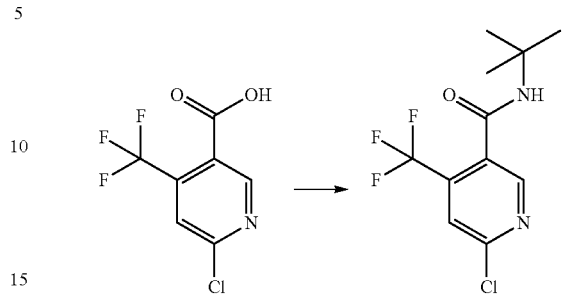

To a stirred solution of 6-chloro-4-(trifluoromethyl)pyridine-3-carboxylic acid (for a synthesis see Tetrahedron, 2004, 60(51), pages 11869-11874) (3.87 g, 17.2 mmol) in DCM (8 mL) was added tert-butylamine (3.61 mL, 34.3 mmol) followed by DIPEA (3.59 mL, 20.6 mmol). The reaction mixture was cooled to 0° C. before the addition of HATU (4.84 g, 20.6 mmol). The reaction was stirred for 10 mins at 0° C., followed by stirring for 30 mins at room temperature. The reaction was then quenched with water. The aqueous layer was extracted with DCM, and the combined organic phases, dried (MgSO$_4$) and evaporated. Crude product was chromatographed eluting with 3:1, iso-hexane/EtOAc, followed by recrystallisation (Et$_2$O/i-hexane) provided product (3.44 g, 12.3 mmol, 71% yield).
LC-MS: (positive ES MH+ 281).

Example 26: Preparation of 2-chloro-5-(methoxymethyl)-4-(trifluoromethyl)pyridine as Used for Synthesis of Examples of the Type A105

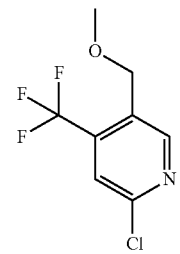

Procedure for Synthesis of [6-chloro-4-(trifluoromethyl)-3-pyridyl]methanol (Step 1)

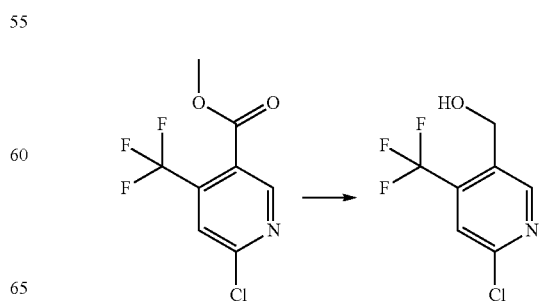

Methyl 6-chloro-4-(trifluoromethyl)pyridine-3-carboxylate (commercially available) (1.00 g) was dissolved in dry THF (12 mL) under a $N_2$ atmosphere and the reaction was cooled to −60° C. then LiAlH4 (163 mg) was added over 10 mins. The reaction was stirred at −60° C. for 25 mins and was then treated with saturated $NH_4Cl$ (aq) (5 mL) and then EtOAc (60 mL). Filtration through celite and then evaporation gave a crude oil which was dissolved in MeOH (5 mL), cooled to 0° C. then $NaBH_4$ (53 mg) was added portionwise and the reaction was stirred at 0° C. The reaction was then concentrated, treated with EtOAc (10 mL) and washed with 10% citric acid and then saturated brine and finally the organic layer was dried $Na_2SO_4$ and evaporated to give the desired product.

$^1$H NMR: (400 MHz, Chloroform) δ 8.78 (s, 1H), 7.56 (s, 1H), 4.93 (s, 2H), 1.91 (very br s, 1H).

Procedure for Synthesis of 2-chloro-5-(methoxymethyl)-4-(trifluoromethyl)pyridine (Step 2)

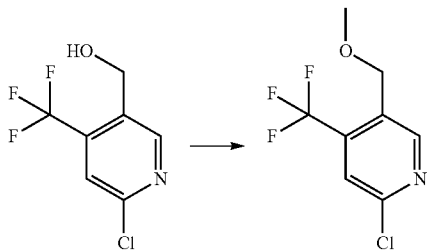

[6-chloro-4-(trifluoromethyl)-3-pyridyl]methanol (655 mg) was dissolved in dry THF (2 mL), cooled to 5° C. under $N_2$ then KOtBu (1.65M in THF) (2.07 mL) was added over 1 min. Then MeI (236 μL) was added. The reaction was stirred for 3 minutes, then EtOAc (10 mL) and saturated brine (aqueous), was added and the aqueous layer was extracted with further EtOAc (2×20 mL). The combined organic layers were dried ($Na_2SO_4$), filtered and evaporated to give amber oil, which was chromatographed, eluting with 0-30% EtOAc in isohexane. Fractions containing product were evaporated to give product as an amber oil (332 mg, 48%).

$^1$H NMR: (400 MHz, Chloroform) δ 8.70 (s, 1H), 7.56 (s, 1H), 4.63 (s, 2H), 3.48 (s, 3H).

LC-MS: (positive ES MH+ 226).

Example 27—Herbicidal Action

Example 27a: Pre-Emergence Herbicidal Activity

Seeds of a variety of test species were sown in standard soil in pots. After cultivation for one day (pre-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 2.

TABLE 2

| Application pre-emergence | | | | | | | |
|---|---|---|---|---|---|---|---|
| Compound number | Rate (g/Ha) | AMARE | ABUTH | ECHCG | SETFA | ALOMY | ZEAMX |
| A1 | 1000 | 5 | 5 | 5 | 5 | 4 | 3 |
| A2 | 1000 | 5 | 5 | 4 | 3 | 2 | 1 |
| A3 | 1000 | 5 | 4 | 5 | 5 | 3 | 3 |
| A4 | 1000 | 5 | 5 | 5 | 5 | 4 | 3 |
| A5 | 1000 | 5 | 5 | 4 | 4 | 3 | 2 |
| A6 | 1000 | 5 | 5 | 4 | 5 | 4 | 2 |
| A7 | 1000 | 5 | 5 | 3 | 4 | 4 | 1 |
| A8 | 1000 | 5 | 5 | 4 | 5 | 4 | 3 |
| A9 | 1000 | 5 | 5 | 5 | 5 | 4 | 3 |
| A10 | 1000 | 5 | 5 | 5 | 5 | 4 | 3 |
| A11 | 1000 | 5 | 5 | 4 | 5 | 4 | 3 |
| A12 | 1000 | 5 | 5 | 5 | 5 | 4 | 3 |
| A13 | 1000 | 5 | 5 | 3 | 3 | 3 | 1 |
| A14 | 1000 | 5 | | 5 | 5 | 4 | |
| A15 | 1000 | 5 | | 3 | 4 | 3 | |
| A16 | 1000 | 5 | | 5 | 4 | 4 | |
| A17 | 1000 | 5 | | 4 | 3 | 3 | |
| A18 | 1000 | 5 | | 5 | 4 | 4 | |
| A19 | 1000 | 5 | 5 | 5 | 5 | 4 | 3 |
| A20 | 1000 | 5 | 5 | 4 | 5 | 4 | 5 |
| A21 | 1000 | 5 | 5 | 5 | 5 | 3 | 2 |
| A22 | 1000 | 5 | 5 | 5 | 5 | 4 | 3 |
| A23 | 1000 | 5 | 2 | 2 | 3 | 3 | 1 |
| A24 | 1000 | 5 | 5 | 5 | 4 | 4 | 3 |
| A25 | 1000 | 5 | 5 | 5 | 4 | 4 | 2 |
| A26 | 1000 | 3 | 4 | 4 | 4 | 2 | 2 |
| A27 | 1000 | 5 | 4 | 4 | 4 | 3 | 3 |
| A28 | 1000 | 5 | 3 | 4 | 5 | 4 | 2 |
| A29 | 1000 | 5 | 5 | 1 | 2 | 1 | 1 |
| A30 | 1000 | 5 | 5 | 5 | 5 | 4 | 2 |
| A31 | 1000 | 5 | 5 | 5 | 5 | | 2 |
| A32 | 1000 | 5 | 5 | 5 | 4 | 4 | 2 |
| A33 | 1000 | 5 | 4 | 2 | 3 | 3 | 0 |

TABLE 2-continued

| Application pre-emergence | | | | | | | |
|---|---|---|---|---|---|---|---|
| Compound number | Rate (g/Ha) | AMARE | ABUTH | ECHCG | SETFA | ALOMY | ZEAMX |
| A34 | 1000 | 5 | 5 | 5 | 5 | | 3 |
| A35 | 1000 | 5 | 4 | 4 | 4 | | 2 |
| A36 | 1000 | 5 | 1 | 4 | 2 | 2 | 0 |
| A37 | 1000 | 5 | 5 | 5 | 4 | 4 | 3 |
| A38 | 1000 | 5 | 5 | 5 | 5 | | 3 |
| A39 | 1000 | 5 | 5 | 3 | 2 | 4 | 1 |
| A40 | 1000 | 5 | 4 | 3 | 2 | 2 | 2 |
| A41 | 1000 | 5 | 5 | 2 | 2 | 1 | 1 |
| A42 | 1000 | 4 | 1 | 0 | 3 | 0 | 0 |
| A43 | 1000 | 2 | 5 | 1 | 2 | 1 | 0 |
| A44 | 1000 | 5 | 5 | 5 | 4 | 4 | 2 |
| A45 | 1000 | 5 | 5 | 3 | 3 | 2 | 1 |
| A46 | 1000 | 5 | 5 | 4 | 2 | 4 | 3 |
| A47 | 1000 | 5 | 5 | 5 | 4 | 4 | 2 |
| A48 | 1000 | 5 | 5 | 1 | 3 | 4 | 1 |
| A49 | 1000 | 5 | 5 | 4 | 4 | 4 | 3 |
| A50 | 1000 | 5 | 5 | 5 | 4 | 4 | 2 |
| A51 | 1000 | 5 | 5 | 5 | 4 | 4 | 3 |
| A52 | 1000 | 5 | 5 | 5 | 4 | 4 | 2 |
| A53 | 1000 | 5 | 5 | 4 | 4 | 4 | 2 |
| A54 | 1000 | 5 | 5 | 2 | 2 | 3 | 0 |
| A55 | 1000 | 5 | 5 | 4 | 4 | 4 | 2 |
| A56 | 1000 | 5 | 5 | 1 | 1 | 2 | 0 |
| A57 | 1000 | 5 | 5 | 3 | 3 | 4 | 1 |
| A58 | 1000 | 5 | 5 | 3 | 3 | 4 | 4 |
| A59 | 1000 | 5 | 5 | 3 | 3 | 4 | 1 |
| A60 | 1000 | 5 | 5 | 1 | 1 | 1 | 0 |
| A61 | 1000 | 5 | 5 | 4 | 1 | 4 | 1 |
| A62 | 1000 | 5 | 4 | 4 | 3 | | 2 |
| A64 | 1000 | 5 | 2 | 4 | 3 | | 2 |
| A65 | 1000 | 5 | 5 | 5 | 5 | | 3 |
| A66 | 1000 | 5 | 5 | 5 | 4 | | 2 |
| A67 | 1000 | 5 | 5 | 5 | 5 | | 3 |
| A68 | 1000 | 0 | 0 | 0 | 0 | | 0 |
| A69 | 1000 | 5 | 5 | 5 | 5 | | 2 |
| A70 | 1000 | 5 | 5 | 5 | 5 | | 3 |
| A71 | 1000 | 5 | 5 | 5 | 0 | | 3 |
| A72 | 1000 | 5 | 5 | 5 | 5 | | 2 |
| A73 | 1000 | 5 | 5 | 4 | 5 | | 3 |
| A74 | 1000 | 5 | 5 | 4 | 4 | | 3 |
| A75 | 1000 | 5 | 5 | 4 | 4 | | 2 |
| A76 | 1000 | 5 | 5 | 3 | 4 | | 2 |
| A77 | 1000 | 5 | 5 | 5 | 5 | | 3 |
| A78 | 1000 | 5 | 5 | 4 | 3 | | 1 |
| A79 | 1000 | 5 | 5 | 5 | 5 | | 2 |
| A80 | 1000 | 5 | 5 | 5 | 4 | | 2 |
| A81 | 1000 | 3 | 2 | 0 | 2 | | 0 |
| A82 | 1000 | 5 | 5 | 3 | 3 | | 2 |
| A83 | 1000 | 5 | 5 | 4 | 4 | | 1 |
| A84 | 1000 | 5 | 5 | 5 | 5 | | 3 |
| A85 | 1000 | 5 | 5 | 5 | 5 | | 3 |
| A86 | 1000 | 5 | 5 | 5 | 5 | | 3 |
| A87 | 1000 | 5 | 5 | 4 | 4 | | 3 |
| A88 | 1000 | 5 | 5 | 4 | 4 | | 2 |
| A89 | 1000 | 5 | 5 | 4 | 4 | | 2 |
| A90 | 1000 | 5 | 3 | 4 | 4 | | 2 |
| A91 | 1000 | 5 | 5 | 4 | 4 | | 2 |
| A92 | 1000 | 5 | 5 | 5 | 4 | | 3 |
| A93 | 1000 | 5 | 5 | 5 | 5 | | 3 |
| A94 | 1000 | 5 | 5 | 5 | 5 | | 4 |
| A95 | 1000 | 5 | 5 | 5 | 5 | | 1 |
| A96 | 1000 | 5 | 5 | 4 | 4 | 4 | 1 |
| A97 | 1000 | 5 | 5 | 4 | 4 | 4 | 3 |
| A98 | 1000 | 0 | 0 | 0 | 0 | 0 | 0 |
| A99 | 1000 | 5 | 1 | 0 | 0 | 0 | 0 |
| A100 | 1000 | 5 | 5 | 3 | 3 | 4 | 1 |
| A101 | 1000 | 5 | 5 | 4 | 4 | 4 | 0 |
| A102 | 1000 | 5 | 5 | 4 | 3 | | 1 |
| A103 | 1000 | 2 | 1 | 1 | 4 | | 1 |
| A104 | 1000 | 5 | 4 | 5 | 5 | | 3 |
| A105 | 1000 | 5 | 5 | 5 | 5 | | 4 |
| A106 | 1000 | 5 | 5 | 4 | 3 | | 2 |
| A107 | 1000 | 5 | 5 | 5 | 4 | | 2 |
| A108 | 1000 | 5 | 5 | 5 | 4 | | 2 |

Example 27b: Post-Emergence Herbicidal Activity

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions (at 24/16° C., day/night; 14 hours light; 65% humidity) and watered twice daily. After 13 days, the test was evaluated (5=total damage to plant; 0=no damage to plant). Results are shown in Table 3.

TABLE 3

| Compound number | Rate (g/Ha) | ECHCG | SETFA | AMARE | ABUTH | ALOMY | ZEAMX |
|---|---|---|---|---|---|---|---|
| A1 | 1000 | 5 | 5 | 5 | 5 | 5 | 3 |
| A2 | 1000 | 5 | 5 | 5 | 5 | 4 | 2 |
| A3 | 1000 | 5 | 5 | 5 | 5 | 5 | 5 |
| A4 | 1000 | 5 | 5 | 5 | 5 | 5 | 5 |
| A5 | 1000 | 4 | 4 | 5 | 5 | 4 | 2 |
| A6 | 1000 | 5 | 5 | 5 | 5 | 5 | 2 |
| A7 | 1000 | 5 | 5 | 5 | 5 | 4 | 4 |
| A8 | 1000 | 5 | 5 | 5 | 5 | 5 | 4 |
| A9 | 1000 | 5 | 5 | 5 | 5 | 5 | 4 |
| A10 | 1000 | 5 | 5 | 5 | 5 | 5 | 4 |
| A11 | 1000 | 5 | 5 | 5 | 5 | 4 | 4 |
| A12 | 1000 | 5 | 5 | 5 | 5 | 5 | 5 |
| A13 | 1000 | 5 | 5 | 5 | 5 | 4 | 0 |
| A14 | 1000 | 5 | 5 | 5 | 5 | 4 | 3 |
| A15 | 1000 | 4 | 4 | 5 | 5 | 4 | 0 |
| A16 | 1000 | 5 | 5 | 5 | 5 | 5 | 2 |
| A17 | 1000 | 5 | 5 | 5 | 5 | 5 | 4 |
| A18 | 1000 | 5 | 5 | 5 | 5 | 5 | 3 |
| A19 | 1000 | 5 | 5 | 5 | 5 | 5 | 4 |
| A20 | 1000 | 5 | 5 | 5 | 5 | 5 | 4 |
| A21 | 1000 | 5 | 5 | 5 | 5 | 5 | 3 |
| A22 | 1000 | 5 | 5 | 5 | 5 | 5 | 5 |
| A23 | 1000 | 2 | 4 | 5 | 5 | 4 | 2 |
| A24 | 1000 | 5 | 5 | 5 | 5 | 5 | 4 |
| A25 | 1000 | 5 | 5 | 5 | 5 | 5 | 5 |
| A26 | 1000 | 1 | 1 | 3 | 4 | 1 | 1 |
| A27 | 1000 | 3 | 3 | 5 | 5 | 3 | 3 |
| A28 | 1000 | 5 | 5 | 4 | 4 | 5 | 2 |
| A29 | 1000 | 4 | 3 | 5 | 5 | 4 | 2 |
| A30 | 1000 | 5 | 5 | 5 | 5 | 5 | 3 |
| A31 | 1000 | 5 | 5 | 5 | 5 |  | 4 |
| A32 | 1000 | 5 | 5 | 5 | 5 | 5 | 2 |
| A33 | 1000 | 1 | 2 | 3 | 5 | 4 | 1 |
| A34 | 1000 | 5 | 5 | 5 | 5 |  | 4 |
| A35 | 1000 | 3 | 3 | 5 | 0 |  | 1 |
| A36 | 1000 | 5 | 3 | 5 | 1 | 4 | 2 |
| A37 | 1000 | 5 | 5 | 5 | 5 | 5 | 4 |
| A38 | 1000 | 5 | 5 | 5 | 5 |  | 4 |
| A39 | 1000 | 5 | 5 | 5 | 5 | 5 | 1 |
| A40 | 1000 | 4 | 3 | 5 | 5 | 4 | 1 |
| A41 | 1000 | 2 | 4 | 5 | 5 | 4 | 2 |
| A42 | 1000 | 0 | 2 | 4 | 4 | 2 | 1 |
| A43 | 1000 | 5 | 0 | 1 | 5 | 1 | 2 |
| A44 | 1000 | 5 | 5 | 5 | 5 | 4 | 4 |
| A45 | 1000 | 3 | 3 | 5 | 5 | 2 | 1 |
| A46 | 1000 | 5 | 5 | 5 | 5 | 5 | 3 |
| A47 | 1000 | 5 | 5 | 5 | 5 | 5 | 4 |
| A48 | 1000 | 4 | 4 | 5 | 5 | 4 | 1 |
| A49 | 1000 | 5 | 5 | 5 | 5 | 5 | 4 |
| A50 | 1000 | 5 | 5 | 5 | 5 | 5 | 5 |
| A51 | 1000 | 5 | 5 | 5 | 5 | 5 | 5 |
| A52 | 1000 | 5 | 5 | 5 | 5 | 5 | 5 |
| A53 | 1000 | 5 | 5 | 5 | 5 | 5 | 3 |
| A54 | 1000 | 5 | 5 | 5 | 5 | 5 | 4 |
| A55 | 1000 | 5 | 5 | 5 | 5 | 5 | 4 |
| A56 | 1000 | 3 | 2 | 5 | 5 | 4 | 1 |
| A57 | 1000 | 5 | 5 | 5 | 5 | 5 | 4 |
| A58 | 1000 | 5 | 5 | 5 | 5 | 4 | 4 |
| A59 | 1000 | 5 | 5 | 5 | 5 | 5 | 4 |
| A60 | 1000 | 4 | 3 | 5 | 5 | 4 | 3 |
| A61 | 1000 | 5 | 5 | 5 | 5 | 5 | 3 |
| A62 | 1000 | 5 | 5 | 5 | 5 |  | 2 |
| A64 | 1000 | 5 | 4 | 5 | 4 |  | 1 |
| A65 | 1000 | 5 | 5 | 5 | 5 |  | 5 |

TABLE 3-continued

| | | Application post-emergence | | | | | |
|---|---|---|---|---|---|---|---|
| Compound number | Rate (g/Ha) | ECHCG | SETFA | AMARE | ABUTH | ALOMY | ZEAMX |
| A66 | 1000 | 5 | 5 | 5 | 5 | | 5 |
| A67 | 1000 | 5 | 5 | 5 | 5 | | 4 |
| A68 | 1000 | 0 | 0 | 0 | 0 | | 0 |
| A69 | 1000 | 5 | 4 | 4 | 5 | | 3 |
| A70 | 1000 | 5 | 5 | 5 | 5 | | 5 |
| A71 | 1000 | 5 | 5 | 5 | 5 | | 4 |
| A72 | 1000 | 5 | 5 | 5 | 5 | | 2 |
| A73 | 1000 | 5 | 5 | 5 | 5 | | 3 |
| A74 | 1000 | 4 | 5 | 5 | 5 | | 3 |
| A75 | 1000 | 5 | 5 | 5 | 5 | | 2 |
| A76 | 1000 | 4 | 4 | 5 | 5 | | 1 |
| A77 | 1000 | 5 | 5 | 5 | 5 | | 5 |
| A78 | 1000 | 5 | 3 | 5 | 5 | | 0 |
| A79 | 1000 | 5 | 5 | 5 | 5 | | 4 |
| A80 | 1000 | 5 | 5 | 5 | 5 | | 4 |
| A81 | 1000 | 2 | 2 | 4 | 4 | | 0 |
| A82 | 1000 | 4 | 4 | 5 | 5 | | 2 |
| A83 | 1000 | 1 | 4 | 5 | 5 | | 1 |
| A84 | 1000 | 5 | 5 | 5 | 5 | | 4 |
| A85 | 1000 | 5 | 5 | 5 | 5 | | 4 |
| A86 | 1000 | 5 | 5 | 5 | 5 | | 2 |
| A87 | 1000 | 5 | 5 | 5 | 5 | | 4 |
| A88 | 1000 | 5 | 5 | 5 | 5 | | 3 |
| A89 | 1000 | 5 | 5 | 5 | 5 | | 3 |
| A90 | 1000 | 5 | 5 | 5 | 5 | | 5 |
| A91 | 1000 | 5 | 4 | 5 | 5 | | 3 |
| A92 | 1000 | 5 | 5 | 5 | 5 | | 4 |
| A93 | 1000 | 5 | 5 | 5 | 5 | | 4 |
| A94 | 1000 | 5 | 5 | 5 | 5 | | 5 |
| A95 | 1000 | 5 | 5 | 5 | 5 | | 2 |
| A96 | 1000 | 5 | 5 | 5 | 5 | 5 | 3 |
| A97 | 1000 | 5 | 5 | 5 | 5 | 5 | 3 |
| A98 | 1000 | 0 | 0 | 4 | 0 | 0 | 1 |
| A99 | 1000 | 3 | 0 | 5 | 1 | 0 | 1 |
| A100 | 1000 | 5 | 5 | 5 | 5 | 5 | 4 |
| A101 | 1000 | 5 | 5 | 5 | 5 | 5 | 3 |
| A102 | 1000 | 2 | 1 | 5 | 5 | | 1 |
| A103 | 1000 | 0 | 1 | 2 | 0 | | 1 |
| A104 | 1000 | 5 | 5 | 5 | 5 | | 5 |
| A105 | 1000 | 5 | 5 | 5 | 5 | | 5 |
| A106 | 1000 | 4 | 4 | 5 | 5 | | 1 |
| A107 | 1000 | 5 | 5 | 5 | 5 | | 3 |
| A108 | 1000 | 5 | 5 | 5 | 5 | | 5 |

ABUTH = *Abutilon theophrasti*;
AMARE = *Amaranthus retroflexus*;
SETFA = *Setaria faberi*;
ALOMY = *Alopecurus myosuroides*;
ECHCG = *Echinochloa crus-galli*;
ZEAMX = *Zea mays*.

The invention claimed is:

1. A compound of formula (I)

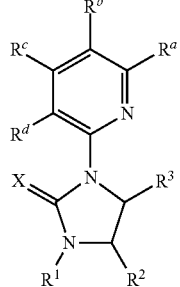

wherein X is oxygen; $R^1$ is methoxy; $R^3$ is hydroxyl; $R^2$ is methyl; $R^a$ is hydrogen; $R^b$ is hydrogen; $R^c$ is trifluoromethyl; and $R^d$ is hydrogen.

2. The compound of claim 1, wherein the compound is:

3. The compound of claim 1, wherein the compound is:

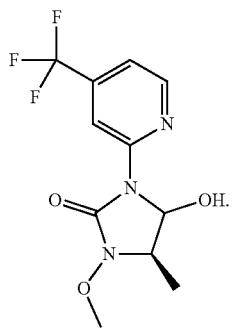 [SMILES: CON1C(=O)N(c2cc(C(F)(F)F)ccn2)C(O)[C@H]1C]

4. A herbicidal composition comprising a compound of formula I as defined in claim 1 together with at least one agriculturally acceptable adjuvant or diluent.

5. The composition according to claim 4 which comprises a further herbicide in addition to the compound of formula I.

6. The composition according to claim 4, further comprising a safener.

7. A method of controlling weeds in crops of useful plants, the method comprising applying to the weeds or to the locus of the weeds, or to the useful plants or to the locus of the useful plants, a compound of formula I as defined in claim 1.

8. The composition according to claim 5, further comprising a safener.

9. A method of controlling weeds in crops of useful plants, comprising applying to the weeds or to the locus of the weeds, or to the useful plants or to the locus of the useful plants, a composition as claimed in claim 4.

* * * * *

UNITED STATES PATENT AND TRADEMARK OFFICE
CERTIFICATE OF CORRECTION

| | | |
|---|---|---|
| PATENT NO. | : 11,608,323 B2 | Page 1 of 1 |
| APPLICATION NO. | : 16/222900 | |
| DATED | : March 21, 2023 | |
| INVENTOR(S) | : Morris et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 401 days.

Signed and Sealed this
Thirty-first Day of December, 2024

Derrick Brent
*Acting Director of the United States Patent and Trademark Office*